United States Patent [19]

Ogawa et al.

[11] Patent Number: 5,250,669
[45] Date of Patent: Oct. 5, 1993

[54] PHOTOSENSITIVE COMPOUND

[75] Inventors: Kazufumi Ogawa, Hirakata; Masayuki Endo, Izumi; Keiji Ohno, Sakado; Mamoru Nagoya, Saitama, all of Japan

[73] Assignees: Wako Pure Chemical Industries, Ltd.; Matsushita Electric Industrial Co., Ltd., both of Osaka, Japan

[21] Appl. No.: 873,490

[22] Filed: Apr. 23, 1992

Related U.S. Application Data

[63] Continuation of Ser. No. 676,471, Mar. 27, 1991, abandoned, which is a continuation of Ser. No. 277,742, Nov. 30, 1988, abandoned.

[30] Foreign Application Priority Data

Dec. 4, 1987 [JP] Japan ................. 62-306878
Dec. 7, 1987 [JP] Japan ................. 62-309336
Dec. 8, 1987 [JP] Japan ................. 62-310737

[51] Int. Cl.$^5$ ............... C07C 245/00; G03F 7/022
[52] U.S. Cl. ..................... 534/557; 534/556; 430/189; 430/192; 430/193
[58] Field of Search .......... 430/192, 193, 165, 166; 534/556, 557

[56] References Cited

U.S. PATENT DOCUMENTS

| | | | |
|---|---|---|---|
| 3,046,119 | 7/1962 | Süs | 534/557 |
| 3,046,122 | 7/1962 | Süs | 534/557 |
| 3,969,118 | 7/1976 | Stahlhofen et al. | 430/193 |
| 4,339,522 | 7/1982 | Balanson et al. | 430/193 |
| 4,458,000 | 7/1984 | Stahlhofen | 430/191 |
| 4,622,283 | 11/1986 | Gray | 430/193 |
| 4,735,885 | 4/1988 | Hopf et al. | 430/193 |

OTHER PUBLICATIONS

Korobitsyna, I. K. et al., Zh. Org. Khim. 12, pp. 1245-1260, 1976.
Grant, B. D. et al., IEEE Transactions on Electron Devices, vol. ED-28, No. 11, pp. 1300-1305, Nov. 1981.
English Language Abstract of Japanese Patent Publication #62-036661, published Feb. 17, 1987, (Nippon T. & T.).
English Language Abstract of Japanese Patent Publication #63-253,940, published Oct. 20, 1988, (Matsushita Elec. Ind. K. K.).

*Primary Examiner*—Charles L. Bowers, Jr.
*Assistant Examiner*—John S. Chu
*Attorney, Agent, or Firm*—Armstrong, Westerman, Hattori, McLeland & Naughton

[57] ABSTRACT

Photosensitive compounds having preferably a functional group such as $-SO_2Cl$, $-SO_3H$, $-SO_3R$,

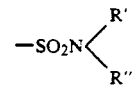

(R, R', R" being alkyl) on a terminal benzene or naphthalene ring connected via a methylene group and

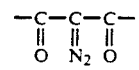

moiety are improved in sensitivity to light and thermal stability, and thus useful in a photo resist.

12 Claims, 3 Drawing Sheets

PHOTOSENSITIVE COMPOUND

This application is a continuation of application Ser. No.07/676,471, filed Mar. 27, 1991, which is a continuation of application Ser. No. 07/277,742, filed Nov. 30, 1988, both now abandoned.

BACKGROUND OF THE INVENTION

This invention relates to a photosensitive compound useful as a photosensitive agent for lithography, e.g. for producing semiconductor devices.

With recent higher density and larger scale integration of semiconductor devices, wavelengths used in exposing devices for minute processing, particularly for lithography become shorter and shorter. Now, KrF excimer laser light (248.4 nm) is studied. But, there have been no photosensitive materials suitable for such a wavelength.

For example, even when MP 2400 (mfd. by Shipley Corp.), which is known among photoresists to have high sensitivity to KrF excimer laser light and good light transmittance, is used, pattern formation after development is very bad and cannot be used practically [K. Ogawa et al., J. Electrochem. Soc., 135, p2347 (1988)].

This seems to be derived from the fact that MP 2400 resist has a large surface absorption for the exposed light.

This can be interpreted that the main polymer (resin) per se used in the resist has a large light absorption against the exposed light, or a photosensitive material in the resist has no good light reactivity. That is, photosensitive materials such as naphthoquinone diazides heretofore used in known resists generally have a large absorption against a light near 248.4 nm and are hardly improved in transmittance after exposure to light. For example, in the case of MP 2400 with a film thickness of 1 μm, changes in light transmittance before and after exposure to light of KrF excimer laser (248.4 nm) is only about 3% at 248.4 nm as shown in FIG. 3 wherein the full line is before exposure and the dotted line is after exposure. This means that the reactivity is poor.

On the other hand, U.S. Pat. No. 4,622,283 to Gray discloses a lithographic resist composition for use with deep UV light of less than 300 nm wavelength containing as a photosensitive solubilizing agent a compound of the formula:

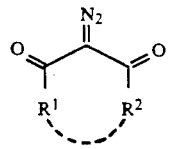

wherein $R^1$ and $R^2$ can each individually be alkyl, aryl, alkoxyalkyl, aralkyl or haloalkyl radicals or $R^1$ and $R^2$ taken together can be an alkylene radical. But this composition is insufficient in preventing non-light exposed portion from erosion of an alkaline developing solution to cause erosion of retaining portions of resist film (hereinafter referred to as "film erosion") in large amounts, which results in causing deterioration in contrast of the resist pattern.

Further, U.S. Pat. No. 4,339,522 to Balanso et al disclose a lithographic resist composition comprising a phenolic-aldehyde resin and a deep ultraviolet sensitizer of the formula:

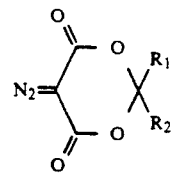

wherein $R_1$ is alkyl or aryl; and $R_2$ is H, alkyl or aryl, or together $R_1$ and $R_2$ are cycloalkyl. But this U.S. Patent is quite silent on the reactivity against KrF excimer laser, resistance to alkaline developing solution and improvement in the contrast.

SUMMARY OF THE INVENTION

It is an object of the present invention to provide photosensitive compounds having good reactivity against deep ultraviolet light near 248.4 nm so as to overcome defects of known lithographic resist compositions.

It is another object of the present invention to provide process for producing the photosensitive compounds.

The present invention provides a photosensitive compound represented by the formula:

$$R^1-\underset{\underset{O}{\|}}{C}-\underset{\underset{N_2}{\|}}{C}-\underset{\underset{O}{\|}}{C}-R^2 \qquad (I)$$

wherein $R^1$ is

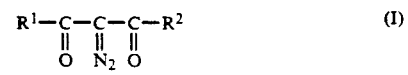

$X^1$ and $Y^1$ are independently a hydrogen atom, a halogen atom, a lower alkyl group having 1 to 5 carbon atoms, a lower alkoxy group having 1 to 5 carbon atoms, $-SO_2Cl$, $-SO_2Br$,

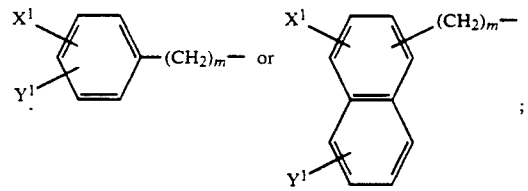

$-SO_3H$ or $-SO_3R^5$; $R^3$ and $R^4$ are independently a hydrogen atom or a lower alkyl group having 1 to 5 carbon atoms, which may have one or more substituents, or $R^3$, $R^4$ and N taken together may form a heterocyclic ring such as a piperazine ring, a piperidine ring, a pyrrolidine ring, a morpholine ring, or the like; $R^5$ is a lower alkyl group having 1 to 5 carbon atoms; the $-SO_2Cl$ or $-SO_2Br$ group may include a quaternary salt thereof; the $-SO_3H$ group may include an ammonium salt thereof, an organic base salt thereof and a quaternary salt thereof; m is an integer of 1 to 20; $R^2$ is an alkyl group, a cycloalkyl group, a hydroxyalkyl group, an alkoxyalkyl group,

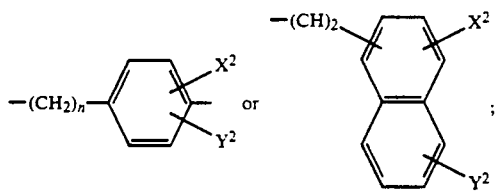

$X^2$ and $Y^2$ are independently a hydrogen atom, a halogen atom, a lower alkyl group having 1 to 5 carbon atoms, a lower alkoxy group having 1 to 5 carbon atoms, $-SO_2Cl$, $-SO_2Br$,

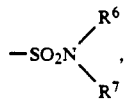

$-SO_3H$ or $-SO_3R^8$; $R^6$ and $R^7$ are independently a hydrogen atom or a lower alkyl group having 1 to 5 carbon atoms which may have one or more substituents, or $R^6$, $R^7$ and N taken together may form a heterocyclic ring such as a piperazine ring, a piperidine ring, a pyrrolidine ring, a morpholine ring, or the like; $R^8$ is a lower alkyl group having 1 to 5 carbon atoms; the $-SO_2Cl$ or $-SO_2Br$ group may include a quaternary salt thereof; the $-SO_3H$ group may include an ammonium salt thereof, an organic base salt thereof and a quaternary salt thereof; n is an integer of 1 to 20; or $R^1$ and $R^2$ taken together may form a group of the formula:

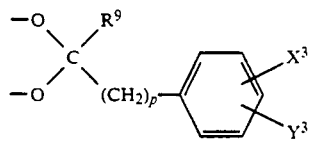

wherein $R^9$ is an alkyl group, an aralkyl group, a hydroxyalkyl group or an alkoxyalkyl group; $X^3$ and $Y^3$ are independently a hydrogen atom, a halogen atom, a lower alkyl group having 1 to 5 carbon atoms, a lower alkoxy group having 1 to 5 carbon atoms, $-SO_2Cl$, $-SO_2Br$,

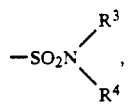

$-SO_3H$ or $-SO_3R^5$; $R^3$, $R^4$ and $R^5$ are as defined above; the $-SO_2Cl$ or $-SO_2Br$ group may include a quaternary salt thereof; the $-SO_3H$ group may include an ammonium salt thereof, an organic base thereof and a quaternary salt thereof; and p is an integer of 1 to 20.

The photosensitive compounds of the formula (I) can be produced by various ways.

DESCRIPTION OF THE PREFERRED EMBODIMENTS

Figure 1A:
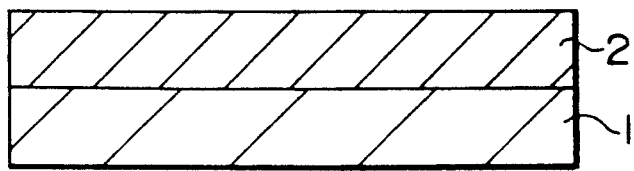
FIGS. 1(a) to (c) are cross-sectional views explaining one example of a pattern forming process using a photosensitive compound of the present invention.

The photosensitive compound of the present invention is represented by the formula;

$$R^1-\underset{\underset{O}{\|}}{C}-\underset{\underset{N_2}{\|}}{C}-\underset{\underset{O}{\|}}{C}-R^2 \qquad (I)$$

wherein $R^1$ is

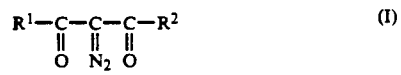

$X^1$ and $Y^1$ are independently a hydrogen atom, a halogen atom, such as Cl, Br, I or F, a lower alkyl group having 1 to 5 carbon atoms, a lower alkoxy group having 1 to 5 carbon atoms, $-SO_2Cl$, $-SO_2Br$,

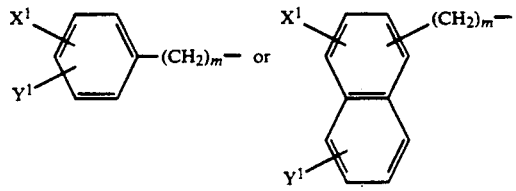

$-SO_3H$, or $-SO_3R^5$; $R^3$ and $R^4$ are independently a hydrogen atom or a lower alkyl group having 1 to 5 carbon atoms, which may have one or more substituents, or $R^3$, $R^4$ and N taken together may form a heterocyclic ring such as a piperazine ring, a piperidine ring, a pyrrolidine ring, a morpholine ring, or the like; $R^5$ is a lower alkyl group having 1 to 5 carbon atoms; the $-SO_2Cl$ or $-SO_2Br$ group may include a quaternary salt thereof; the $-SO_3H$ group may include an ammonium salt thereof, an organic base salt thereof and a quaternary salt thereof; m is an integer of 1 to 20; $R^2$ is an alkyl group, a cycloalkyl group, a hydroxyalkyl group, an alkoxyalkyl group,

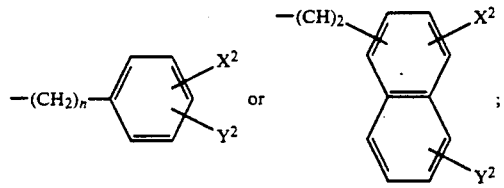

$X^2$ and $Y^2$ are independently a hydrogen atom, a halogen atom such as Cl, Br, I or F, a lower alkyl group having 1 to 5 carbon atoms, a lower alkoxy group having 1 to 5 carbon atoms, $-SO_2Cl$, $-SO_2Br$,

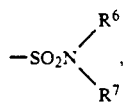

—SO₃H or —SO₃R⁸; R⁶ and R⁷ are independently a hydrogen atom or a lower alkyl group having 1 to 5 carbon atoms which may have one or more substituents, or R⁶, R⁷ and N taken together may form a heterocyclic ring such as a piperazine ring, a piperidine ring, a pyrrolidine ring, a morpholine ring, or the like; R⁸ is a lower alkyl group having 1 to 5 carbon atoms; the —SO₂Cl or —SO₂Br group may include a quaternary salt thereof, the —SO₃H group may include an ammonium salt thereof, an organic base salt thereof and a quaternary salt thereof; n is an integer of 1 to 20; or R¹ and R² taken together may form a group of the formula:

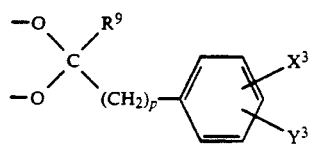

wherein R⁹ is an alkyl group, an aralkyl group, a hydroxyalkyl group or an alkoxyalkyl group; X³ and Y³ are independently a hydrogen atom, a halogen atom such as Cl, Br, I or F, a lower alkyl group having 1 to 5 carbon atoms, a lower alkoxy group having 1 to 5 carbon atoms, —SO₂Cl, —SO₂Br,

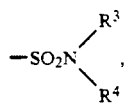

—SO₃H or —SO₃R⁵; R³, R⁴ and R⁵ are as defined above; the —SO₂Cl or —SO₂Br group may includes a quaternary salt thereof; the —SO₃H group may include an ammonium salt thereof, an organic base salt thereof and a quaternary salt thereof; and p is an integer of 1 to 20.

As the base which can form a quaternary salt with —SO₂Cl or —SO₂Br, there can be used pyridine, piperazine, piperidine, N-methylpyrrolidine, morpholine, diethylamine, triethylamine, etc.

As the salt of organic base of —SO₃H and the quaternary salt, there can be used salts of —SO₃H and a base such pyridine, piperzine, piperidine, N-methylpyrrolidine, morpholine, diethylamine, triethylamine, or the like.

The photosensitive compound of the formula (I) concretely includes the following compounds:

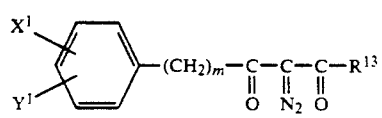

wherein X¹, Y¹ and m are as defined above; and R¹³ is an alkyl group, a cycloalkyl group, a hydroxyalkyl group or an alkoxyalkyl group,

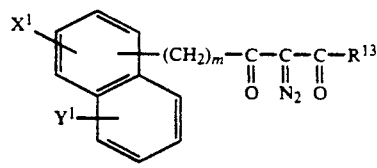

wherein X¹, Y¹, R¹³ and m are as defined above,

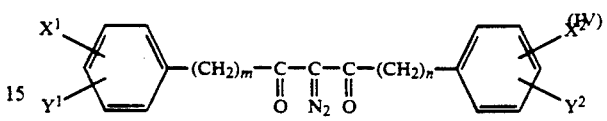

wherein X¹, Y¹, X², Y², m and n are as defined above,

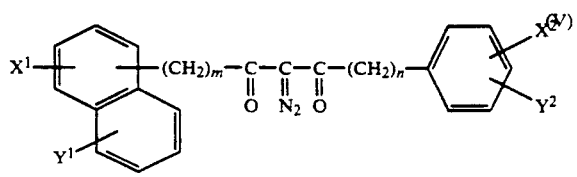

wherein X¹, Y¹, X², Y², m and n are as defined above,

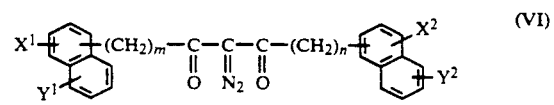

wherein X¹, Y¹, X², Y², m and n are as defined above,

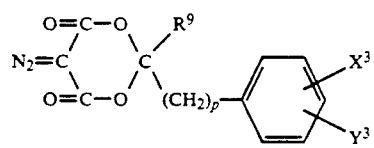

wherein X¹, Y¹, X², Y², m and n are as defined above, and

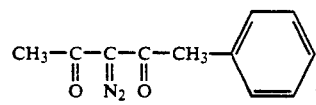

wherein X³, Y³, R⁹ and p are as defined above.

Preferable examples of the compounds of the formula (I) are as follows.

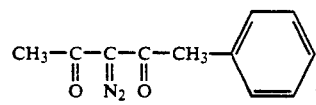

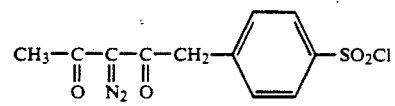

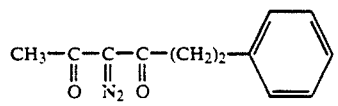

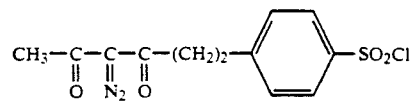

-continued
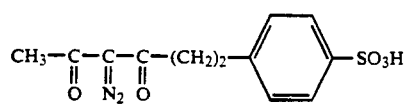 5
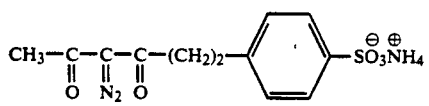 10
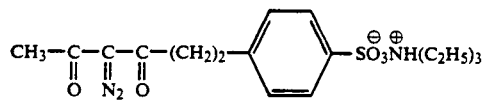 15
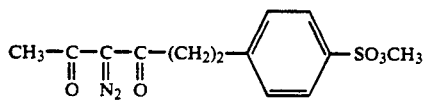 20
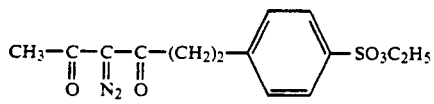 25
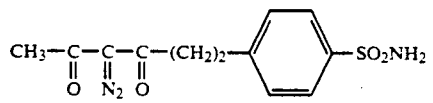 30
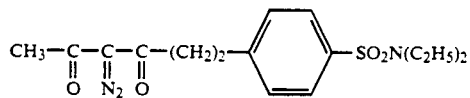 35
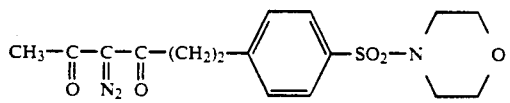 40
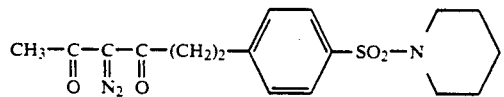 45
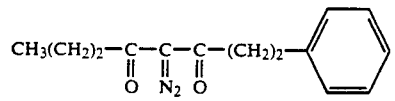 50
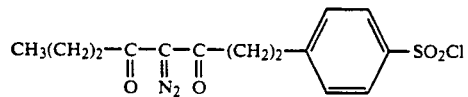 55
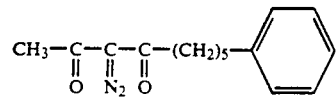 60
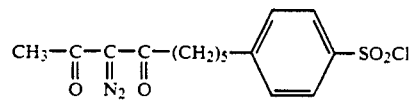 65
-continued
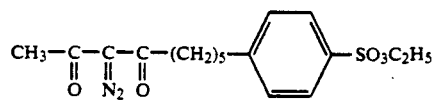
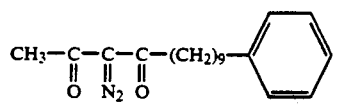
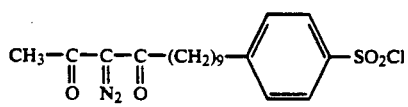
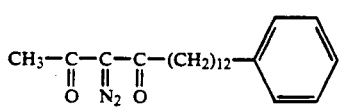
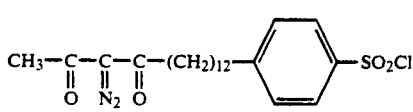
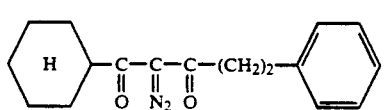
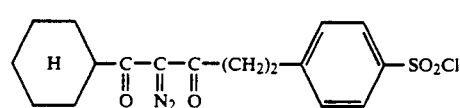
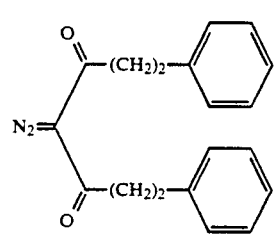
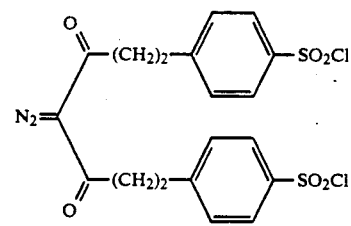
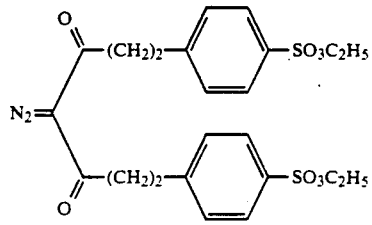

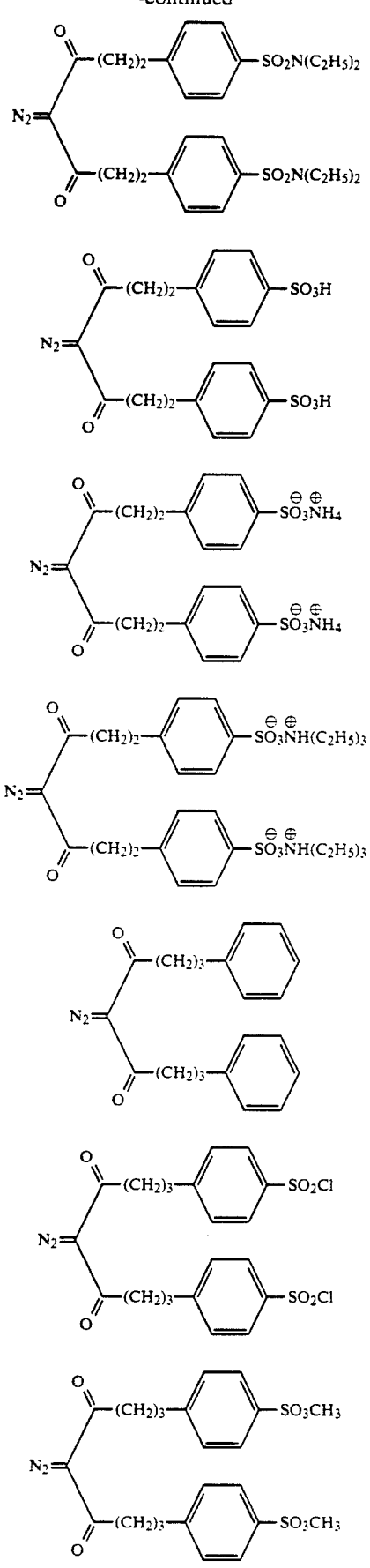

-continued
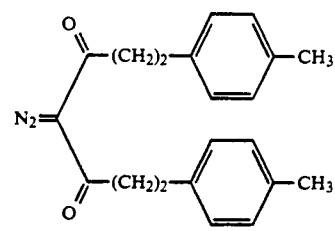
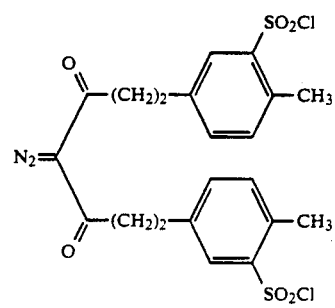
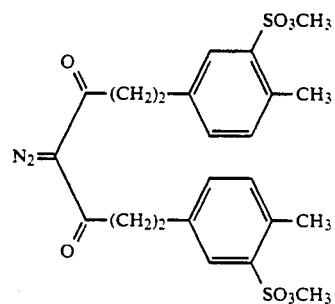
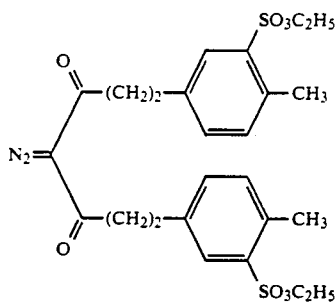
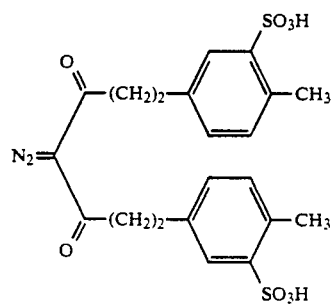
-continued
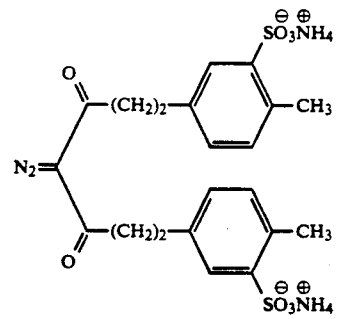
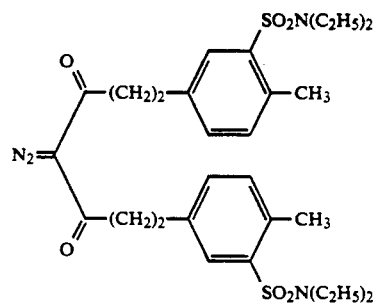
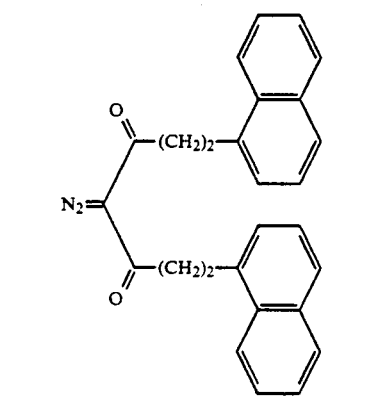
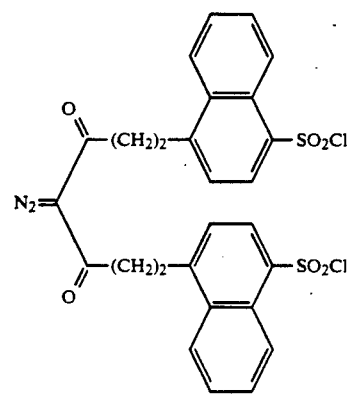

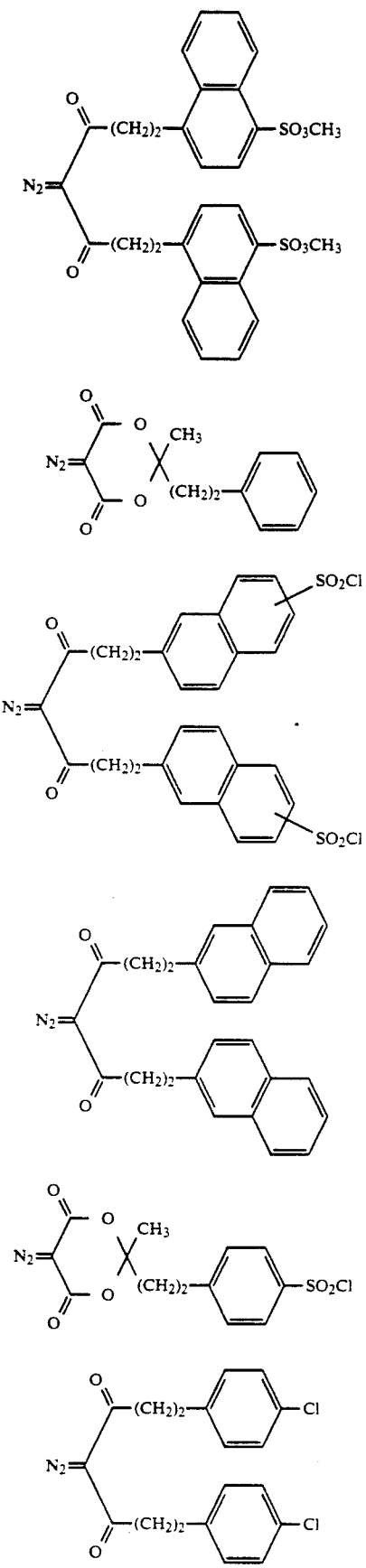

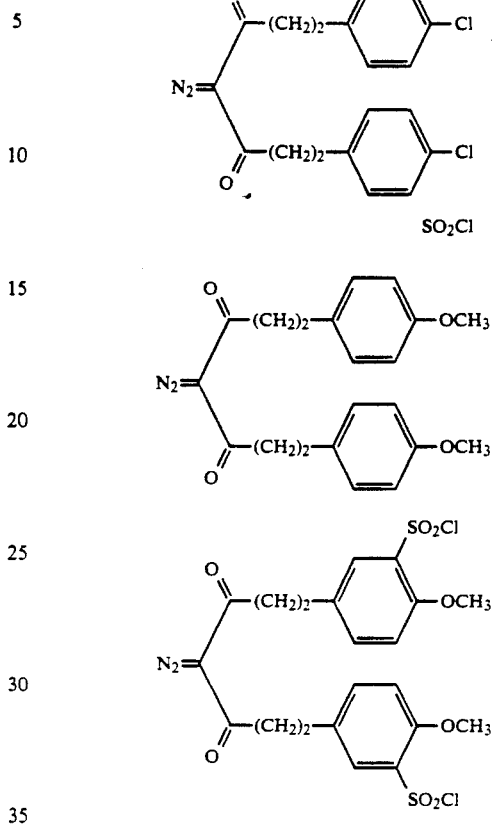

The compounds of the formula (I) can be produced by various ways.

For example, the production of the compound of the formula (II), wherein $X^1$ is a hydrogen atom, a halogen atom, a lower alkyl group or a lower alkoxy group (hereinafter defined as $Z^1$) and $Y^1$ is $-SO_2Cl$, that is, a compound of the formula:

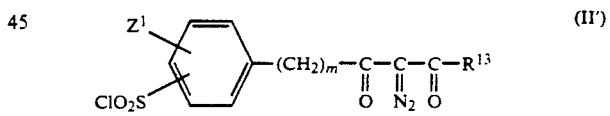

(II')

wherein $Z^1$, $R^{13}$ and m are as defined above, can be produced by reacting a compound of the formula:

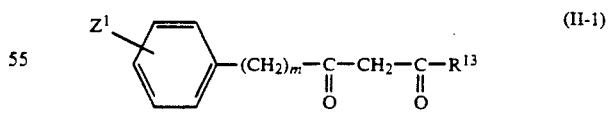

(II-1)

with a diazotizing agent in the presence of a base such as an organic base to form a compound of the formula:

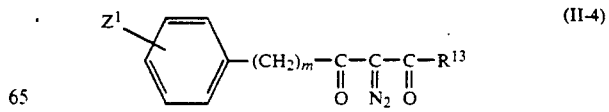

(II-4)

which is then reacted with chlorosulfonic acid.

In the above reactions, the diazotization can be carried out under the following conditions.

As the diazotizing agent, there can be used p-toluenesulfonylazide, benzenesulfonylazide, 2-azide-3-ethylbenzothiazolium fluoroborate, etc.

As the solvent, there can be used an alcohol such as ethanol, isopropanol, etc.; an ether such as ethyl ether, isopropyl ether, tetrahydrofuran, etc.; a halogenated hydrocarbon such as dichloromethane, chloroform, carbon tetrachloride, 1,2-dichloroethane, etc.; a hydrocarbon such as n-hexane, cyclohexane, toluene, etc.

As the base, there can be used an organic base such as piperidine, triethylamine, N-methylpyrrolidine, N-methylmorpholine, pyridine, diethylamine, etc.; an alcoholate such as $NaOCH_3$, $NaOC_2H_5$, $KOC(CH_3)_3$, $KOC_2H_5$, etc.; and Na, NaH, KH, etc.

The diazotizing agent is used in an amount of preferably 0.5 to 3 moles, more preferably 0.8 to 1.5 moles per mole of the compound (II-1). The base is used in an amount of preferably 0.5 to 5 moles, more preferably 0.8 to 1.5 moles per mole of the compound (II-1).

The reaction is carried out preferably at a temperature of $-10°$ to $30°$ C., more preferably $-5°$ to $10°$ C., for preferably 15 minutes to 5 hours, more preferably 1 to 2 hours.

The chlorosulfonation can be carried out in a solvent or in the absence of a solvent under the following conditions.

As the solvent, there can be used a chlorinated hydrocarbon such as carbon tetrachloride, tetrachloroethane, chloroform, 1,2-dichloroethane, dichloromethane, etc., carbon disulfide, so as to suppress side reactions.

Chlorosulfonic acid is used in an amount of preferably 1 to 10 moles, more preferably 2.5 to 4.5 moles, per mole of the compound (II-4).

The reaction is carried out preferably at a temperature of $-20°$ to $20°$ C., more preferably $-10°$ to $5°$ C., for preferably 15 minutes to 5 hours, more preferably 1 to 2 hours.

The compound of the formula (II') can also be produced by reacting a compound of the formula:

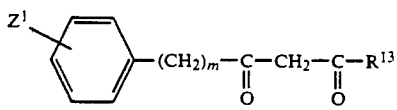
(II-1)

wherein $Z^1$, $R^{13}$ and m are as defined above, with a sulfonating agent, followed by neutralization to yield a compound of the formula:

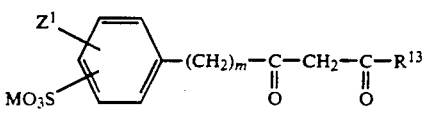
(II-2)

wherein M is an alkali metal atom, an ammonium group or a residue of an organic base; $Z^1$, $R^{13}$ and m are as defined above, reacting the compound of the formula (II-2) with a diazotizing agent in the presence of a base to yield a compound of the formula:

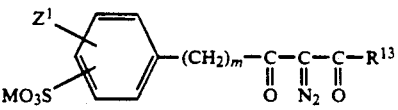
(II-3)

wherein M, $Z^1$, $R^{13}$ and m are as defined above, followed by reaction with a chlorinating agent.

In the above reactions, the sulfonation can be carried out under the following conditions.

As the sulfonating agent, there can be used chlorosulfonic acid, sulfuric acid, fuming sulfuric acid, anhydrous sulfuric acid (sulfur trioxide), a complex of dioxane and anhydrous sulfuric acid, a complex of pyridine and anhydrous sulfuric acid, etc.

As a solvent, in the case of using sulfuric acid, there can be used glacial acetic acid, acetic anhydride, ethyl acetate, ethyl ether, acetonitrile, carbon tetrachloride, etc.; and in the case of using other sulfonating agents, there can be used carbon disulfide, 1,2-dichloroethane, tetrachloroethane, chloroform, carbon tetrachloride, dichloromethane, nitromethane, nitrobenzene, etc.

The sulfonating agent is used in an amount of preferably 1 to 10 moles, more preferably 1 to 3 moles, per mole of the compound (II-1).

The reaction can be carried out preferably at $-10°$ to $30°$ C., more preferably $-5°$ to $5°$ C., preferably in the presence of a Ta powder as a catalyst in the case of using chlorosulfonic acid, or preferably at $0°$ to $100°$ C., more preferably at $0°$ to $10°$ C. during the dropwise addition of a sulfonating agent such as sulfonic acid, fuming sulfuric acid, anhydrous sulfuric acid or a complex, and finally raised to $50°$ to $100°$ C. After the dropwise addition of sulfonating agent, the reaction is preferably carried out for 1 to 3 hours.

The neutralization is carried out by using a neutralizing agent (for inserting M), for example, a potassium salt such as KCl, $K_2CO_3$, KOH, KOR (R is an alkyl group), $KHCO_3$, etc.; a sodium salt such as NaCl, $Na_2CO_3$, NaOH, NaOR (R is an alkyl group), $NaHCO_3$, etc.; an ammonium salt such as $NH_4Cl$, $(NH_4)_2CO_3$, $NH_4HCO_3$, $NH_3$, etc.; an organic base such as $(C_2H_5)_3N$, $(C_2H_5)_2NH$, etc.

The diazotization can be carried out under the following conditions.

As the diazotizing agent, there can be used p-toluenesulfonylazide, benzenesulfonylazide, 2-azido-3-ethylbenzothiazolium fluoroborate, etc.

As the solvent, there can be used an alcohol such as ethanol, isopropanol, etc.; an ether such as ethyl ether, isopropyl ether, tetrahydrofuran, etc.; a halogenated hydrocarbon such as dichloromethane, chloroform, carbon tetrachloride, etc.; a hydrocarbon such as n-hexane, cyclohexane, etc.; an amide such as N,N-dimethylformamide (DMF), formamide, hexamethylphosphoramide (HMPA), etc.

As the base, there can be used an organic base such as triethylamine, piperidine, etc.; an alcoholate such as $NaOCH_3$, $NaOC_2H_5$, etc.

The diazotizing agent is used in an amount of preferably 0.5 to 3 moles, more preferably 0.8 to 1.5 moles, per mole of the compound (II-2). The base is used in an amount of preferably 0.5 to 5 moles, more preferably 0.8 to 1.5 moles, per mole of the compound (II-2).

The reaction can be carried out at preferably $-10°$ to $30°$ C., more preferably $-5°$ to $10°$ C., for preferably 15 minutes to 5 hours, more preferably 1 to 2 hours.

The chlorination can be carried out under the following conditions.

As the chlorinating agent, there can be used thionyl chloride, phosgene (dimer), phosphorus pentachloride, phosphoryl chloride, chlorine, chlorosulfonic acid, etc.

As the solvent, there can be used DMF, formamide, chloroform, dichloromethane, carbon tetrachloride, 1,2-dichloroethane, etc.

The chlorinating agent is used in an amount of preferably 1 to 10 moles, more preferably 1 to 3 moles, per mole of the compound (II-3).

The reaction can be carried out preferably at 0° to 100° C., more preferably 0° to 25° C.

When the compound of the formula:

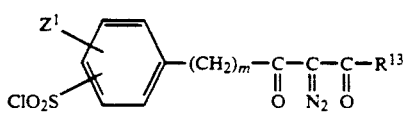
(II')

is subjected to hydrolysis, there can be obtained a compound of the formula:

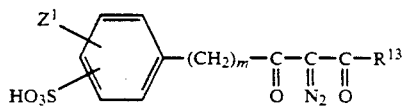
(II-5)

wherein $Z^1$, $R^{13}$ and m are as defined above.

When the compound of the formula (II') is subjected to alcoholysis in place of hydrolysis, there can be obtained a compound of the formula:

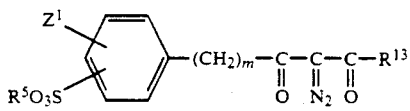
(II-6)

wherein $Z^1$, $R^5$, $R^{13}$ and m are as defined above.

When the compound of the formula (II') is reacted with ammonia, an aliphatic amine, or an organic base, there can be obtained a compound of the formula:

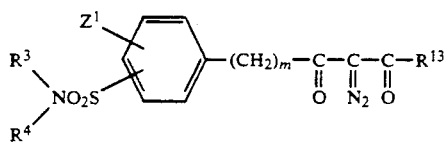
(II-7)

wherein $R^3$, $R^4$, $R^{13}$, $Z^1$ and m are as defined above.

Examples of the aliphatic amine are monomethylamine, monoethylamine, monopropylamine, monobutylamine, monopentylamine, dimethylamine, diethylamine, dipropylamine, monoethanolamine, diethanolamine, etc.

Examples of the organic base are piperidine, piperazine, pyrrolidine, morpholine, etc.

The compound of the formula (II-1) can be prepared by reacting an ester of the formula:

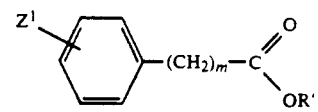

wherein $Z^1$ and m are as defined above; and R' is an alkyl group, with a ketone of the formula:

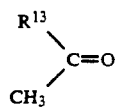

wherein $R^{13}$ is as defined above, in the presence of a condensing agent and preferably in a solvent.

As the condensing agent, there can be used Na, NaOR" (R" is an alkyl group), $NaNH_2$, KOR", $KNH_2$, $(C_6H_5)_3CNa$, etc.

As the solvent, there can be used an ether such as isopropyl ether, tetrahydrofuran, etc.; the ester per se, the ketone per se, a hydrocarbon, etc.

Alternatively, the compound of the formula (II-1) can be produced by reacting a ketone of the formula:

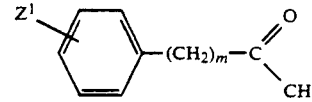

wherein $Z^1$ and m are as defined above, with an ester of the formula:

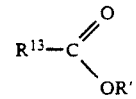

wherein $R^{13}$ and R' are as defined above, in the presence of a condensing agent, preferably in a solvent.

As the condensing agent and the solvent, those mentioned above can also be used.

The compound of the formula (III), wherein $X^1$ is a hydrogen atom, a halogen atom, a lower alkyl group or a lower alkoxy group (=$Z^1$) and $Y^1$ is $-SO_2Cl$, that is, the compound of the formula:

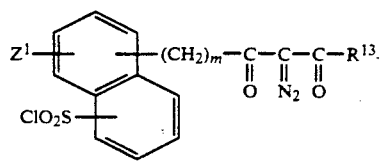
(III')

wherein $Z^1$, $R^{13}$ and m are as defined above, can be produced by reacting a compound of the formula:

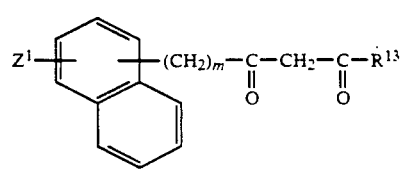
(III-1)

wherein $Z^1$, $R^{13}$ and m are as defined above with a diazotizing agent in the presence of a base to yield a compound of the formula:

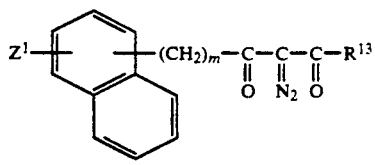
(III-4)

wherein $Z^1$, $R^{13}$ and m are as defined above, followed by a reaction with chlorosulfonic acid.

The diazotization and the chlorosulfonation can be carried out in the same manner as described in the case of the compound of the formula (II').

The compound of the formula (III') can also be produced by reacting a compound of the formula:

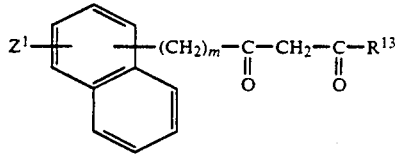
(III-1)

wherein $Z^1$, $R^{13}$ and m are as defined above, with a sulfonating agent, followed by neutralization to yield a compound of the formula:

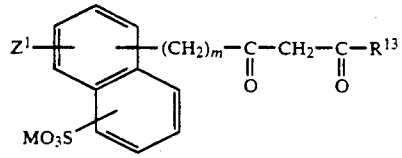
(III-2)

wherein $Z^1$, $R^{13}$, M and m are as defined above, reacting the compound of the formula (III-2) with a diazotizing agent in the present of a base to yield a compound of the formula:

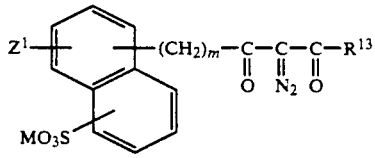
(III-3)

wherein M, $Z^1$, $R^{13}$ and m are as defined above, followed by reaction with a chlorinating agent.

The sulfonation, neutralization, diazotization and chlorination can be carried out in the same manner as described in the case of the compound of the formula (II').

The hydrolysis, the alcoholysis, and the reaction with ammonia, an aliphatic amine or an organic base of the compound of the formula (III'), can be carried out in the same manner as described in the case of the compound of the formula (II') to yield the following compounds:

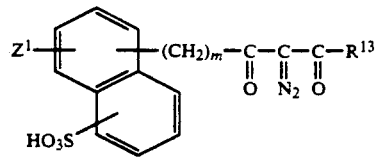
(III-5)

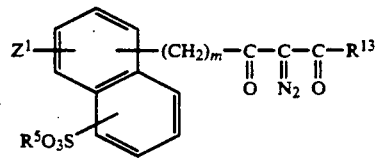
(III-6)

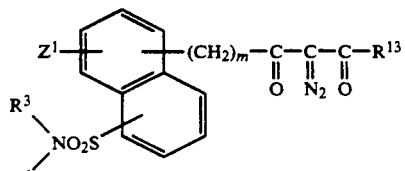
(III-7)

wherein $Z^1$, $R^3$, $R^4$, $R^5$, $R^{13}$ and m are as defined above.

In the formulae (III'), and (III-1) to (III-7), $Z^1$, $-SO_3M$, $-SO_2Cl$, $-SO_3H$, $-SO_3R^5$ and

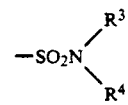

can be attached to any position of the naphthalene ring, that is, when the alkylene group is attached to the 1-position, $Z^1$, $-SO_3M$, $-SO_2Cl$, $-SO_3H$, $-SO_3R^5$ and

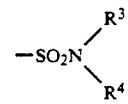

can be attached to any positions of 2- to 8-positions, or when the alkylene group is attached to the 2-position, $Z^1$, $-SO_3M$, $-SO_2Cl$, $-SO_3H$, $-SO_3R^5$ and

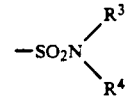

can be attached to any positions of 1-position and 3- to 8-positions.

The compound of the formula (III-1) can be prepared in the same manner as described in the case of the compound of the formula (II-1).

The compound of the formula (IV), wherein $X^1$ is a hydrogen atom, a halogen atom, a lower alkyl group or a lower alkoxy group ($=Z^1$), $X^2$ is a hydrogen atom, a halogen atom, a lower alkyl group or a lower alkoxy group ($=Z^2$), $Y^1$ is $-SO_2Cl$ and $Y^2$ is $-SO_2Cl$, that is, a compound of the formula:

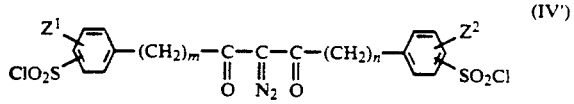 (IV')

wherein $Z^1$, $Z^2$, m and n are as defined above, can be produced by reacting a compound of the formula:

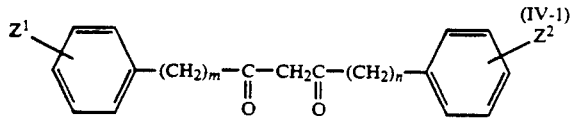 (IV-1)

wherein $Z^1$, $Z^2$, m and n are as defined above, with a diazotizing agent in the presence of an organic base to yield a compound of the formula:

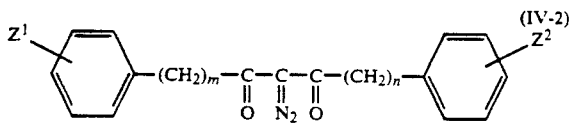 (IV-2)

wherein $Z^1$, $Z^2$, m and n are as defined above, followed by a reaction with chlorosulfonic acid.

The diazotization and the chlorosulfonation can be carried out in the same manner as described in the case of the compound of the formula (II'). In the chlorosulfonation, one of

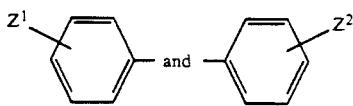

may be retained without attaching —SO$_2$Cl.

The compound of the formula (IV') can also be produced by reacting a compound of the formula:

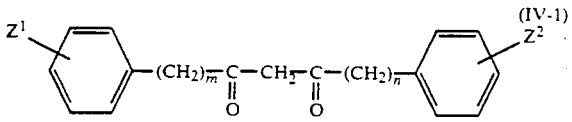 (IV-1)

wherein $Z^1$, $Z^2$, m and n are as defined above, with a sulfonating agent, followed by neutralization to yield a compound of the formula:

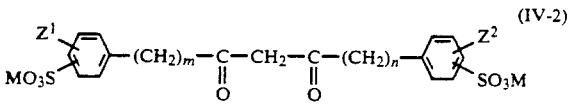 (IV-2)

wherein $Z^1$, $Z^2$, M, m and n are as defined above, reacting the compound of the formula (IV-2) with a diazotiting agent in the presence of an organic base to yield a compound of the formula:

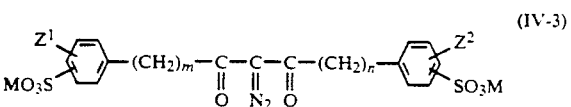 (IV-3)

wherein $Z^1$, $Z^2$, M, m and n are as defined above, followed by reaction with a chlorinating agent.

The sulfonation, neutralization, diazotization and chlorination can be carried out in the same manner as described in the case of the compound of the formula (II'). In the above-mentioned reactions, one of

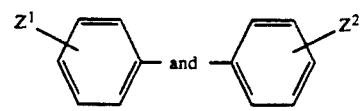

may be retained without attaching —SO$_2$Cl.

The hydrolysis, the alcoholysis, and the reaction with ammonia, an aliphatic amine or an organic base, of the compound of the formula (IV') can be carried out in the same manner as described in the case of the compound of the formula (II') to yield the following compounds:

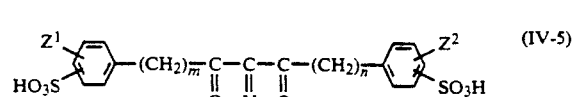 (IV-5)

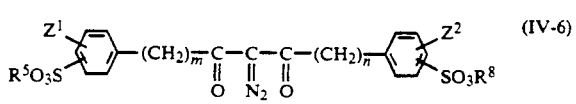 (IV-6)

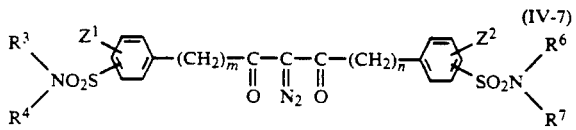 (IV-7)

wherein $Z^1$, $Z^2$, $R^3$, $R^4$, $R^5$, $R^6$, $R^7$, $R^8$, m and n are as defined above. In the above formulae (IV-5) to (IV-7), the following combinations may be possible;

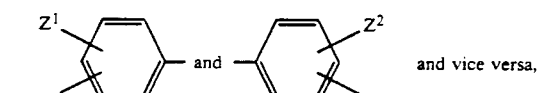 and vice versa,

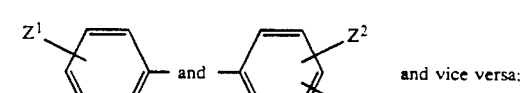 and vice versa;

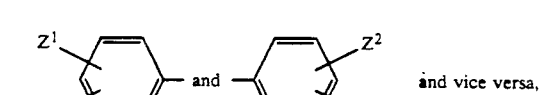 and vice versa,

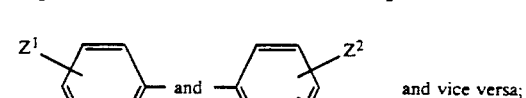 and vice versa;

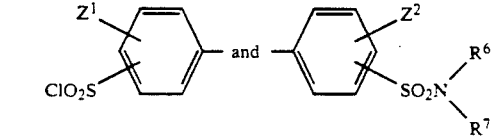

and vice versa.

-continued

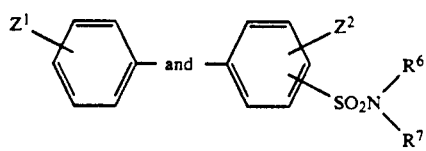

and vice versa.

The compound of the formula (IV-1) can be prepared in the same manner as described in the case of the compound of the formula (II-1). More concretely, a compound of the formula:

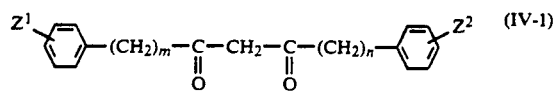

can be prepared by reacting compounds of the formula:

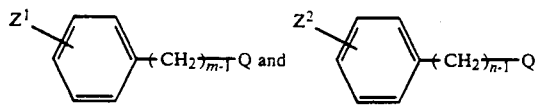

wherein $Z^1$, $Z^2$, m and n are as defined above; and Q is chlorine, bromine or iodine with 2,4-pentanedione in the presence of a condensing agent and a solvent at 10° C. or lower. As the condensing agent, there can be used n-butyllithium, lithium diisopropylamide, lithium, 1,1,1,3,3,3-hexamethyldisilazane, KH/n-BuLi, NaH/n-BuLi (Bu=butyl), etc. As the solvent, there can be used cyclohexane, n-hexane, toluene, isopropyl ether, etc.

The compound of the formula (IV-1) can also be prepared by reacting a ketone of the formula:

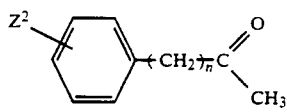

wherein $Z^2$ and m are as defined above, with an ester of the formula:

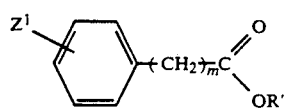

wherein R' is an alkyl group; and $Z^1$ and m are as defined above, in the presence of Na, NaH, or a metal alkoxide to carry out a condensation reaction.

The compound of the formula (V), wherein $X^1$ is a hydrogen atom, a halogen atom, a lower alkyl group or a lower alkoxy group ($=Z^1$); $X^2$ is a hydrogen atom, a halogen atom, a lower alkyl group or a lower alkoxy group ($=Z^2$); $Y^1$ is —SO$_2$Cl; and $Y^2$ is —SO$_2$Cl, that is, the compound of the formula:

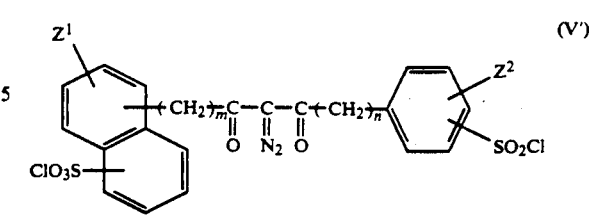

wherein $Z^1$, $Z^2$, m and n are as defined above, can be produced by reacting a compound of the formula:

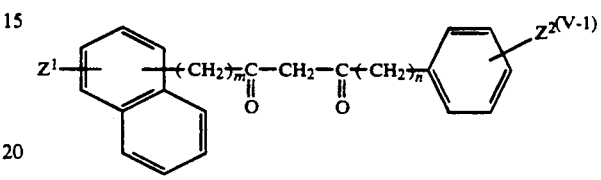

wherein $Z^1$, $Z^2$, m and n are as defined above, with a diazotizing agent in the presence of an organic base to yield a compound of the formula:

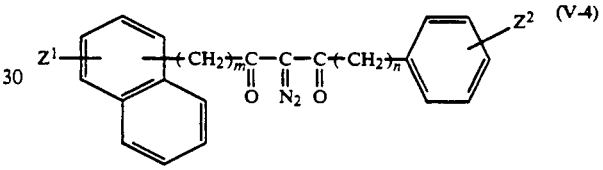

wherein $Z^1$, $Z^2$, m and n are as defined above, followed by a reaction with chlorosulfonic acid.

The diazotization and the chlorosulnation can be carried out in the same manner as described in the case of the compound of the formula (II').

The compound of the formula (V') can also be produced by reacting a compound of the formula:

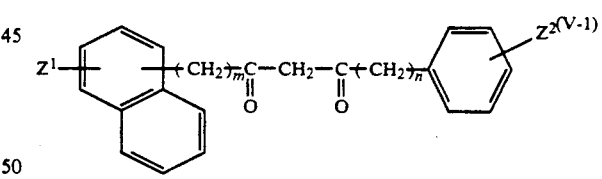

wherein $Z^1$, $Z^2$, m and n are as defined above, with a sulfonating agent, followed by neutralization to yield a compound of the formula:

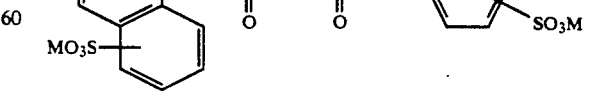

wherein $Z^1$, $Z^2$, M, m, and n are as defined above, reacting the compound of the formula (V-2) with a diazotizing agent in the presence of an organic base to yield a compound of the formula:

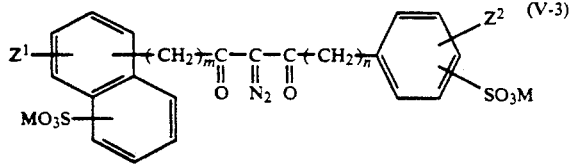

wherein $Z^1$, $Z^2$, M, m and n are as defined above, followed by reaction with a chlorinating agent.

The sulfonation, neutralization, diazotization and chlorination can be carried out in the same manner as described in the case of the compound of the formula (II').

The hydrolysis, the alcoholysis, and the reaction with ammonia, an aliphatic amine or an organic base, of the compound of the formula (V') can be carried out in the same manner as described in the case of the compound of the formula (II') to yield the following compounds:

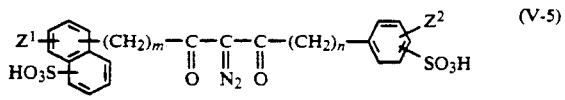

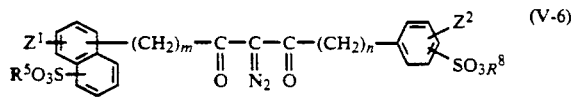

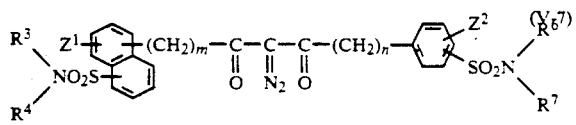

wherein $R^3$, $R^4$, $R^5$, $R^6$, $R^7$, $R^8$, $Z^1$, $Z^2$, m and n are as defined above.

In the formulae (V') and (V-1) to (V-7), $Z^1$, $-SO_3M$, $-SO_2Cl$, $-SO_3H$, $-SO_3R^5$, and

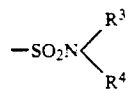

can be attached to any positions of the naphthalene ring, that is, when the alkylene group is attached to the 1-position, $Z^1$, $-SO_3M$, $-SO_2Cl$, $-SO_3H$, $-SO_3R^5$, and

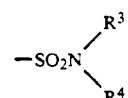

can be attached to any positions of 2- to 8-positions, or when the alkylene group is attached to the 2-position, $Z^1$ and the like substituents can be attached to any positions of 1-position and 3- to 8-positions.

The compound of the formula (V-1) can be prepared in the same manner as described in the case of the compound of the formula (IV-1).

The compound of the formula (VI), wherein $X^1$ is a hydrogen atom, a halogen atom, a lower alkyl group or a lower alkoxy group ($=Z^1$); $X^2$ is a hydrogen atom, a halogen atom, a lower alkyl group or a lower alkoxy group ($=Z^2$); $Y^1$ is $-SO_2Cl$; and $Y^2$ is $-SO_2Cl$, that is, the compound of the formula:

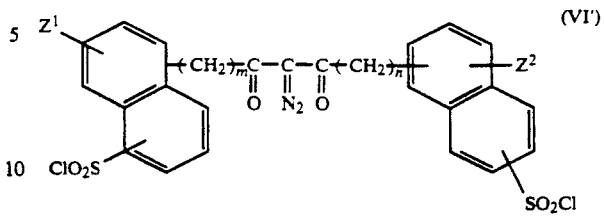

wherein $Z^1$, $Z^2$, m and n are as defined above, can be produced by reacting a compound of the formula:

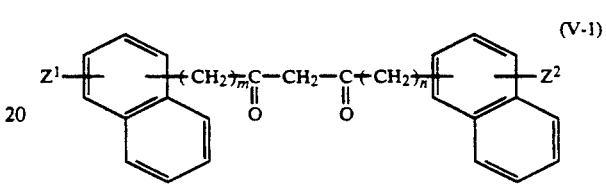

wherein $Z^1$, $Z^2$, m and n are as defined above, with a diazotizing agent in the presence of an organic base to yield a compound of the formula:

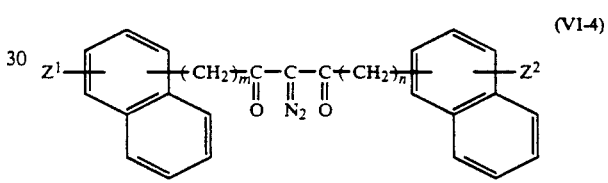

wherein $Z^1$, $Z^2$, m and n are as defined above, followed by a reaction with chlorosulfonic acid.

The diazotization and the chlorosulfonation can be carried out in the same manner as described in the case of the compound of the formula (II').

The compound of the formula (VI') can also be produced by reacting a compound of the formula:

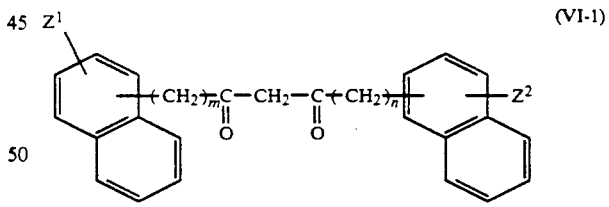

wherein $Z^1$, $Z^2$, m and n are as defined above, with a sulfonating agent, followed by neutralization to yield a compound of the formula:

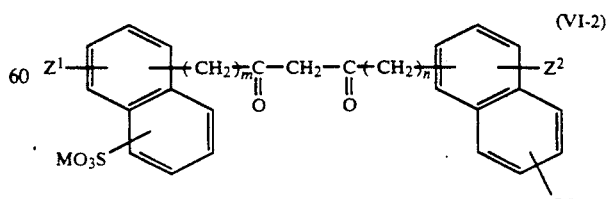

wherein $Z^1$, $Z^2$, M, m and n are as defined above, reacting the compound of the formula (VI-2) with a diazotizing agent in the presence of a base to yield a compound of the formula:

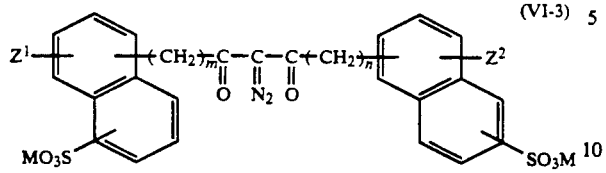
(VI-3)

wherein M, $Z^1$, $Z^2$, m and n are as defined above, followed by reaction with a chlorinating agent.

The sulfonation, neutralization, diazotization and chlorination can be carried out in the same manner as described in the case of the compound of the formula (II').

The hydrolysis, the alcoholysis, and the reaction with ammonia, an aliphatic amine or an organic base, of the compound of the formula (VI') can be carried out in the same manner as described in the case of the compound of the formula (II') to yield the following compounds:

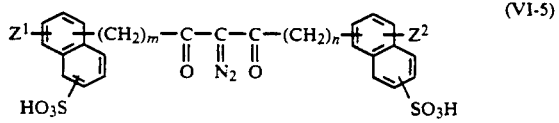
(VI-5)

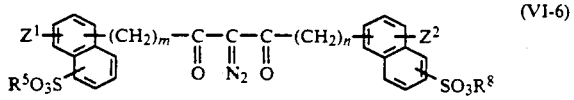
(VI-6)

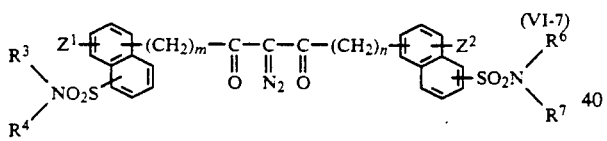
(VI-7)

wherein $Z^1$, $Z^2$, $R^3$, $R^4$, $R^5$, $R^6$, $R^7$, $R^8$, m and n are as defined above.

In the formulae (VI') and (VI-1) to (VI-7), $Z^1$, $Z^2$, —$SO_3M$, —$SO_2Cl$, —$SO_3H$, —$SO_3R^5$, —$SO_3R^8$,

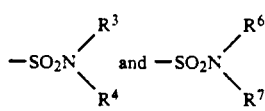

can be attached to any positions of the naphthalene ring, that is, when the alkylene group is attached to the 1-position, $Z^1$ and the like substituents can be attached to any positions of 2- to 8-positions, or when the alkylene group is attached to the 2-position, $Z^1$ and the like substituents can be attached to any positions of 1-position and 3- to 8-positions.

The compound of the formula (VI-1) can be prepared in the same manner as described in the case of the compound of the formula (IV-1).

The compound of the formula (VII), wherein $X^3$ is a hydrogen atom, a halogen atom, a lower alkyl group or a lower alkoxy group (=$Z^1$) and $Y^3$ is —$SO_2Cl$, that is, the compound of the formula:

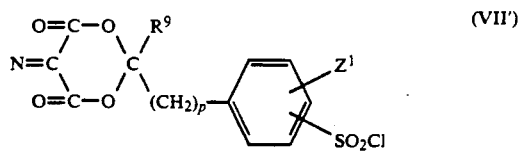
(VII')

wherein $Z^1$, $R^9$ and p are as defined above, can be produced by reacting a compound of the formula:

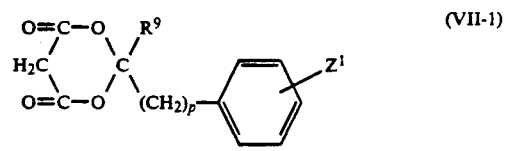
(VII-1)

wherein $Z^1$, $R^9$ and p are as defined above, with a diazotizing agent in the presence of an organic base to yield a compound of the formula:

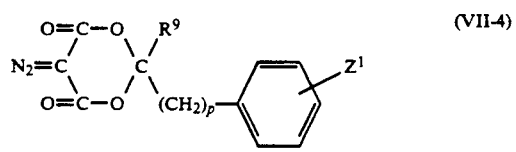
(VII-4)

wherein $Z^1$, $R^9$ and p are as defined above, followed by a reaction with chlorosulfonic acid.

The diazotization and the chlorosulfonatoin can be carried out in the same manner as described in the case of the compound of the formula (II').

The compound of the formula (VII') can also be produced by reacting a compound of the formula:

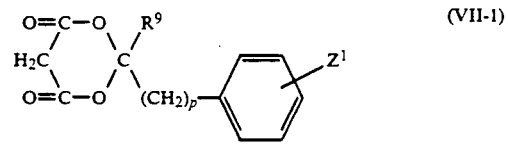
(VII-1)

wherein $Z^1$, $R^9$ and p are as defined above, with a sulfonating agent, followed by neutralization to yield a compound of the formula:

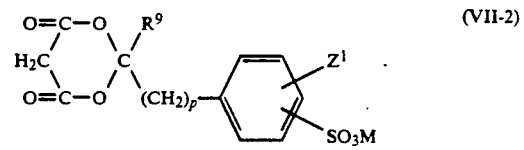
(VII-2)

wherein $R^1$, $R^9$, M, and p are as defined above, reacting the compound of the formula (VII-2) with a diazotizing agent in the presence of an organic base to yield a compound of the formula:

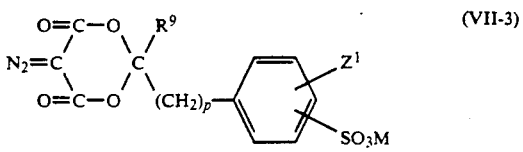
(VII-3)

wherein M, $Z^1$, $R^9$ and p are as defined above, followed by reaction with a chlorinating agent.

The sulfonation, neutralization, diazotization and chlorination can be carried out in the same manner as described in the case of the compound of the formula (II').

The hydrolysis, the alcoholysis, and the reaction with ammonia, an aliphatic amine or an organic base, of the compound of the formula (VII') can be carried out in the same manner as described in the case of the compound of the formula (II') to yield the following compounds:

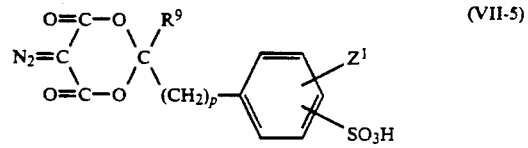
(VII-5)

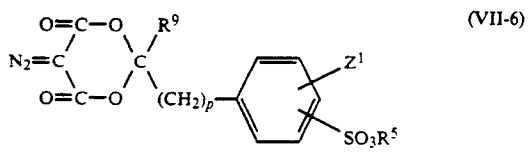
(VII-6)

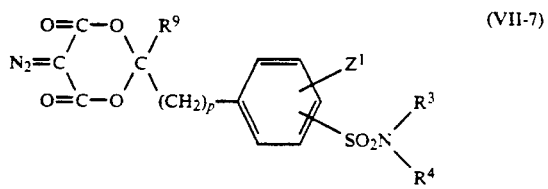
(VII-7)

wherein $R^3$, $R^4$, $R^5$, $R^9$, $Z^1$ and p are as defined above.

The compound of the formula (VII-1) can be prepared in the same manner as described in the case of the compound of the formula (II-1). More concretely, a compound of the formula:

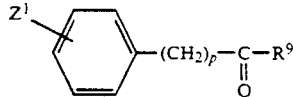

wherein $Z^1$, $R^9$ and p are as defined above, is reacted with malonic acid in the presence of acetic anhydride and sulfuric acid to form a compound of the formula:

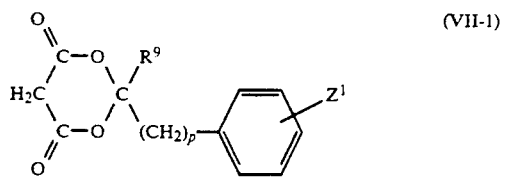
(VII-1)

The photosensitive compound of the formula (I) has a great reactivity against a light of 248.4 nm, that is, has a large change in light transmittance before and after exposure to the light (about 50% or more) and shows a transmittance of 65% or more after exposure to the light. Further, in a photosensitive composition comprising a compound of the formula (I) having a functional group such as —$SO_2Cl$, —$SO_3H$ or the like reactive with a resin as at least one of $X^1$, $X^2$, $X^3$, $Y^1$, $Y^2$ and $Y^3$, and a resin having OH groups, when heated after coating of the photosensitive composition, a crosslinking reaction proceeds, which results in producing an effect for decreasing a solubility of the resin in a developing solution. Thus, by using such a photosensitive composition as a resist or the like material, there can be obtained a resin pattern having a good (non-eroded) shape.

That is, the group of the formula:

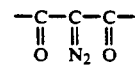

in the compound of the formula (I) is changed to a group of the formula:

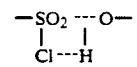
(VIII)

by deep UV light such as KrF excimer laser light, or the like. By the action of an alkaline aqueous solution, the group of the formula (VIII) changes as follows:

Thus, the photosensitive composition containing the photosensitive compound of the formula (I) becomes alkali-soluble in only light-exposed portions to form a so-called positive-type resist.

Generally speaking, a positive-type resist material is a combination of a photosensitive substance, a resin and a solvent. As the resin, an alkali-soluble novolac resin is mainly used. Therefore, it is desirable that alkali solubility of non-light exposed portions of novolac resin is suppressed.

In the compound of the formula [I] having one or more functional groups reactive with the resin as at least one of $X^1$, $X^2$, $X^3$, $Y^1$, $Y^2$ and $Y^3$, since there are one or more functional groups such as —$SO_2Cl$, —$SO_2Br$ or —$SO_3H$, at terminal groups, crosslinking proceeds with heating by forming, for example, ester bonds such as

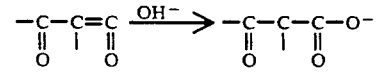

with —OH groups which are alkali-soluble portions of the resin, which results in suppressing alkali-solubility of the resin. Therefore, when the photosensitive composition of the present invention is used, the problem of erosion of retaining portions of resist film on the unexposed portions can be improved greatly.

Further, since the photosensitive compound of the formula (I) has one or two methylene chains such as —$(CH_2)_m$— in the molecule, the molecule as a whole is stabilized, which results in improving thermal stability of the compound of the formula (I). This also makes it possible to produce the compound of the formula (I) in indistrially large amounts and to store the compound of the formula (I) stably for a long period of time.

In the compound of the formula (I), the position of functional group such as —$SO_2Cl$,

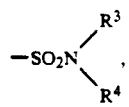

—SO$_3$H, —SO$_3$R$^5$, or the like can be any one of o-, m- and p-position of a benzene ring with regard to the methylene group, or can be any one of 2- to 8-positions when the methylene group is attached to the 1-position of a naphthalene ring or any one of 1-position and 3- to 8-positions when the methylene group is attached to the 2-position of the naphthalene ring. In any cases, the effect as a photosensitizer is not influenced considerably. As to the length of the methylene group, the effect is not so influenced when m, n and p are in the range of 1 to 20. Generally speaking, when the methylene group chain becomes longer, there is a tendency to attain the same effect with a smaller amount and the solubility of the photosensitive compound of the formula (I) per se in a developing solution is lowered. From this point of view, the longer the methylene group chain becomes, the better the results become.

The photosensitive compound of the formula (I) can be used not only in the production of semiconductor devices but also as a photosensitive reagent in the production of photoengraved plates, printing materials and the like applying the light reaction.

The present invention is illustrated by way of the following Examples, in which all percents are by weight unless otherwise specified.

EXAMPLE 1

Synthesis of p-toluenesulfonyl azide

Sodium azide (22.5 g, 0.35 mol) was dissolved in H$_2$O (65 ml) and diluted with 90% aqueous ethanol (130 ml). To this mixture, a solution of p-toluenesulfonyl chloride (60 g, 0.32 mol) in ethanol (300 ml) was added dropwise at 10°–25° C. and stirring was continued for 2.5 hours at room temperature. The reaction mixture was evaporated under reduced pressure, the resultant residue was washed with H$_2$O for several times, dried over anhydrous MgSO$_4$ and filtered with suction to give the title compound as a colorless oil; yield: 50.7 g.

$^1$HNMR δppm (CDCl$_3$): 2.43 (3H, s, CH$_3$), 7.24 (2H, d, J=8 Hz, Ar3-H, 5-H), 7.67 (2H, d, J=8 Hz, Ar 2-H, 6-H).

IR (Neat) νcm$^{-1}$: 2120.

EXAMPLE 2

Synthesis of 1-(4-chlorosulfonylphenyl)-3-diazo-2,4-pentanedione (Compound [III]; R$^{13}$=—CH$_3$, X$^1$=—SO$_2$Cl, Y$^1$=H, m=1)

(1) Synthesis of 1-phenyl-2,4-pentanedione

Sodium (28 g) was added in small portions to a solution of ethyl phenyl acetate (600 g, 3.66 moles) and acetone (70.7 g, 1.22 moles) under nitrogen, was dissolved at 30°–40° C. with stirring for 1 h and then the mixture was reacted at 70°–80° C. for 4.5 h. The reaction mixture was taken up in H$_2$O (1.2 l), neutralized with dilute hydrochloric acid and extracted with chloroform. The organic layer was washed with H$_2$O, dried over anhydrous MgSO$_4$ and then evaporated. The residue was distilled under reduced pressure to give the title compound as a colorless oil; yield: 53.2 g; bp 142°–146° C./15 mmHg. (Lit. bp 133°–136° C./10 mmHg; K. G. Hampton, T. M. Harris, C. R. Hauser, Org. Synth., 51, 128 (1971)).

(2) Synthesis of 3-diazo-1-phenyl-2,4-pentadione

To a solution of 1-phenyl-2,4-pentadione (36.2 g, 0.21 mol) obtained in above (1) and piperidine (17.5 g, 0.21 mol) in dichloromethane (500 ml), p-toluenesulfonyl azide (44.5 g, 0.23 mol) obtained in Example 1 was added dropwise at 0°–5° C., and stirring was continued for 1 h at the same temperature. The reaction mixture was washed with dilute aqueous potassium hydroxide and H$_2$O, dried over anhydrous MgSO$_4$ and evaporated in vacuo. The resultant residue (50 g) was chromatographed on silica gel (Wako Gel C-200, manufactured by Wako Pure Chemical Industries, LTd.) with n-hexane/ethyl acetate (10:1) as eluent to give the title compound as a orange-red viscous oil; yield: 33.0 g.

$^1$HNMR δppm (CDCl$_3$): 2.36 (3H, S, CH$_3$), 4.00 (2H, s, —CH$_2$—), 7.23 (5H, s, ArH).

IR (Neat) νcm$^{-1}$: 2140, 1660.

(3) Synthesis of 1-(4-chlorosulfonylphenyl)-3-diazo-2,4-pentanedione (Compound [II]; R$^{13}$=—CH$_3$, X$^1$=—SO$_2$Cl, Y$^1$=H, m=1)

To a solution of 3-diazo-1-phenyl-2,4-pentanedione (16.5 g, 0.082 mol) obtained in above (2) in chloroform (50 ml), chlorosulfonic acid (38 g) was added dropwise at −15° ~ −10° C. The mixture was stirred for 2 h at −15° ~ −10° C. and for 3 h at 10°–15° C., then poured into cold H$_2$O (1.5 l), and extracted with chloroform. The organic extract was washed with H$_2$O, dried over anhydrous MgSO$_4$, and then evaporated under reduced pressure. The resultant residue (20 g) was chromatographed on silica gel (Wako Gel C-200, manufactured by Wako Pure Chemical Industries, Ltd.) with n-hexane/ethyl acetate (5:1) as eluent to give the title compound as a yellow prisms after recrystallization from ethyl ether; yield: 4.0 g; mp 84.0°–86.5° C. (dec).

$^1$HNMR δppm (CDCl$_3$): 2.45 (3H, s, CH$_3$), 4.30 (2H, s, —CH$_2$—), 7.54 (2H, d, J=8 Hz, Ar2-H, 6-H), 8.00 (2H, d, J=8 Hz, Ar3-H, 5-H).

IR (KBr) νcm$^{-1}$: 2125, 1660.

UV (CH$_3$CN) λ$_{max}$ nm (logε): 244.2 (4.40).

Anal. calcd. for C$_{11}$H$_9$ClN$_2$O$_4$S: C%, 43.94; H%, 3.02; N%, 9.32. Found: C%, 44.02; H%, 3.14; N%, 9.30.

EXAMPLE 3

Synthesis of 6-(4-chlorosulfonylphenyl)-3-diazo-2,4-hexanedione (Compound [II]; R$^{13}$=—CH$_3$, X$^1$=—SO$_2$Cl, Y$^1$=H, m=2)

(1) Synthesis of 6-phenyl-2,4-hexanedione

Sodium (23 g) was added in small portions to a solution of 4-phenyl-2-butanone (148 g, 1 mol) and ethyl acetate (264 g) at 20°–60° C. with stirring under nitrogen and then the reaction mixture was refluxed for 2 h with stirring. After cooling, the mixture was taken up in H$_2$O (1l), neutralized with hydrochloric acid, the organic layer was separated, washed with H$_2$O, dried over anhydrous Na$_2$SO$_4$ and then evaporated. The resultant residue (171 g) was distilled under reduced pressure to give the title compound as a colorless oil; yield: 73.4 g; bp 128°–133° C./3–4 mmHg (Lit. bp 133°–136°

C./5 mmHg; C. R. Hauser, T. M. Harris, J. Am. Chem. Soc., 80, 6360 (1958)).

(2) Synthesis of 3-diazo-6-phenyl-2,4-hexanedione

Using 6-phenyl-2,4-hexanedione (29.0 g, 0.15 mol) obtained in above (1), the reaction was carried out in the same manner as described in Example 2, (2) to give the title compound as a orange-red amorphous solid; yield: 27.0 g; mp 30.0°-32.0° C.

$^1$HNMR δppm (CDCl$_3$): 2.47 (3H, s, CH$_3$), 3.10 (4H, s, —CH$_2$—CH$_2$—), 7.28 (5H, s, ArH).

IR (Neat) νcm$^{-1}$: 2100, 1650.

UV (CH$_3$CN) λ$_{max}$ nm (log ε): 229.3 (4.27).

(3) Synthesis of 6-(4-chlorosulfonylphenyl)-3-diazo-2,4-hexanedione (Compound [II]; $R^{13}$=—CH$_3$, $X^1$=—SO$_2$Cl, $Y^1$=H, m=2)

Using 3-diazo-6-phenyl-2,4-hexanedione (10.8 g, 0.05 mol) obtained in above (2), the reaction was carried out in the same manner as described in Example 2, (3) to give the title compound as a pale yellow amorphous solid; yield: 3.0 g; mp 58.0°-59.5° C.

$^1$HNMR δppm (CDCl$_3$): 2.40 (3H, s, CH$_3$), 3.20 (4H, s, —CH$_2$—CH$_2$—CO—), 7.32 (2H, dd, J=8 Hz, Ar2-H, 6-H), 7.97 (2H, dd, J=8 Hz, Ar3-H, 5-H).

IR (Neat) νcm$^{-1}$: 2130, 1660.

UV (CH$_3$CN) λ$_{max}$ nm (log ε): 244.2 (4.36).

Anal calcd. for C$_{12}$H$_{11}$ClN$_2$O$_4$S: C%, 45.65; H%, 3.51; N%, 8.87. Found: C%, 45.69; H%, 3.79; N%, 8.68.

EXAMPLE 4

Synthesis of 4-(4-diazo-3,5-dioxohexyl)benzenesulfonic acid (Compound [II]; $R^{13}$=—CH$_3$, $X^1$=—SO$_3$H, $Y^1$=H, m=2)

6-(4-Chlorosulfonylphenyl)-3-diazo-2,4-hexanedione (2.0 g; 6.4 mmol) obtained in Example 3, (3) was stirred in a solution of acetonitrile (15 ml) and H$_2$O (45 ml) for 2 h at 30°-35° C. The reaction mixture was washed with dichloromethane (40 ml×2) and then the aqueous layer was evaporated to dryness under reduced pressure to give the title compound as a slightly yellow viscous oil; yield: 1.4 g.

$^1$HNMR δppm (CDCl$_3$-DMSO-d$_6$): 2.37 (3H, s, CH$_3$), 2.88 (2H, t, J=7 Hz, —CH$_2$—CO—), 3.07 (2H, t, J=7 Hz, —CH$_2$—CH$_2$—CO—), 7.21 (2H, d, J=8.5 Hz, Ar3-H, 5-H), 7.58 (2H, d, J=8.5 Hz, Ar2-H, 6-H), 10.53 (1H, bs, —SO$_3$H).

IR (Neat) νcm$^{-1}$: 3370, 2120, 1630.

UV (CH$_3$CN) λ$_{max}$ nm (log ε): 226.4 (4.46).

Anal. calcd. for C$_{12}$H$_{12}$N$_2$O$_5$S: C%, 48.64; H%, 4.08; N%, 9.45. Found: C%, 48.75; H%, 4.11; N%, 9.29.

EXAMPLE 5

Synthesis of ammonium 4-(4-diazo-3,5-dioxohexyl) benzenesulfonate (Compound [II], $R^{13}$=—CH$_3$, $X^1$=—SO$_3$⊖N⊕H$_4$, $Y^1$=H, m=2)

To a solution of 4-(4-diazo-3,5-dioxohexyl)benzenesulfonic acid (890 mg, 30 mmol) obtained in Example 4 in acetonitrile (5 ml), 28% aqueous ammonia (3 ml) was added dropwise at 5°-10° C., and stirring was continued for 2 h at the same temperature. Then the mixture was evaporated under reduced pressure, and the residue was crystallized on treatment with acetonitrile to give the title compound as a white amorphous solid; yield: 750 mg; mp 81° C. (dec.).

$^1$HNMR δppm (CDCl$_3$-DMSO-d$_6$): 2.40 (3H, s, —CO—CH$_3$), 2.93 (1H, t, J=8 Hz, —CH$_2$—CO—), 3.06 (2H, t, 8 Hz, —CH$_2$CH$_2$—CO—), 3.34 (4H, bs, —N⊕H$_4$), 7.20 (2H, d, J=8 Hz, Ar3-H, 5-H), 7.70 (2H, d, J=8 Hz, Ar2-H, 6-H).

IR (KBr) νcm$^{-1}$: 3430, 2120, 1640.

UV (H$_2$O) λ$_{max}$ nm (log ε): 225.0 (4.36).

EXAMPLE 6

Synthesis of triethylammonium 4-(4-diazo-3,5-dioxohexyl) benzenesulfonate (Compound [II]; $R^{13}$=—CH$_3$, $X^1$=—SO$_3$⊖N⊕H(C$_2$H$_5$)$_3$, $Y^1$=H, m=2)

To a solution of 4-(4-diazo-3,5-dioxohexyl)benzenesulfonic acid (890 mg, 30 mmol) obtained in Example 4 in acetonitrile (5 ml), triethylamine (3 ml) was added dropwise at 5°-10° C., and stirring was continued for 2 h at the same temperature. Then the mixture was evaporated under reduced pressure, the residue was washed thrice with ethyl ether and evaporated to dryness under reduced pressure to give the title compound as a slightly yellow viscous oil; yield: 700 mg.

$^1$HNMR δppm (CDCl$_3$): 1.36 (9H, t, J=7 Hz, N—CH$_2$CH$_3$×3), 2.42 (3H, s, —CO—CH$_3$), 2.96-3.06 (4H, m, —CH$_2$CH$_2$—), 3.16 (6H, q, J=7 Hz, N—CH$_2$CH$_3$×3), 7.24 (2H, d, J=8 Hz, Ar3-H, 5-H), 7.81 (2H, d, J=8 Hz, Ar2-H, 6-H).

IR (Neat) νcm$^{-1}$: 3430, 2120, 1650.

UV (CH$_3$CN) λ$_{max}$ nm (log ε): 226.4 (4.37).

Anal. calcd. for C$_{18}$H$_{27}$N$_3$O$_5$S: C%, 54.39; H% 6.85; N%, 10.57. Found: C%, 54.11; H%, 7.14; N%, 10.36.

EXAMPLE 7

Synthesis of methyl 4-(4-diazo-3,5-dioxohexyl)benzenesulfonate (Compound [II]; $R^{13}$=—CH$_3$, $X^1$=—SO$_3$CH$_3$, $Y^1$=H, m=2)

6-(4-Chlorosulfonylphenyl)-3-diazo-2,4-hexanedione (2.0 g, 6.4 mmol) obtained in Example 3, (3) was stirred in triethylamine (1.5 ml), methanol (2.5 ml) and chloroform (8 ml) for 6 h at 10°-15° C., then the mixture was poured into H$_2$O and extracted thrice with chloroform. The organic extract was washed with H$_2$O, dried over anhydrous MgSO$_4$ and evaporated under reduced pressure. The residue was chromatographed on silica gel (Wako Gel C-200, manufactured by Wako Pure Chemical Industries, Ltd.) with chloroform as eluent to give the title compound as a pale yellow viscous oil; yield: 730 mg.

$^1$HNMR δppm (CDCl$_3$): 2.42 (3H, s, CH$_3$), 3.03-3.18 (4H, m, —CH$_2$CH$_2$—), 3.76 (3H, s, SO$_3$CH$_3$), 7.43 (2H, d, J=8.5 Hz, Ar3-H, 5-H), 7.83 (2H, d, J=8.5 Hz, Ar2-H, 6-H).

IR (Neat) νcm$^{-1}$: 2100, 1650.

UV (CH$_3$CN) λ$_{max}$ nm (log ε): 227.8 (4.48).

Anal. calcd. for C$_{13}$H$_{14}$N$_2$O$_5$S: C%, 50.32; H%, 4.55; N%, 9.03. Found: C%, 50.25, H%, 4.61; N%, 8.97.

EXAMPLE 8

Synthesis of ethyl 4-(4-diazo-3,5-dioxohexyl)benzenesulfonate (Compound [II], $R^{13}$=—CH$_3$, $X^1$=—SO$_3$C$_2$H$_5$, $Y^1$=H, m=2)

6-(4-Chlorosulfonylphenyl)-3-diazo-2,4-hexanedione (2.0 g, 6.4 mmol) obtained in Example 3, (3) was stirred in triethylamine (1.5 ml) and ethanol (5 ml) for 16 h at room temperature, then the mixture was poured into H$_2$O and extracted thrice with chloroform. The organic extract was washed with H$_2$O, dried over anhydrous MgSO$_4$ and evaporated under reduced pressure. The residue was chromatographed on silica gel (Wako Gel C-200) with chloroform as eluent to give the title compound as a pale yellow viscous oil; yield: 550 mg.

$^1$HNMR δppm (CDCl$_3$): 1.31 (3H, t, J=7 Hz, —SO$_2$CH$_2$CH$_3$), 2.42 (3H, s, —COCH$_3$), 3.04–3.17 (4H, m, Ar—CH$_2$CH$_2$CO—), 4.11 (2H, q, J=7 Hz, —SO$_3$CH$_2$CH$_3$), 7.42 (2H, d, J=8.5 Hz, Ar3-H, 5-H), 7.82 (2H, d, J=8.5 Hz, Ar2=H, 6-H).

IR (Neat) υcm$^{-1}$: 2120, 1645.

UV (CH$_3$CN) λ$_{max}$ nm (log ε): 229.0 (4.46).

Anal. calcd. for C$_{14}$H$_{16}$N$_2$O$_5$S: C%, 51.84; H%, 4.97; N%, 8.64. Found: C%, 51.77; H%, 4.85; N%, 8.73.

EXAMPLE 9

Synthesis of 6-(4-aminosulfonylphenyl)-3-diazo-2,4-hexanedione (Compound [II]; R$^{13}$=—CH$_3$, X$^1$=—SO$_2$NH$_2$, Y$^1$=H, m=2)

To a solution of 6-(4-chlorosulfonylphenyl)-3-diazo-2,4-hexanedione (1.0 g, 3.2 mmol) obtained in Example 3, (3) in acetonitrile (5 ml), 28% aqueous ammonia (2 g) was added dropwise at 5°–10° C., and stirring was continued for 6 h at room temperature. Then the mixture was evaporated under reduced pressure and the residue was chromatographed on silica gel (Wako Gel C-200; manufactured by Wako Pure Chemical Industries, Ltd.) with n-hexane/ethyl acetate (from 5:1 to 2:1) as eluent to give the title compound as a white amorphous solid; yield: 800 mg; mp 109.5°–111.5° C.

$^1$HNMR δppm (CDCl$_3$-DMSO-d$_6$): 2.41 (3H, s, COCH$_3$), 3.02–3.13 (4H, m, —CH$_2$CH$_2$—), 6.42 (2H, bs, —NH$_2$), 7.35 (2H, d, J=8 Hz, phenyl-C$_2$, C$_6$), 7.83 (2H, d, J=8 Hz, phenyl-C$_3$, C$_5$).

IR (KBr) υcm$^{-1}$: 2120, 1625.

UV (CH$_3$CN) λ$_{max}$ nm (log ε): 228.8 (4.47).

Anal. calcd. for C$_{12}$H$_{13}$N$_3$O$_4$S: C%, 48.80; H%, 4.44; N%, 14.23. Found: C%, 48.69; H%, 4.39; N%, 14.41.

EXAMPLE 10

Synthesis of 6-(4-N,N-diethylaminosulfonylphenyl)-3-diazo-2,4-hexanedione (Compound [II]; R$^{13}$=—CH$_3$, X$^1$=—SO$_2$N(C$_2$H$_5$)$_2$, Y$^1$=H, m=2)

Using 6-(4-chlorosulfonylphenyl)-3-diazo-2,4-hexanedione (1.0 g, 3.2 mmol) obtained in Example 3, (3) and diethylamine (0.6 g), the reaction was carried out in the same manner as described in Example 9 to give the title compound as a slightly yellow viscous oil; yield; 770 mg.

$^1$HNMR δppm (CDCl$_3$): 1.13 (6H, t, J=7 Hz, N—CH$_2$CH$_3$×2), 2.42 (3H, s, —COCH$_3$), 3.00–3.15 (4H, m, —CH$_2$CH$_2$CO—), 3.23 (4H, q, J=7 Hz, N—CH$_2$CH$_3$×2), 7.35 (2H, d, J=8.5 Hz, Ar3-H, 5-H), 7.72 (2H, d, J=8.5 Hz, Ar2-H, 6-H).

IR (Neat) υcm$^{-1}$: 2110, 1640.

UV (CH$_3$CN) λ$_{max}$ nm (log ε): 232.5 (4.28).

Anal. calcd. for C$_{16}$H$_{21}$N$_3$O$_4$S: C%, 54.69; H%, 6.02; N%, 11.96. Found: C%, 54.60; H%, 5.86; N%, 12.11.

EXAMPLE 11

Synthesis of 6-(4-morpholinosulfonylphenyl)-3-diazo-2,4-hexanedione (Compound [II]; R$^{13}$=—CH$_3$,

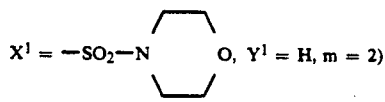

X$^1$ = —SO$_2$—N⟨O⟩, Y$^1$ = H, m = 2)

Using 6-(4-chlorosulfonylphenyl)-3-diazo-2,4-hexanedione (1.0 g, 3.2 mmol) obtained in Example 3, (3) and morpholine (0.83 g), the reaction was carried out in the same manner as described in Example 9 to give the title compound as a slightly yellow viscous oil; yield: 800 mg.

$^1$HNMR δppm (CDCl$_3$): 2.42 (3H, s, —COCH$_3$), 2.99 (4H, t, J=5 Hz, morpholine 2-H, 2-H, 6-H, 6-H), (3.04–3.16 (4H, m, —CH$_2$CH$_2$CO—), 3.74 (4H, t, J=5 Hz, morpholine 3-H, 3-H, 5-H, 5-H), 7.43 (2H, d, J=8 Hz, Ar3-H, 5-H), 7.67 (2H, d, J=8 Hz, Ar2-H, 6-H).

IR (Neat) υcm$^{-1}$: 2130, 1645.

UV (CH$_3$CN) λ$_{max}$ nm (log ε): 230.9 (4.47). Anal. calcd. for C$_{16}$H$_{19}$N$_4$O$_5$S: C%, 52.59; H%, 5.24; N%, 11.50. Found: C%, 52.42; H%; 5.30; N%, 11.66.

EXAMPLE 12

Synthesis of 6-(4-piperidinosulfonylphenyl)-3-diazo-2,4-hexanedione (Compound [II]; R$^{13}$=—CH$_3$,

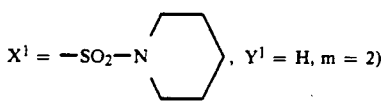

X$^1$ = —SO$_2$—N⟩, Y$^1$ = H, m = 2)

Using 6-(4-chlorosulfonylphenyl)-3-diazo-2,4-hexanedione (1.0 g, 3.2 mmol) obtained in Example 3, (3) and piperidine (0.65 g), the reaction was carried out in the same manner as described in Example 9 to give the title compound as a slightly yellow viscous oil; yield: 730 mg.

$^1$HNMR δppm (CDCl$_3$): 1.37–1.51 (2H, m, piperidine 4-H, 4-H), 1.60–1.74 (4H, m, piperidine 3-H, 3-H, 5-H, 5-H), 2.42 (3H, s, —COCH$_3$), 2.96–3.18 (8H, m, —CH$_2$CH$_2$CO— and and piperidine 2-H, 2-H, 6-H, 6-H), 7.38 (2H, d, J=8 Hz, Ar3-H, 5-H), 7.67 (2H, d, J=8 Hz, Ar2=H, 6-H).

IR (Neat) υcm$^{-1}$: 2130, 1640.

UV (CH$_3$CN) λ$_{max}$ nm (log ε): 231.2 (4.46).

Anal. calcd. for C$_{17}$H$_{21}$N$_3$O$_4$S: C%, 56.18; H%, 5.82; N%, 11.56. Found: C%, 56.01; H%, 6.10; N%, 11.49.

EXAMPLE 13

Synthesis of 9-(4-chlorosulfonylphenyl)-3-diazo-2,4-nonanedione (Compound [II]; R$^{13}$=—CH$_3$, X$^1$=—SO$_2$Cl, Y$^1$=H, m=5)

(1) Synthesis of 4-phenylbutanol

To a suspension of lithium aluminum hydride (67.2 g) in dry tetrahydrofuran (2.5 l), a solution of 4-phenylbutyric acid (225 g, 1.37 mmoles) in dry tetrahydrofuran was added dropwise at 15°–25° C. under nitrogen. The resultant mixture was stirred for 1 h at room temperature, then poured into ice-cold H$_2$O (3 l) and sulfuric acid (200 g) and extracted thrice with ethyl acetate. The organic extract was dried over anhydrous N$_2$SO$_4$, evaporated, and then the residue was distilled under reduced pressure to give the title compound as a colorless oil; yield: 191 g; bp 113°–115° C./0.5 mmHg (Lit. bp 92°–93° C./0.3 mmHg; B. H. Baker, W. B. Martin, J. Org. Chem., 25, 1496 (1960)).

(2) Synthesis of 1-chloro-4-phenylbutane

Thionyl chloride (300 g) was added dropwise in 4-phenylbutanol (189 g, 1.26 mols) obtained in above (1) at room temperature and stirring was continued for 4 h under reflux. The reaction mixture was evaporated and the resultant residue was distilled under reduced pressure to give the title compound as a colorless oil; yield: 149 g; bp 122°–123° C./17 mmHg (Lit. bp 90°–91° C./2 mmHg; A.Iliceto, A. Fava, A. Simeone, Gazz. chim, ital., 90, 600 (1960)).

(3) Synthesis of 9-phenyl-2,4-nonanedione

To a suspension of sodium hydride (60% in oil, 10.7 g) in dry cyclohexane (140 ml), a solution of 2,4-pentanedione (26.7 g, 0.267 mol) in dry cyclohexane was added dropwise at room temperature with stirring under nitrogen, and the resultant mixture was stirred for 2 h at the same temperature. To this suspension, N,N,N',N'-tetramethylethylenediamine (34.1 g) was added dropwise, followed by the dropwise addition of n-butyllithium (1.6M in n-hexane solution, 185 ml) at 0° C. or lower and the resultant mixture was stirred for 2 h at room temperature. Then to this suspension, 1-chloro-4-phenylbutane (52.3 g, 0.31 mol) obtained in above (2) was added dropwise at 0°–5° C. and stirring was continued for 3 h at room temperature. The reaction mixture was poured into ice-cold H$_2$O (1l), neutralized with dilute hydrochloric acid and extracted twice with ethyl acetate. The organic extract was washed with H$_2$O, dried over anhydrous MgSO$_4$ and solvent was removed. The residue was chromatographed on silica gel (Wako Gel C-200) with benzene/n-hexane (4:1) as eluent to give the title compound as a pale yellow oil which was an ca 1:6 mixture of Keto/Enol as seen by the methylene singlet at δ3.55 ppm and the methine singlet at δ5.47 ppm in the $^1$HNMR spectrum; yield: 8.5 g.

$^1$HNMR δppm (CDCl$_3$): 1.34–1.71 (6H, m, —CH$_2$CH$_2$CH$_2$—CH$_2$CO—), 2.04 (3H, s, —COCH$_3$), 2.26 (2H, t, J=8 Hz, —CH$_2$COCH$_2$CO—), 2.61 (2H, t, J=8 Hz, Ar—CH$_2$—), 3.55 (2H, s, —COCH$_2$CO—), 5.47

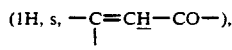
(1H, s, —C=CH—CO—), 7.16–7.30 (5H, m, ArH), 15.49 (1H, bs, —OH).
IR (Neat) νcm$^{-1}$: 1725, 1600.

(4) Synthesis of 3-diazo-9-phenyl-2,4-nonanedione

Using 9-phenyl-2,4-hexanedione (7.8 g, 0.034 mol) obtained in above (3) and triethylamine (3.4 g, 0.034 mol), the reaction was carried out in the same manner as described in Example 2, (2) and the crude product was purified by column chromatography on silica gel (Wako Gel C-200) eluting with n-hexane/dichloromethane (2:1→1:1→1:4) to afford the title compound as a yellow viscous oil; yield;5.2 g.

$^1$HNMR δppm (CDCl$_3$): 1.35–1.74 (6H, m, —CH$_2$CH$_2$CH$_2$—CH$_2$CO—), 2.43 (3H, s, —COCH$_3$), 2.61 (2H, t, J=8 Hz, Ar—CH$_2$—), 2.70 (2H, t, J=8 Hz, —CH$_2$CO—), 7.15–7.30 (5H, m, ArH).
IR (Neat) νcm$^{-1}$: 2100, 1650.

(5) Synthesis of 9-(4-chlorosulfonylphenyl)-3-diazo-2,4-nonanedione (Compound [II]; R$^{13}$=—CH$_3$, X$^1$=—SO$_2$Cl, Y$^1$=H, m=5)

Using 3-diazo-9-phenyl-2,4-nonanedione (3.6 g, 14 mmol) obtained in above (4), the reaction was carried out in the same manner as described in Example 2, (3) to give the title compound as a slightly yellow viscous oil; yield: 1.4 g.

$^1$HNMR δppm (CDCl$_3$): 1.37–1.75 (6H, m, —CH$_2$CH$_2$CH$_2$—CH$_2$CO—), 2.43 (3H, s, —COCH$_3$), 2.74 (4H, m, —CH$_2$—CO— and Ar—CH$_2$), 7.41 (2H, d, J=8 Hz, Ar2-H, 6-H), 7.95 (2H, g, J=8 Hz, Ar3-H, 5-H).
IR (Neat) νcm$^{-1}$: 2100, 1645.
UV (CH$_3$CN) λ$_{max}$ nm (log ε): 242.2 (4.27).
Anal Calcd. for C$_{15}$H$_{17}$ClN$_2$O$_4$S C%, 50.49; H%, 4.80; N%, 7.85. Found: C%; 50.63; H%, 4.69; N%, 7.77.

EXAMPLE 14

Synthesis of ethyl 4-(7-diazo-6,8-dioxononyl)benzenesulfonate (Compound [II]; R$^{13}$=—CH$_3$, X$^1$=—SO$_3$C$_2$H$_5$, Y$^1$=H, m=5)

Using 9-(4-chlorosulfonylphenyl)-3-diazo-2,4-nonanedione (1.1 g, 3.1 mmol) obtained in Example 13, (5), the reaction was carried out in the same manner as described in Example 8 and the crude oil was chromatographed on silica gel (Wako Gel C-200) with chloroform as eluent to give the title compound as a pale yellow viscous oil; yield: 850 mg.

$^1$HNMR δppm (CDCl$_3$): 1.23–1.34 (5H, m, —CH$_2$CH$_2$CH$_2$CO— and —SO$_3$CH$_2$CH$_3$), 1.59–1.64 (4H, m, Ar—CH$_2$CH$_2$— and —CH$_2$CH$_2$CO—), 2.36 (3H, s, —COCH$_3$), 2.60–2.69 (4H, m, Ar—CH$_2$— and —CH$_2$CO—), 4.04 (2H, q, J=7 Hz, —SO$_3$CH$_2$CH$_3$), 7.27 (2H, d, J=8 Hz, Ar2-H, 6-H), 7.73 (2H, d, J=8 Hz, Ar3-H, 5-H).
IR (Neat) νcm$^{-1}$: 2100, 1640.
Anal. calcd, for C$_{17}$H$_{22}$N$_2$O$_5$S: C%, 55.72; H%, 6.05; N%, 7.64. Found: C%, 55.61; H%, 6.21; N%, 7.88.

EXAMPLE 15

Synthesis of 1-(4-chlorosulfonylphenyl)-4-diazo-3,5-octanedione (Compound [II]; R$^{13}$=CH$_3$CH$_2$CH$_2$—, X$^1$=—SO$_2$Cl, Y$^1$=H, m=2)

(1) Synthesis of 1-phenyl-3,5-octanedione

Sodium (7.3 g) was added in small portions to a solution of 4-phenyl-2-butanone (46.8 g, 0.31 mol) and ethyl butyrate (110 g, 0.95 mol) in toluene (120 ml) at 20°–60° C. under nitrogen, and stirring was continued for 9 h under reflux. After standing overnight, the reaction mixture was taken up in H$_2$O (300 ml), neutralized with hydrochloric acid and extracted with ethyl acetate. The organic layer was washed with H$_2$O, dried over anhydrous MgSO$_4$ and then evaporated. The residual reddish orange oil (84 g) was distilled under reduced pressure to afford the title compound as a pale yellow oil which was an ca 3:7 mixture of Keto/Enol as seen by the methylene singlet at δ3.52 ppm and the methine singlet as δ5.45 ppm in the $^1$HNMR spectrum; yield: 15.4 g; bp. 166°–168° C./2 mmHg.

$^1$HNMR δppm (CDCl$_3$): 0.93 (3H, t, J=7 Hz, —CH$_3$), 1.53–1.67 (2H, m, —CH$_2$CH$_3$), 2.23 (2H, t, J=7 Hz, —CH$_2$CH$_2$CH$_3$), 2.60 (2H, t, J=7 Hz, Ar—CH$_2$CH$_2$—), 2.94 (2H, t, J=7 Hz, Ar—CH$_2$—), 3.52 (2H, s, —COCH$_2$CO—), 5.45

(1H, s, —C=CHCO—),
       |

7.16–7.28 (5H, m, ArH), 15.46 (1H, bs, OH).
IR (Neat) νcm$^{-1}$: 1600.

(2) Synthesis of 4-diazo-1-phenyl-3,5-octanedione

Using 1-phenyl-3,5-octanedione (7.6 g, 35 mmol) obtained in above (1), the reaction was carried out in the same manner as described in Example 3, (2), and the crude oil (12 g) was purified by column chromatography om silica gel (Wako Gel C-200) with n-hexane/dichloromethane (5:1→3:1→1:1) as eluent to give the title compound as a yellow oil; yield: 5.3 g.

$^1$HNMR δppm (CDCl$_3$): 0.97 (3H, t, J=7 Hz, CH$_3$), 1.63–1.77 (2H, m, —CH$_2$CH$_3$), 2.68 (2H, t, J=7 Hz, —CH$_2$CH$_2$CH$_3$), 2.94–3.11 (4H, m, A4-CH$_2$CH$_2$—), 7.19–7.33 (5H, m, ArH).
IR (Neat) νcm$^{-1}$: 2140, 1650.

(3) Synthesis of 1-(4-chlorosulfonylphenyl)-4-diazo-3,5-octanedione (Compound [II]; $R^{13}$=CH$_3$CH$_2$CH$_2$—, $X^1$=—SO$_2$Cl, $Y^1$=H, m=2)

Using 4-diazo-1-phenyl-3,5-octanedione (5.2 g, 21.3 mmol) obtained in above (2), the reaction was carried out in the same manner as described in Example 3, (3), and the crude oil (3 g) was chromatographed on silica gel (Wako Gel C-200, manufactured by Wako Pure Chemical Industries, Ltd.) with n-hexane/ethyl acetate (from 5:1 to 3:1) as eluent to give the title compound as a pale yellow viscous oil; yield: 900 mg.

$^1$HNMR δppm (CDCl$_3$): 0.98 (3H, t, J=7 Hz, —CH$_3$), 1.63–1.77 (2H, m, —CH$_2$CH$_3$), 2.63 (2H, t, J=7 Hz, —CH$_2$CH$_2$CH$_3$), 3.09 (2H, t, J=7 Hz, Ar—CH$_2$CH$_2$—), 3.22 (2H, t, J=7 Hz, Ar—CH$_2$—), 7.49 (2H, d, J=9 Hz, Ar2-H, 6-H), 7.95 (2H, d, J=9 Hz, Ar3-H, 5-H).
IR (Neat) νcm$^{-1}$: 2140, 1650.

Anal. calcd. for C$_{14}$H$_{15}$ClN$_2$O$_4$S: C%, 49.05; H%, 4.41; N%, 8.17. Found: C%, 48.89; H%, 4.66; N%, 8.34.

EXAMPLE 16

Synthesis of 6-(4-chlorosulfonylphenyl)-3-diazo-2,4-hexanedione (Compound [II]; $R^{13}$=—CH$_3$, $X^1$=—SO$_2$Cl, $Y^1$=H, m=2)

(1) Synthesis of potassium 4-(3,5-dioxohexyl)benzenesulfonate

To a suspension of 6-phenyl-2,4-hexanedione (15.2 g, 80 mmol) obtained in Example 3, (1) and tantalum powder (100 mg) in carbon tetrachloride (40 ml), chlorosulfonic acid (9.4 g, 80 mmol) was added dropwise at −5°~0° C., and stirring was continued for 30 min at the same temperature. After reaction, supernatant solvent was decanted, the residue was treated with cold H$_2$O (150 ml) and filtered to removed inorganic materials. Then to the filtrate, dilute aqueous potassium hydroxide was added, evaporated to dryness under reduced pressure and the residue was recrystallized from ethanol to give the title compound as a white prisms; yield: 16.0 g; mp 153° C. (dec.).

$^1$HNMR δppm (CDCl$_3$-DMSO-d$_6$): 2.01 (3H, s, CH$_3$), 2.54 (2H, t, J=7 Hz, —CH$_2$CH$_2$CO—), 2.85 (2H, t, J=7 Hz, Ar—CH$_2$—), 7.16 (2H, d, J=8 Hz, Ar2-H, 6-H), 7.62 (2H, d, J=8 Hz, Ar3-H, 5-H).
IR (KBr) νcm$^{-1}$: 1690.

(2) Synthesis of potassium 4-(4-diazo-3,5-dioxohexyl)benzenesulfonate

To a solution of potassium 4-(3,5-dioxohexyl)benzenesulfonate (15.4 g, 50 mmol) obtained in above (1) and triethylamine (5.7 g, 56 mmol) in N,N-dimethylformamide (100 ml) and dichloromethane (20 ml), p-toluenesulfonylazide (10.6 g, 54 mmol) obtained in Example 1 was added dropwise at 0°–5° C., and stirring was continued for 4 h at the same temperature. Then the reaction mixture was taken up in dichloromethane (400 ml), the resultant precipitate was filtered, washed thrice with dichloromethane and dried in vacuo to give the title compound as a pale yellow solid; yield: 12.5 g; mp 75° C. (dec.).

$^1$HNMR δppm (CDCl$_3$-DMSO-d$_6$) 2.38 (3H, s, CH$_3$), 2.89 (2H, t, J=7 Hz, —CH$_2$CH$_2$CO—), 3.06 (2H, t, J=7 Hz, Ar—CH$_2$—), 7.18 (2H, d, J=8 Hz, Ar2-H, 6-H), 7.63 (2H, d, J=8 Hz, Ar3-H, 5-H).
IR (KBr) νcm$^{-1}$: 2120, 1640.

(3) Synthesis of 6-(4-chlorosulfonylphenyl)-3-diazo-2,4-hexanedione (Compound [II]; $R^{13}$=—CH$_3$, $X^1$=—SO$_2$Cl, $Y^1$=H, m=2)

To a solution of potassium 4-(4-diazo-3,5-dioxohexyl)benzenesulfonate (11.7 g, 35 mmol) obtained in above (2) in N, N-dimethylformamide (40 ml), thionyl chloride (6.3 g, 53 mmol) was added dropwise at 10°–15° C., and stirring was continued for 2 h at room temperature. The reaction mixture was poured into cold H$_2$O (400 ml), extracted with chloroform, the organic layer was washed with H$_2$O, dried over anhydrous MgSO$_4$ and evaporated in vacuo. The resultant residue (6.5 g) was purified by column chromatography on silica gel (Wako Gel C-200, manufactured by Wako Pure Chemical Industries, Ltd.) with n-hexane/ethyl acetate (5:1) as eluent to give the title compound as a pale yellow viscous oil, which solidified rapidly to afford pale yellow solid; yield: 4.2 g; mp 58.0°–59.5° C.

$^1$HNMR, IR and UV spectra of this product were identical with those of the product as described in Example 3,(3).

EXAMPLE 17

Synthesis of 1,7-bis(4-chlorosulfonylphenyl)-4-diazo-3,5-heptanedione (Compound [IV]; $Y^1$=$Y^2$=H, $X^1$=$X^2$=—SO$_2$Cl, m=n=2)

(1) Synthesis of 1,7-diphenyl-3,5-heptanedione

To a suspension of sodium hydride (60% in oil, 17 g) in dry cyclohexane (200 ml), a solution of 2,4-pentanedione (37 g. 0.37 mol) in dry cyclohexane was added dropwise at room temperature with stirring under nitrogen, and the resultant mixture was stirred for 40 min at the same temperature. To this suspension, N,N,N',N'-tetramethylethylenediamine (91.8 g) was added dropwise, followed by the dropwise addition of n-butyllithium (1.6M in n-hexane solution, 337 g) at 0° C. or lower and the resultant mixture was stirred for 24 h at room temperature. Then to this suspension, benzyl chloride (93.7 g) was added dropwise at 0°-5° C., stirring was continued for 2 h at room temperature and standed for overnight. The reaction mixture was poured into dilute hydrochloric acid, the organic layer was separated, washed thrice with $H_2O$, dried over $MgSO_4$ and evaporated. The residue (79 g) was distilled under reduced pressure to give the title compound as a pale yellow oil; yield: 23.5 g; bp 185°-190° C./0.4 mmHg.

(2) Synthesis of 4-diazo-1,7-diphenyl-3,5-heptanedione

To a solution of 1,7-diphenyl-3,5-heptanedione (16.6 g, 60 mmol) obtained in above (1) and piperidine (5.1 g, 60 mmol) in dichloromethane (120 ml), p-toluenesulfonylazide (12.4 g, 63 mmol) obtained in Example 1 was added dropwise at 0°-5° C., and stirring was continued for 2 h at the same temperature. The reaction mixture was washed with dilute aqueous potassium hydroxide and $H_2O$, dried over anhydrous $MgSO_4$ and evaporated in vacuo. The resultant residue (19 g) was chromatographed on silica gel (Wako Gel C-200, manufactured by Wako Pure Chemical Industries, Ltd.) with dichloromethane as eluent to give the title compound as a slightly yellow crystals; yield: 8.0 g; mp 62.5°-64.0° C.

$^1$HNMR $\delta$ppm (CDCl$_3$): 2.93-3.08 (8H, m, —CH$_2$—×4), 720 (10H, s, ArH×2).

IR (KBr) $\nu$cm$^{-1}$: 2120, 1650.

UV (CH$_3$CN) $\lambda_{max}$ nm (log $\epsilon$): 231.0 (4.28).

(3) Synthesis of 1,7-bis(4-chlorosulfonylphenyl)-4-diazo-3,5-heptanedione (Compound [IV]; $Y^1=Y^2=H$, $X^1=X^2=-SO_2Cl$, m=n=2)

A solution of 4-diazo-1,7-diphenyl-3,5-heptanedione (7.5 g, 24 mmol) obtained in above (2) in chloroform was added dropwise into chlorosulfonic acid (22.4 g) at 0°-5° C., and stirring was continued for 1 h at the same temperature. The reaction mixture was poured into cold $H_2O$ (0.5 l), extracted with chloroform, the organic extract was washed with $H_2O$ for several times, dried over anhydrous $MgSO_4$ and evaporated in vacuo. The resultant residue (5 g) was chromatographed on silica gel (Wako Gel C-200, manufactured by Wako Pure Chemical Industries, Ltd.) with n-hexane/ethyl acetate (from 3:1 to 1:1) as eluent to give the title compound as yellow crystals; yield: 3.0 g; mp 121°-122.5° C.

$^1$HNMR $\delta$ppm (CDCl$_3$): 3.11 (8H, s, —CH$_2$—×4), 7.40 (4H, d, J=8 Hz, (Ar2-H, 6-H)×2), 7.53 (4H, d, J=8 Hz, (Ar3-H, 5-H)'2).

IR (KBr) $\nu$cm$^{-1}$: 2130, 1640.

UV (CH$_3$CN) $\lambda_{max}$ nm (log $\epsilon$): 245.6 (4.54).

Anal calcd. for $C_{19}H_{16}Cl_2N_2O_6S_2$: C%, 45.34; H%, 3.20; N%, 5.57. Found: C%, 45.25; H%, 3.36; N%, 5.56.

EXAMPLE 18

Synthesis of 4-diazo-1,7-bis(4-ethoxysulfonylphenyl-3,5-heptanedione (Compound [IV], $Y^1=Y^2=H$, $X^1=X^2=-SO_3C_2H_5$, m=n=2)

To a solution of 1,7-bis(4-chlorosulfonylphenyl)-4-diazo-3,5-heptanedione (700 mg, 1.4 mmol) obtained in Example 17, (3), in ethanol (15 ml) and dichloromethane (10 ml), triethylamine (420 mg) was added dropwise at 5°-10° C., and stirring was continued for 8 h at room temperature. The reaction mixture was concentrated under reduced pressure, diluted with dichloromethane (40 ml), washed thrice with $H_2O$, dried over anhydrous $MgSO_4$ and evaporated under reduced pressure. The resultant residue (820 mg) was chromatographed on silica gel (Wako Gel C-200) with n-hexane/ethyl acetate (from 5:1 to 3:1) as eluent to give the title compound as a slightly yellow viscous oil; yield: 450 mg.

$^1$HNMR $\delta$ppm (CDCl$_3$): 1.31 (6H, t, J=7 Hz, SO$_3$CH$_2$CH$_3$×2), 3.08 (8H, bs, Ar—CH$_2$CH$_2$CO—×2), 4.12 (4H, q, J=7 Hz, SO$_2$CH$_2$CH$_3$×2), 7.41 (4H, d, J=8 Hz, (Ar2-H, 6-H)×2), 7.83 (4H, d, J=8 Hz, (Ar 3-H, 5-H)×2).

IR (Neat) $\nu$cm$^{-1}$: 2130, 1650.

UV (CH$_3$CN) $\lambda_{max}$ nm (log $\epsilon$): 229.0 (4.62).

Anal. calcd. for $C_{23}H_{26}N_3O_8S_2$: C%, 52.86; H%, 5.01; N%, 5.36.

Found: C%, 52.65; H%, 5.21; N%, 5.31.

EXAMPLE 19

Synthesis of 4-diazo-1,7-bis(4-N,N-diethylaminosulfonylphenyl)-3,5-heptanedione (Compound [IV]; $Y^1=Y^2=H$, $X^1=X^2=-SO_2N(C_2H_5)_2$, m=n=2)

To a solution of 1,7-bis(4-chlorosulfonylphenyl)-4-diazo-3,5-heptanedione (700 mg, 1.4 mmol) obtained in Example 17, (3) in acetonitrile (15 ml), N,N-diethylamine (1 g) was added dropwise at 5°-10° C., and stirring was continued for 10 h at room temperature. The reaction mixture was concentrated under reduced pressure, diluted with methylenechloride (40 ml), washed thrice with $H_2O$, dried over anhydrous $MgSO_4$ and evaporated under reduced pressure. The resultant residue (800 mg) was chromatographed on silica gel (Wako Gel C-200) with n-hexane/ethyl acetate (from 5:1 to 3:1) as eluent to give the title compound as a slightly yellow viscous oil; yield: 370 mg.

$^1$HNMR $\delta$ppm (CDCl$_3$): 1.13 (12H, t, J=7 Hz, N—CH$_2$CH$_3$×4), 3.05 (8H, bs, —CH$_2$CH$_2$CO—×2), 3.23 (8H, q, J=7 Hz, N—CH$_2$CH$_3$×4), 7.34 (4H, d, J=8 Hz, (Ar2-H, 6-H)×2), 7.73 (4H, d, J=8 Hz, (Ar3-H, 5-H)×2).

IR (Neat) $\nu$cm$^{-1}$: 2120, 1650.

UV (CH$_3$CN) $\lambda_{max}$ nm (log $\epsilon$): 234.4 (4.58).

Anal. calcd. for $C_{27}H_{36}N_4O_6S_2$: C%, 56.23; H%, 6.29; N%, 9.71. Found: C%, 56.40; H%, 6.42; N%, 9.60.

EXAMPLE 20

Synthesis of 4-diazo-1,7-bis(4-sulfophenyl)-3,5-heptanedione (Compound [IV]; $Y^1=Y^2=H$, $X^1=X^2=-SO_3H$, m=n=2)

1,7-Bis(4-chlorosulfonylphenyl)-4-diazo-3,5-heptanedione (2.0 g, 4.0 mmol) obtained in Example 17, (3) was stirred in a solution of acetonitrile (70 ml) and H$_2$O (50 ml) for 25 h at 30°–35° C. The reaction mixture was washed with dichloromethane (30 ml×3) and then the aqueous layer was evaporated to dryness under reduced pressure to give the title compound as a pale yellow viscous oil; yield: 1.6 g.

$^1$HNMR δppm (DMSO-d$_6$-CDCl$_3$): 2.85 (4H, t, J=7 Hz, —CH$_2$CH$_2$CO—×2), 3.08 (4H, t, J=7 Hz, Ar—CH$_2$CH$_2$CO—×2), 5.32 (2H, bs, SO$_3$H×2), 7.21 (4H, d, J=8 Hz, (Ar3-H, 5-H)×2), 7.54 (4H, d, J=8 Hz, (Ar2-H, 6-H)×2).

IR (Neat) νcm$^{-1}$: 2110, 1635.

Anal. calcd. for C$_{19}$H$_{18}$N$_2$O$_8$S$_2$: C%, 48.92; H%, 3.89; N%, 6.01. Found: C%, 49.20; H%, 4.15; N%, 5.79.

EXAMPLE 21

Synthesis of 4-diazo-1,7-bis(ammonium 4-sulfonatophenyl)-3,5-heptanedione (Compound [IV]; Y$^1$=Y$^2$=H, X$^1$=X$^2$=—SO$_3^\ominus$N$^\oplus$H$_4$, m=n=2)

To a solution of 4-diazo-1,7-bis(4-sulfophenyl)-3,5-heptanedione (700 mg, 1.5 mmol) obtained in Example 20 in acetonitrile (20 ml), 28% aqueous ammonia (400 mg) was added dropwise at 0°–5° C., and stirring was continued for 3 h at the same temperature. Then the mixture was evaporated under reduced pressure, the residue was washed with acetonitrile for several times and evaporated to dryness under reduced pressure to give the title compound as a slightly yellow viscous oil; yield: 650 mg.

$^1$HNMR δppm (CDCl$_3$-DMSO-d$_6$): 2.84 (4H, t, J=7 Hz, —CH$_2$CO—×2), 3.08 (4H, t, J=7 Hz, Ar—CH$_2$—×2), 4.04 (8H, bs, $^\oplus$NH$_4$×2), 7.18 (4H, d, J=8 Hz, (Ar2-H, 6-H)×2), 7.52 (4H, d, J=8 Hz, (Ar3-H, 5-H)×2).

IR (Neat) νcm$^{-1}$: 3300, 2110, 1620.

EXAMPLE 22

Synthesis of 4-diazo-1,7-bis(triethylammonium 4-sulfonatophenyl)-3,5-heptanedione (Compound [IV]; Y$^1$=Y$^2$=H, X$^1$=X$^2$=—SO$_3^\ominus$N$^\oplus$H(C$_2$H$_5$)$_3$, m=n=2)

To a solution of 4-diazo-1,7-bis(4-sulfophenyl)-3,5-heptanedione (700 mg, 1.5 mmol) obtained in Example 20 in acetonitrile (20 ml), triethylamine (600 mg) was added dropwise at 0°–5° C., and stirring was continued for 3 h at the same temperature. Then the mixture was evaporated under reduced pressure, the resultant residue was washed with acetonitrile for several times and evaporated to dryness under reduced presence to give the title compound as a pale yellow viscous oil; yield: 900 mg.

$^1$HNMR δppm (CDCl$_3$-DMSO-d$_6$): 1.16 (18H, t, J=7 Hz, N—CH$_2$CH$_3$×6), 2.84 (4H, t, J=7 Hz, —CH$_2$CO—×2), 3.04–3.12 (16H, m, N—CH$_2$CH$_3$×6 and Ar—CH$_2$—×2), 3.49 (2H, bs, —$^\oplus$NH×2), 7.18(4H, d, J=8 Hz, (Ar2-H, 6-H)×2), 7.51 (4H, d, J=8 Hz, (Ar3-H, 5-H)×2).

IR (Neat) νcm$^{-1}$: 2110, 1650.

EXAMPLE 23

Synthesis of 1,9-bis(4-chlorosulfonylphenyl)-5-diazo-4,6-nonanedione (Compound [IV]; Y$^1$=Y$^2$=H, X$^1$=X$^2$=—SO$_2$Cl, m=n=3)

(1) Synthesis of 1,9-diphenyl-4,6-nonanedione

Using 2,4-pentanedione (93.8 g, 0.94 mol) and β-phenethyl bromide (405 g), the reaction was carried out in the same manner as described in Example 17, (1), and the crude product (350 g) was purified by column chromatography on silica gel (Wako Gel C-200, manufactured by Wako Pure Chemical Industries, Ltd.) with benzene as eluent to give the title compound as a pale yellow oil which was an ca 1:5 mixture of Keto/Enol as seen by the methylene singlet at δ3.43 ppm and the methine singlet at δ5.42 ppm in the $^1$HNMR spectrum; yield: 66.9 g.

$^1$HNMR δppm (CDCl$_3$): 1.85–1.97 (4H, m, —CH$_2$CH$_2$—CO—×2), 2.27 (4H, t, J=8 Hz, —CH$_2$CH$_2$—CO×2), 2.62 (4H, t, J=8 Hz, Ar—CH$_2$CH$_2$—×2) 3.43 (2H, s, —COCH$_2$CO—), 5.42

(1H, s, —C=CH—CO—),
    |

7.10–7.33 (10H, m, Ar-H×2), 15.53 (1H, bs, —OH).

IR (Neat) νcm$^{-1}$: 1725, 1700, 1610.

(2) Synthesis of 5-diazo-1,9-diphenyl-4,6-nonanedione

To a solution of 1,9-diphenyl-4,6-nonanedione (60 g, 0.195 mol) obtained in above (1) and triethylamine (19.8 g, 0.195 mol) in dichloromethane (270 ml), p-toluenesulfonylazide (40.1 g, 0.203 mol) obtained in Example 1 was added dropwise at 0°–5° C., and stirring was continued for 2 h at the same temperature. The reaction mixture was washed with dilute aqueous potassium hydroxide and H$_2$O, dried over anhydrous MgSO$_4$ and evaporated under reduced pressure. The residual solid (68 g) was recrystallized from ethanol to afford the title compound as a slightly yellow leaflets; yield: 42.0 g; mp 54.5°–56.5° C.

$^1$HNMR δppm (CDCl$_3$): 1.93–2.04 (4H, m, —C$_2$CH$_2$—CO—×2), 2.65–2.75 (8H, m, Ar—CH$_2$CH$_2$CH$_2$CO—×2), 7.14–7.31 (10H, m, Ar-H×2).

IR (KBr) νcm$^{-1}$: 2080, 1640.

(3) Synthesis of 1,9-bis(4-chlorosulfonylphenyl)-5-diazo-4,6-nonanedione (Compound [IV]; Y$^1$=Y$^2$=H, X$^1$=X$^2$=—SO$_2$Cl, m=n=3)

Using 5-diazo-1,9-diphenyl-4,6-nonanedione (21.5 g, 64.3 mmol) obtained in above (2), the reaction was carried out in the same manner as described in Example 17, (3), and the residue (10 g) was chromatographed on silica gel (Wako Gel C-200) with n-hexane/dichloromethane (from 1:1 to 1:4) to give the title compound as pale yellow viscous oil; yield; 6.8 g.

$^1$HNMR δppm (CDCl$_3$): 1.98–2.13 (4H, m, —CH$_2$CH$_2$—CO—×2), 2.76–2.89 (8H, m, ArCH$_2$CH$_2$CH$_2$—CO—×2), 7.49 (4H, d, J=8 Hz, (Ar2-H, 6-H)×2), 7.97 (4H, d, J=8 Hz, (Ar3-H, 5-H)×2).

IR (Neat) νcm$^{-1}$: 2110, 1650.

UV (CH$_3$CN) $\lambda_{max}$ nm (log $\epsilon$): 244.2 (4.52).
Anal. calcd. for C$_{21}$H$_{20}$Cl$_2$N$_2$O$_6$S$_2$: C%, 47.46; H%, 3.79; N%, 5.27. Found: C%, 47.39; H%, 3.96; N%, 5.33.

EXAMPLE 24

Synthesis of
5-diazo-1,9-bis(4-methoxysulfonylphenyl)-4,6-nonanedione (Compound [IV]; Y$^1$=Y$^2$=H, X$^1$=X$^2$=—SO$_3$CH$_3$, m=n=3)

Using 1,9-bis(4-chlorosulfonylphenyl)-5-diazo-4,6-nonanedione (800 mg, 1.5 mmol) obtained in Example 23, (3), and methanol (16 ml), the reaction was carried out in the same manner as described in Example 18. The resultant residue (700 mg) was chromatographed on silica gel (Wako Gel C-200) with n-hexane/ethyl acetate (from 5:1 to 3:1) to give the title compound as a slightly yellow viscous oil; yield: 350 mg.

$^1$HNMR $\delta$ppm (CDCl$_3$): 2.02 (4H, q, J=8 Hz, —CH$_2$CH$_2$—CO—×2), 2.77 (8H, t, J=8 Hz, Ar—CH$_2$CH$_2$CH$_2$—CO—×2), 3.75 (6H, s, SO$_3$CH$_3$×2), 7.39 (4H, d, J=8 Hz, (Ar2-H, 6-H)×2), 7.83 (4H, d, J=8 Hz, (Ar3-H, 5-H)×2).

IR (Neat) $\nu$cm$^{-1}$: 2110, 1645.
UV (CH$_3$CN) $\nu_{max}$ nm (log $\epsilon$): 228.3 (4.59).
Anal. calcd. for C$_{23}$H$_{26}$N$_2$O$_8$S$_2$: C%, 52.86; H%, 5.01; N%, 5.36. Found: C%, 52.73; H%, 5.19; N%, 5.22.

EXAMPLE 25

Synthesis of
5-diazo-1,9-bis(4-sulfophenyl)-4,6-nonanedione (Compound [IV]; Y$^1$=Y$^2$=H, X$^1$=X$^2$=—SO$_3$H, m=n=3)

Using 1,9-bis(4-chlorosulfonylphenyl)-5-diazo-4,6-nonanedione (3.0 g, 5.64 mmol) obtained in Example 23, (3), the reaction was carried out in the same procedure as described in Example 20 to afford the title compound as a pale yellow viscous oil; yield: 2.0 g.

$^1$HNMR $\delta$ppm (DMSO-d$_6$): 1.78–1.89 (4H, m, —CH$_2$CH$_2$CH$_2$CO—×2), 2.61 (4H, t, J=7.5 Hz, —CH$_2$CO—×2), 2.76 (4H, t, J=7.5 Hz, Ar—CH$_2$CH$_2$—×2), 4.10 (2H, bs, SO$_3$H×2), 7.18 (4H, d, J=7.5 Hz, (Ar3-H, 5-H)×2), 7.54 (4H, d, J=7.5 Hz, (Ar2-H, 6-H)×2).

IR (Neat) $\nu$cm$^{-1}$: 2150, 1640.
Anal. calcd. for C$_{21}$H$_{22}$N$_2$O$_8$S$_2$: C%, 51.00; H%, 4.48; N%, 5.66. Found: C%, 50.91; H%, 4.63; N%, 5.79.

EXAMPLE 26

Synthesis of 5-diazo-1,9-bis(triethylammonium 4-sulfonatophenyl)-4,6-nonanedione (Compound [IV]; Y$^1$=Y$^2$=H, X$^1$=X$^2$=—SO$_3^{\ominus}$N$^{\oplus}$H(C$_2$H$_5$)$_3$, m=n=3)

Using 5-diazo-1,9-bis(4-sulfophenyl)-4,6-nonanedione (1.75 g, 3.54 mmol) obtained in Example 25, the reaction was carried out in the same manner as described in Example 22 to afford the title compound as a slightly yellow viscous oil; yield: 2.23 g.

$^1$HNMR $\delta$ppm (DMSO-d$_6$): 1.17 (18H, t, J=7.5 Hz, N—CH$_2$CH$_3$×6), 1.76–1.88 (4H, m, —CH$_2$CH$_2$CO—×2), 2.60 (4H, t, J=7.7 Hz, —CH$_2$CO—×2), 2.74 (4H, t, J=7 Hz, Ar—CH$_2$CH$_2$—×2), 3.08 (12H, q, J=7.5 Hz, N—CH$_2$CH$_2$×6), 3.37 (2H, bs, NH×2), 7.15 (4H, d, J=8 Hz, (Ar2-H, 6-H)×2), 7.52 (4H, d, J=8 Hz, (Ar3-H, 5-H) ×2).

IR (Neat) $\nu$cm$^{-1}$: 2700, 2150, 1700, 1640.

Anal. calcd. for C$_{33}$H$_{52}$N$_4$O$_8$S$_2$: C%, 56.87; H%, 7.52; N%, 8.04. Found: C%, 56.61; H%, 7.83 ; N%, 8.29.

EXAMPLE 27

Synthesis of
1,7-bis(3-chlorosulfonyl-4-methylphenyl)-4-diazo-3,5-heptanedione (Compound [IV]; Y$^1$=Y$^2$=—CH$_3$, X$^1$=X$^2$=—SO$_2$Cl, m=n=2)

(1) Synthesis of
1,7-bis(4-methylphenyl)-3,5-heptanedione

Using 2,4-pentandione (195.2 g, 1.95 moles) and 4-methylbenzylchloride (635.4 g), the reaction was carried out in the same manner as described in Example 17, (1), and the residue (568 g) was recrystallized from ethanol to afford the title compound as a white needles which was an ca 1:9 mixture of Keto/Enol as seen by the methylene singlet at $\delta$3.50 ppm and the methine singlet at $\delta$5.43 ppm in the $^1$HNMR spectrum; yield: 155 g; mp 74.8°–75.7° C.

$^1$HNMR $\delta$ppm (CDCl$_3$): 2.31 (6H, s, Ar—CH$_3$×2), 2.55 (4H, t, J=8 Hz, —CH$_2$CH$_2$—CO—×2), 2.88 (4H, t, J=8 Hz, ArCH$_2$CH$_2$—CO—×2), 3.50 (2H, s, —COCH$_2$CO—), 5.43

(1H, s, —C=CH—CO—),
|

7.04–7.11 (8H, m, ArH×2), 15.43 (1H, bs, —OH).
IR (KBr) $\nu$cm$^{-1}$: 1620.

(2) Synthesis of
1,7-bis(4-methylphenyl)-4-diazo-3,5-heptanedione

Using 1,7-bis(4-methylphenyl)-3,5-heptanedione (112.8 g, 0.366 mol) obtained in above (1), the reaction was carried out in the same manner as described in Example 17, (2), and the residue (129 g) was recrystallized from ethanol to afford the title compound as a slightly yellow prisms; yield: 103 g; mp 45.6°–46.8° C.

$^1$HNMR $\delta$ppm (CDCl$_3$): 2.31 (6H, s, Ar—CH$_3$×2), 2.88–3.05 (8H, m, Ar—CH$_2$CH$_2$CO—×2), 7.10 (8H, s, ArH×2).

IR (KBr) $\nu$cm$^{-1}$: 2100, 1660.

(3) Synthesis of
1,7-bis(3-chlorosulfonyl-4-methylphenol)-4-diazo-3,5-heptanedione (Compound [IV]; Y$^1$=Y$^2$=—CH$_3$, X$^1$=X$^2$=—SO$_2$Cl, m=n=2)

Using 1,7-bis(4-methylphenyl)-4-diazo-3,5-heptanedione (90 g, 0.269 mol) obtained in above (2), the reaction was carried out in the same manner as described in Example 17, (3), and the residue was chromatographed on silica gel (Wako Gel C-200) with n-hexane/ethyl acetate (1:1) as eluent to give the title compound as a pale yellow viscous oil; yield: 30 g.

$^1$HNMR $\delta$ppm (CDCl$_3$): 2.74 (6H, s, Ar—CH$_3$×2), 3.04–3.08 (8H, m, Ar—CH$_2$CH$_2$—CO—×2), 7.34 (2H, d, J=8 Hz, Ar5-H×2), 7.49 (2H, dd, J=2 Hz and J=8 Hz, Ar6-H×2), 7.90 (2H, d, J=2 Hz, Ar2-H×2).

IR (Neat) $\nu$cm$^{-1}$: 2110, 1650.
UV (CH$_3$CN) $\lambda_{max}$ nm (log $\epsilon$): 233.1 (4.44).
Anal. calcd. for C$_{21}$H$_{20}$Cl$_2$N$_2$O$_6$S$_2$: C%, 47.46; H%, 3.79; N%, 5.27. Found: C%, 47.54; H%, 3.99; N%, 5.21.

EXAMPLE 28

Synthesis of 4-diazo-1,7-bis(3-methoxysulfonyl-4-methylphenyl)-3,5-heptanedione (Compound [IV]; $Y^1=Y^2=-CH_3$, $X^1=X^2=-SO_3CH_3$, m=n=2)

Using 1,7-bis(3-chlorosulfonyl-4-methylphenyl)-4-diazo-3,5-heptanedione (3.1 g, 5.8 mmol) obtained in Example 27, (3) and methanol (25 ml), the reaction was carried out in the same manner as described in Example 18, and the residue (2.9 g) was chromatographed on silica gel (Wako Gel C-200, manufactured by Wako Pure Chemical Industries, Ltd.) with n-hexane/ethyl acetate (5:1→3:1→2:1) as eluent to give the title compound as a slightly yellow viscous oil; yield: 1.9 g.

$^1$HNMR δppm (CDCl$_3$): 2.60 (6H, s, Ar—CH$_3$×2), 3.01–3.05 (8H, m, Ar—CH$_2$CH$_2$—CO—×2), 3.74 (6H, s, SO$_3$CH$_3$×2), 7.28 (2H, d, J=8 Hz, Ar5-H×2), 7.40 (2H, dd, J=8 Hz and J=2 Hz, Ar6-H×2), 7.82 (2H, d, J=2 Hz, Ar2-H×2).

IR (Neat) νcm$^{-1}$: 2120, 1640.

UV (CH$_3$CN) λ$_{max}$ nm (log ε): 225.4 (4.46).

Anal calcd. for C$_{23}$H$_{26}$N$_2$O$_8$S$_2$: C%, 52.86, H%, 5.01; N%, 5.36. Found: C%, 52.74, H%, 5.24, N%, 5.26.

EXAMPLE 29

Synthesis of 4-diazo-1,7-bis(3-ethoxysulfonyl-4-methylphenyl)-3,5-heptanedione (Compound [IV]: $Y^1=Y^2=-CH_3$, $X^1=X^2=-SO_3C_2H_5$, m=n=2)

Using 1,7-bis(3-chlorosulfonyl-4-methylphenyl)-4-diazo-3,5-heptanedione (700 mg, 1.3 mmol) obtained in Example 27, (3) and ethanol (20 ml), the reaction was carried out in the same manner as described in Example 18, and the residue (700 mg) was chromatographed on silica gel (Wako Gel C-200) with n-hexane/ethyl acetate (from 5:1 to 3:1) as eluent to give the title compound as a slightly yellow viscous oil; yield: 450 mg.

$^1$HNMR δppm (CDCl$_3$): 1.32 (6H, t, J=7 Hz, SO$_3$CH$_2$CH$_3$×2), 2.61 (6H, s, Ar—CH$_3$×2), 3.01–3.08 (8H, m, Ar—CH$_2$CH$_2$—CO—×2), 4.10 (4H, q, J=7 Hz, SO$_3$CH$_2$CH$_3$×2), 4.27 (2H, d, J=8 Hz, Ar5-H×2), 7.39 (2H, dd, J=2 Hz and J=8 Hz, Ar6-H×2), 7.82 (2H, d, J=2 Hz, Ar2-H×2).

IR (Neat) νcm$^{-1}$: 2110, 1645.

UV (CH$_3$CN) λ$_{max}$ nm (log ε): 225.4 (4.49).

Anal. calcd. for C$_{25}$H$_{30}$N$_2$O$_8$S$_2$: C%, 54,53; H%, 5.49; N%, 5.09. Found: C%, 54.46; H%, 5.56; N%, 5.14

EXAMPLE 30

Synthesis of 4-diazo-1,7-bis(3-N,N-diethylaminosulfonyl-4-methylphenyl)-3,5-heptanedione (Compound [IV]; $Y^1=Y^2=-CH_3$, $X^1=X^2=-SO_2N(C_2H_5)_2$, m=n=2)

Using 1,7-bis(3-chlorosulfonyl-4-methylphenyl)-4-diazo-3,5-heptanedione (700 mg, 1.3 mmol) obtained in Example 27, (3) and N,N-diethylamine (1 g), the reaction was carried out in the same manner as described in Example 19, and the resultant oil (800 mg) was chromatographed on silica gel (Wako Gel C-200) with n-hexane/ethyl acetate (from 5:1 to 2:1) as eluent to give the title compound as a pale yellow viscous oil; yield: 380 mg.

$^1$HNMR δppm (CDCl$_3$): 1.21 (12H, t, J=7 Hz, N—CH$_2$CH$_3$×4), 2.55 (6H, s, Ar—CH$_3$×2), 2.96–3.08 (8H, m, —CH$_2$CH$_2$CO—×2), 3.30 (8H, q, J=7 Hz, N—CH$_2$CH$_3$×4), 7.20 (2H, d, J=8 Hz, Ar5-H×2), 7.28 (2H, d, J=8 Hz, Ar6-H ×2), 7.76 (2H, s, Ar2-H×2).

IR (Neat) νcm$^{-1}$: 2120, 1650.

UV (CH$_3$CN) λ$_{max}$ nm (log ε): 227.2 (4.49).

Anal calcd. for C$_{29}$H$_{40}$N$_4$O$_6$S$_2$: C%, 57.59; H%, 6.67; N%, 9.26. Found: C%, 57.71; H%, 6.42; N%, 9.50.

EXAMPLE 31

Synthesis of 4-diazo-1,7-bis(4-methyl-3-sulfophenyl)-3,5-heptanedione (Compound [IV]; $Y^1=Y^2=-CH_3$, $X^1=X^2=-SO_3H$, m=n=2)

To a solution of 1,7-bis(3-chlorosulfonyl-4-methylphenyl)-4-diazo-3,5-heptanedione (1.4 g, 2.6 mmol) obtained in Example 27, (3) in tetrahydrofuran (40 ml), H$_2$O (40 ml) was added, and stirring was continued for 48 h at room temperature. The reaction mixture was washed with dichloromethane for several times and evaporated to dryness under reduced pressure to afford the title compound as a pale yellow viscous oil; yield: 1.2 g.

$^1$HNMR δppm (CDCl$_3$-DMSO-d$_6$) 2.48 (6H, s, CH$_3$×2), 2.80 (4H, t, J=7 Hz, —CH$_2$CO—×2), 3.04 (4H, t, J=7 Hz, A4-CH$_2$—×2), 4.98 (2H, bs, —SO$_3$H ×2), 7.02–7.14 (4H, m, (Ar5-H, 6-H)×2), 7.60 (2H, s, Ar2-H×2).

IR (Neat) νcm$^{-1}$: 2110, 1630.

Anal. calcd. for C$_{21}$H$_{22}$N$_2$O$_8$S$_2$: C%, 51.00; H%, 4.48; N%, 5.66. Found: C%, 50.82; H%, 4.73; N%, 5.93.

EXAMPLE 32

Synthesis of 4-diazo-1,7-bis(ammonium 4-methyl-3-sulfonatophenyl)-3,5-heptanedione (Compound [IV]; $Y^1=Y^2=-CH_3$, $X^1=X^2=-SO_3^{\ominus}N^{\oplus}H_4$, m=n=2)

Using 4-diazo-1,7-bis(4-methyl-3-sulfophenyl)-3,5-heptanedione (1.0 g, 2 mmol) obtained in Example 31, the reaction was carried out in the same procedure as described in Example 21 to give the title compound as a pale yellow viscous oil; yield: 950 mg.

$^1$HNMR δppm (CDCl$_3$-DMSO-d$_6$): 2.60 (6H, s, CH$_3$×2), 2.83 (4H, t, J=7 Hz, —CH$_2$CO—×2), 3.06 (4H, t, J=7 Hz, Ar—CH$_2$—×2), 4.74 (8H, bs, $^{\oplus}$NH$_4$×2), 7.07 (4H, s, (Ar5-H, 6-H)×2), 7.06 (2H, s, Ar2-H×2).

IR (Neat) νcm$^{-1}$: 3300, 2090, 1620.

Anal. calcd. for C$_{21}$H$_{28}$N$_4$O$_8$S$_2$: C%, 47.72; H%, 5.34; N%, 10.60. Found: C%, 47.50; H%, 5.51; N%, 10.91.

EXAMPLE 33

Synthesis of 1,7-bis(4-chlorosulfonyl-1-naphthyl)-4-diazo-3,5-heptanedione (Compound [VI]; $Y^1=Y^2=H$, $X^1=X^2=-SO_2Cl$, m=n=2)

(1) Synthesis of 1,7-di(1-naphthyl)-3,5-heptanedione

Using 2,4-pentanedione (59.6 g. 0.595 mol) and 1-chloromethylnaphthalene (245 g), the reaction was carried out in the same manner as described in Example 17, (1), and the residual oil (200 g) was chromatographed on silica gel (Wako Gel C-200) with n-hexane/benzene (1:4) as eluent to give the title compound as a yellow oil which was an ca 1:6 mixture of Keto/Enol as seen by the methylene singlet at δ3.33 ppm and the methine singlet at δ5.27 ppm in the $^1$HNMR spectrum; yield: 71 g.

$^1$HNMR δppm (CDCl$_3$): 2.56 (4H, t, J=8 Hz, —CH$_2$CH$_2$—CO—×2), 3.24 (4H, t, J=8 Hz, —CH$_2$CH$_2$CO—×2), 3.33 (2H, s, —COCH$_2$CO—), 5.27

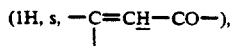
(1H, s, —C=CH—CO—), 7.17-7.91 (14H, m, ArH×2), 15.43 (1H, bs, —OH).
IR (Neat) υcm$^{-1}$: 1720, 1600.

(2) Synthesis of 4-diazo-1,7-di(1-naphthyl)-3,5-heptanedione

Using 1,7-di(1-naphthyl)-3,5-heptanedione (30 g, 79 mmol) obtained in above (1), the reaction was carried out in the same manner as described in Example 17, (2), and the residue (35 g) was chromatographed on silica gel (Wako Gel C-200) with n-hexane/dichloromethane (from 4:1 to 2:1) as eluent to give the title compound as a pale yellow viscous oil; yield: 22.7 g.

$^1$HNMR δppm (CDCl$_3$): 3.14 (4H, t, J=8 Hz, —CH$_2$CH$_2$—CO—×2), 3.42 (4H, t, J=8 Hz, —CH$_2$CH$_2$—CO—×2), 7.34-8.03 (4H, m, ArH×2).
IR (Neat) υcm$^{-1}$: 2120, 1650.

(3) Synthesis of 1,7-bis(4-chlorosulfonyl-1-naphthyl)-4-diazo-3,5-heptanedione (Compound [VI]; $Y^1=Y^2=H$, $X^1=X^2=-SO_2Cl$, m=n=2)

Using 4-diazo-1,7-di(1-naphthyl)-3,5-heptanedione (11.0 g, 27 mmol) obtained in above (2), the reaction was carried out in the same manner as described in Example 17, (3), and the residual oil (5 g) was purified by column chromatography on silica gel (Wako Gel C-200, manufactured by Wako Pure Chemical Industries, Ltd.) with n-hexane/dichloromethane (1:1→1:4→1:9) as eluent to give the title compound as a slightly yellow viscous oil; yield: 2.6 g.

$^1$HNMR δppm (CDCl$_3$): 3.22 (4H, t, —CH$_2$CH$_2$CO—×2), 3.55 (4H, t, —CH$_2$CH$_2$CO—×2), 7.52 (2H, d, J=8 Hz, Ar2-H×2), 7.71-7.88 (4H, m, (Ar6-H, 7-H)×2), 8.20 (2H, d, J=8 Hz, Ar8-H×2), 8.29 (2H, d, J=8 Hz, Ar3-H×2), 8.85 (2H, d, J=8 Hz, Ar5-H×2).
IR (Neat) υcm$^{-1}$: 2100, 1645.
UV (CH$_3$CN) λ$_{max}$ nm (log ε): 239.4 (4.81).
Anal calcd. for C$_{27}$H$_{20}$Cl$_2$N$_2$O$_6$S$_2$: C%, 53.74; H%, 3.34; N%, 4.64. Found: C%, 53.59; H%, 3.51; N%, 4.52.

EXAMPLE 34
Synthesis of 1,7-bis(4-chlorosulfonyl-1-naphthyl)-4-diazo-3,5-heptanedione.

(Compound [VI], $Y^1=Y^2=H$, $X^1=X^2=-SO_2Cl$, m=n=2)

(1) Synthesis of 1,7-bis(potassium 4-sulfonate-1-naphthyl)-3,5-heptanedione

To a suspension of 1,7-di-(1-naphthyl)-3,5-heptanedione (16 g, 40 mmol) obtained in Example 33, (1), and tantalum powder (100 mg) in carbon tetrachloride (35 ml), chlorosulfonic acid (9.4 g, 80 mmol) was added dropwise at −5°~0° C., and stirring was continued for 30 min at the same temperature. After reaction, supernatant solvent was decanted, the residue was treated with cold H$_2$O (80 ml) and filtered to removed inorganic materials. The filtrate was neutralized with dilute aqueous potassium hydroxide and then the precipitate was filtered off. The resultant filtrate was evaporated to dryness under reduced pressure to give the title compound as a pale yellow solid; yield: 17.9 g.

$^1$HNMR δppm (DMSO-d$_6$): 2.68-2.75 (4H, m, —CH$_2$CH$_2$CO—×2), 3.23-3.40 (4H, m, —CH$_2$CH$_2$CO—×2), 7.30-8.15 (10H, m, (Ar2-H, 3-H, 6-H, 7-H, 8-H)×2), 8.77 (2H, d, J=8 Hz, Ar5-H×2).
IR (KBr) υcm$^{-1}$: 1720, 1700, 1600.

(2) Synthesis of 4-diazo-1,7-bis(potassium 4-sulfonato-1-naphthyl)-3,5-heptanedione To a solution of 1,7-bis(potassium 4-sulfonato-1-naphthyl)-3,5-heptanedione (8.9 g, 14.3 mmol) obtained in above (1) and triethylamine (1.6 g, 15.9 mmol) in N,N-dimethylformamide (50 ml) and dichloromethane (10 ml), p-toluenesulfonylazide (3.1 g, 15.5 mmol) obtained in Example 1 was added dropwise at 0°-5° C., and stirring was continued for 4 h at the same temperature. Then the reaction mixture was taken up in dichloromethane (200 ml), the resultant precipitate was filtered, washed thrice with dichloromethane and dried in vacuo to give the title compound as a slightly yellow solid: yield: 6.9 g.

$^1$HNMR δppm (DMSO-d$_6$): 3.17-3.24 (4H, m, —CH$_2$CH$_2$CO—×2), 3.33-3.52 (4H, m, —CH$_2$CH$_2$CO—×2), 7.31-8.04 (10H, m, (Ar2-H, 3-H, 6-H, 7-H, 8-H)×2), 8.92 (2H, d, J=8 Hz, Ar5-H×2).
IR (KBr) υcm$^{-1}$: 2100, 1655.

(3) Synthesis of 1,7-bis(4-chlorosulfonyl-1-naphthyl)-4-diazo-3,5-heptanedione (Compound [VI]; $Y^1=Y^2=H$, $X^1=X^2=-SO_2Cl$, m=n=2)

To a solution of 4-diazo-1,7-bis(potassium 4-sulfonato-1-naphthyl)-3,5-heptanedione (6.0 g, 9.3 mmol) obtained in above (2) in N,N-dimethylformamide (20 ml), thionylchloride (3.4 g, 28 mmol) was added dropwise at 10°-15° C., and stirring was continued for 2 h at 10°-15° C. The reaction mixture was poured into cold H$_2$O (200 ml), extracted with chloroform, the organic extract was washed thrice with H$_2$O, dried over anhydrous MgSO$_4$ and evaporated in vacuo. The resultant residue (1.7 g) was chromatographed on silica gel (Wako Gel C-200) with n-hexane/dichloromethane (1:1→1:4→1:9) as eluent to give the title compound as a slightly yellow viscous oil; yield: 800 mg.

$^1$HNMR, IR and UV spectra of this product were identical with those of the product as described in Example 33, (3).

EXAMPLE 35
Synthesis of 4-diazo-1,7-bis(4-methoxysulfonyl-1-naphthyl)-3,5-heptanedione (Compound [VI]; $Y^1=Y^2=H$, $X^1=X^2=-SO_3CH_3$, m=n=2)

Using 1,7-bis(4-chlorosulfonyl-1-naphthyl)-4-diazo-3,5-heptanedione (4.0 g, 6.6 mmol) obtained in Example 33 and methanol (30 ml), the reaction was carried out in the same manner as described in Example 18, and the resultant residue (3.7 g) was chromatographed on silica gel (Wako Gel C-200, manufactured by Wako Pure Chemical Industries, Ltd.) with n-hexane/ethyl acetate (from 5:1 to 2:1) as eluent to give the title compound as a white amorphous solid; yield: 1.9 g.

$^1$HNMR δppm (CDCl$_3$): 3.20 (4H, t, —CH$_2$CO—×2), 3.51 (4H, t, Ar—CH$_2$—×2), 3.72 (6H, s, —SO$_3$CH$_3$×2), 7.49 (2H, d, J=8 Hz, Ar2-H×2), 7.64–7.74 (4H, m, (Ar6-H, 7-H)×2), 8.15 (2H, dd, J=8 Hz and J=2 Hz, Ar8-H×2), 8.21 (2H, d, J=8 Hz, Ar3-H×2), 8.65 (2H, dd, J=8 Hz and J=2 Hz, Ar5-H×2).

IR (KBr) νcm$^{-1}$: 2120, 1640.

UV (CH$_3$CN) λ$_{max}$ nm (log ε): 228.8 nm (5.01).

EXAMPLE 36

Synthesis of 1,13-bis(4-chlorosulfonyl)-7-diazo-6,8-tridecanedione (Compound [IV]; Y$^1$=Y$^2$=H, X$^1$=X$^2$=—SO$_2$Cl, m=n=5)

(1) Synthesis of 1,13-diphenyl-6,8-tridecanedione

Using 2,4-pentanedione (26.7 g, 0.267 mol) and 1-chloro-4-phenylbutane (110 g, 0.65 mol) obtained in Example 13, (2), the reaction was carried out in the same manner as described in Example 17, (1), and the residue was chromatographed on silica gel (Wako Gel C-200) with benzene/n-hexane (from 4:1 to 10:1) as eluent to afford the title compound as a pale yellow oil which was an ca 1:4 mixture of Keto/Enol as seen by the methylene singlet at δ3.52 ppm and the methine singlet at δ5.44 ppm in the $^1$HNMR spectrum; yield: 2.5 g.

$^1$HNMR δppm (CDCl$_3$): 1.26–1.42 (4H, m, —CH$_2$CH$_2$CH$_2$CO—×2), 1.56–1.69 (8H, m, —CH$_2$—CH$_2$CH$_2$CO—×2), 2.26 (4H, t, J=8 Hz, —CH$_2$CH$_2$CO—CH$_2$—×2), 2.61 (4H, t, J=8 Hz, Ar—CH$_2$—×2), 3.52 (2H, s, —COCH$_2$CO—), 5.44

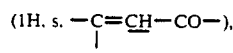

7.15–7.30 (10H, m, Ar-H×2), 15.52 (1H, bs, —OH).

IR (Neat) νcm$^{-1}$: 1700, 1600.

(2) Synthesis of 7-diazo-1,13-diphenyl-6,8-tridecanedione

Using 1,13-diphenyl-6,8-tridecanedione (2.0 g, 5.5 mmol) obtained in above (1), the reaction was carried out in the same manner as described in Example 17, (2), and the residue (2.8 g) was chromatographed on silica gel (Wako Gel C-200) with n-hexane/ethyl acetate (4:1) as eluent to give the title compound as a pale yellow viscous oil; yield: 1.9 g.

$^1$HNMR δppm (CDCl$_3$): 1.34–1.43 (4H, m, —CH$_2$CH$_2$CH$_2$CO—×2), 1.58–1.73 (8H, m, —CH$_2$CH$_2$CH$_2$CH$_2$CO—×2), 2.57–2.64 (4H, m, —CH$_2$CH$_2$CO—×2), 2.67–2.74 (4H, m, Ar—CH$_2$—×2), 7.14–7.30 (10H, m, Ar-H×2).

IR (Neat) νcm$^{-1}$: 2100, 1650.

(3) Synthesis of 1,13-bis(4-chlorosulfonyl)-7-diazo-6,8-tridecanedione (Compound [IV]; Y$^1$=Y$^2$=H, X$^1$=X$^2$=—SO$_2$Cl, m=n=5)

Using 7-diazo-1,13-diphenyl-6,8-tridecanedione (1.6 g, 4.0 mmol) obtained in above (2), the reaction was carried out in the same manner as described in Example 17, (3), and the residue (0.8 g) was chromatographed on silica gel (Wako Gel C-200) with n-hexane/ethyl acetate (from 2:1 to 1:1) as eluent to give the title compound as a slightly yellow viscous oil; yield: 300 mg.

$^1$HNMR δppm (CDCl$_3$): 1.19–1.35 (4H, m, —CH$_2$CH$_2$CH$_2$CO—×2), 1.51–1.94 (12H, m, —CH$_2$—×6), 2.70–2.77 (4H, m, Ar—CH$_2$—×2), 7.41 (4H, d, J=8.5 Hz, (Ar2-H, 6-H)×2), 7.95 (4H, d, J=8.5 Hz, (Ar3-H, 5-H)×2).

IR (Neat) νcm$^{-1}$: 2160, 1650, 1370.

Anal. calcd for C$_{25}$H$_{28}$Cl$_2$N$_2$O$_6$S$_2$: C%, 51.11; H%, 4.80; N%, 4.77. Found: C%, 50.83; H%, 5.06; N%, 4.58.

EXAMPLE 37

Synthesis of mixture of 1,7-bis(6-and 8-chlorosulfonyl-2-naphthyl)-4-diazo-3,5-heptanedione (Compound [VI]; Y$^1$=Y$^2$—H, X$^1$=X$^2$=—SO$_2$Cl, m=n=2)

(1) Synthesis of ethyl 2-naphthoate

To a solution of 2-naphthoic acid (121 g, 0.7 mol) in chloroform (1.5 l) and N,N-dimethylformamide (100 ml), thionyl chloride (167 g) was added dropwise under reflux and stirring was continued for 1 h under reflux. The reaction mixture was concentrated in vacuo and the resultant residue was added dropwise to a solution of triethylamine (106 g) and ethanol (150 ml) at 10° C. or lower. The mixture was stirred for 1 h at room temperature, poured into H$_2$O (1 l), extracted with chloroform, the organic extract was washed with H$_2$O, dried over anhydrous MgSO$_4$ and evaporated under reduced pressure. The residue was distilled under reduced pressure to give the title compound as a colorless oil which solidified in the refrigerator; yield: 112 g; bp 145°–147° C./2 mm Hg; mp 35.0°–36.5° C. (Lit. bp 146°–147° C./1–2 mmHg, mp 35.5°–36.2° C.; C. C. Price. P. H. Michel, J.Am. Chem. Soc., 74, 3652 (1952).).

(2) Synthesis of 2-hydroxymethylnaphthalene

To a suspension of lithium aluminum hydride (19 g) in ethyl ether (500 ml), a solution of ethyl 2-naphthoate (111 g, 0.55 mol) obtained in above (1) in ethyl ether was added dropwise at 10° C. or lower under nitrogen, and stirring was continued for 1 h at room temperature. To this reaction mixture, ethyl acetate (200 ml) was added dropwise to destroy excess LiAlH$_4$. The resultant mixture was poured into hydrochloric acid (200 ml) and H$_2$O (300 ml), the organic layer was separated, washed with H$_2$O, dried over anhydrous MgSO$_4$ and evaporated under reduced pressure. The residual brown solid was recrystallized from ligroin to give the title compound as a white needles; yield: 74.0 g; mp 80.5°–81.5° C. (Lit. mp 80.5°–81° C.; C. R. Hauser, D. N. VanEenam, P. L. Bayless, J. Org. Chem., 23, 354 (1958).).

(3) Synthesis of 2-chloromethylnaphthalene

To a solution of 2-hydroxymethylnaphthalene (53.7 g, 0.34 mol) obtained in above (2) in dichloromethane (300 ml), thionyl chloride (60.7 g) was added dropwise at 30°±5° C., and stirring was continued for 1 h under reflux. After cooling, the reaction mixture was washed twice with H$_2$O, dried over anhydrous MgSO$_4$ and evaporated in vacuo. The resultant oil (54 g) was distilled under reduced pressure to give the title compound as a pale yellow viscous oil which solidified in the refrigerator; yield: 44.2 g; bp 129°–133° C./2 mmHg, mp 46.8°–48.0° C. (Lit. bp 125°–132° C./2 mmHg, mp 47°–48° C.; C. R. Hauser, D. N. VanEenam. P. L. Bayless, J. Org. Chem., 23, 354 (1958).).

(4) Synthesis of 1,7-di-(2-naphthyl)-3,5-heptanedione

Using 2,4-pentanedione (10.0 g, 0.1 mol) and 2-chloromethylnaphthalene (35.3 g, 0.2 mol) obtained in above (3), the reaction was carried out in the same manner as described in Example 17, (1) and crude product (32 g) was chromatographed on silica gel (Wako Gel C-200, manufactured by Wako Pure Chemical Industries, Ltd.) with benzene as eluent to give the title compound as a pale yellow amorphous solid which was an ca 3:2 mixture of Keto/Enol as seen by the methylene singlet at δ3.53 ppm and the methine singlet at δ5.45 ppm in the $^1$HNMR spectrum; yield: 15.4 g; mp 123.0°–125.0° C.

$^1$HNMR δppm (CDCl$_3$): 2.65 (4H, t, J=8 Hz, —CH$_2$CO—×2), 3.06 (4H, t, J=8Hx, —CH$_2$CH$_2$CO—×2), 3.53 (2H, s, —COCH$_2$CO—), 5.45

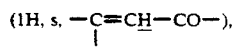

(1H, s, —C=CH—CO—), 7.29 (2H, d, J=6.5 Hz, Ar4-H×2), 7.31–7.40 (4H, m, (Ar5-H, 7-H)×2), 7.60 (2H, bs, Ar1-H×2), 7.73–7.81 (6H, m, (Ar3-H, 6-H, 8-H)×2), 15.46 (1H, bs, OH).

IR (KBr) υcm$^{-1}$: 1600.

(5) Synthesis of 4-diazo-1,7-di-(2-naphthyl)-3,5-heptanedione

Using 1.7-di-(2-naphthyl)-3,5-heptanedione (6.85 g, 18 mmol) obtained in above (4), the reaction was carried out in the same procedure as described in Example 17, (2), and crude oil (9.8 g) was purified by column chromatography on silica gel (Wako Gel C-200) with n-hexane/dichloromethane (1:1) as eluent to give the title compound as a yellow viscous oil; yield: 6.8 g.

$^1$HNMR ppm (CDCl$_3$): 3.12 (8H, bs, —CH$_2$CH$_2$CO—×2), 7.33 (2H, d, J=8 Hz, Ar4-H×2), 7.41–7.62 (4H, m, (Ar5-H, 7-H)×2), 7.64 (2H, bs, Ar1-H×2), 7.75–7.81 (6H, m, (Ar3-H, 6-H, 8-H)×2).

IR (Neat) υcm$^{-1}$: 2100, 1650.

(6) Synthesis of mixture of 1,7-bis(6- and 8-chlorosulfonyl-2-naphthyl)-4-diazo-3,5-heptanedione (Compound [VI]; $Y^1=Y^2=H$, $X^1=X^2=-SO_2Cl$, m=n=2)

Using 4-diazo-1,7-di-(2-naphthyl)-3,5-heptanedione (6.4 g, 15.7 mmol) obtained in above (5), the reaction was carried out in the same manner as described in Example 17, (3) and crude oil (1.1 g) was chromatographed on silica gel (Wako Gel C-200) with n-hexane/dichloromethane (1:2) as eluent to give the title compound as a slightly yellow viscous oil which was an ca 1:1 mixture of 6-isomer/8-isomer by the singlet at δ8.54 ppm and δ8.71 ppm in the $^1$HNMR spectrum; yield: 250 mg.

$^1$HNMR δppm (CDCl$_3$): 3.19–3.31 (8H, m, —CH$_2$CH$_2$—×2), 7.52–8.36 (8H, m, ArH×2), 8.54 (1H, bs, Ar5-H: 6-isomer), 8.71 (1H, d, J=9.0 Hz, Ar7-H: 8-isomer).

IR (Neat) υcm$^{-1}$: 2110, 1650.

Anal. calcd. for C$_{27}$H$_{20}$Cl$_2$N$_2$O$_6$S$_2$: C%, 53.73; H%, 3.34; N%, 4.64. Found: C%, 53.49; H%, 3.45; N%, 4.81.

EXAMPLE 38

Synthesis of 1,7-bis(3-chlorosulfonyl-4-methylphenyl)-4-diazo-3,5-heptanedione (Compound) [VI]; $Y^1=Y^2=-CH_3$, $X^1=X^2=-SO_2Cl$, m=n=2)

Synthesis of 1,7-bis(sodium 4-methyl-3-sulfonatophenyl)-3,5-heptanedione

To a suspension of 1,7-bis(4-methylphenyl)-3,5-heptanedione (41.6 g, 0.135 mol) obtained in Example 27, (1) and tantalum powder (300 mg) in carbon tetrachloride (100 ml), chlorosulfonic acid (31.5 g, 0.27 mol) was added dropwise at −5°~0° C., and stirring was continued for 1 h at room temperature. After reaction, supernatant solvent was decanted, the residue was treated with cold H$_2$O (250 ml) and filtered to remove any inorganic materials. The filtrate was neutralized with dilute aqueous sodium hydroxide and then the precipitate was filtered off. The resultant filtrate was evaporated to dryness under reduced pressure and the residue was recrystallized from ethanol to give the title compound as a white prisms; yield: 40.0 g.

$^1$HNMR δppm (CDCl$_3$-DMSO-d$_6$): 2.41 (4H, 5, J=7 Hz, —CH$_2$CH$_2$CO—×2), 2.59 (6H, s, Ar—CH$_3$×2), 2.82 (4H, t, J=7 Hz, ArCH$_2$CH$_2$—×2), 7.05 (4H, bs, (Ar5-H, 6-H)×2), 7.75 (2H, s, Ar2-H×2).

IR (KBr) υcm$^{-1}$: 1610.

(2) Synthesis of 4-diazo-1,7-bis(sodium 4-methyl-3-sulfonatophenyl)-3,5-heptanedione To a solution of 1,7-bis(sodium 4-methyl-3-sulfonatophenyl)-3,5-heptanedione (35.9 g, 70 mmol) obtained in above (1) and triethylamine (7.9 g, 78 mmol) in N,N-dimethylformamide (200 ml) and dichloromethane (40 ml), p-toluenesulfonylazide (15.0 g, 76 mmol) obtained in Example 1 was added dropwise at 0°–5° C., and stirring was continued for 4 h at the same temperature. Then the reaction mixture was taken up in dichloromethane (800 ml), the resultant precipitate was filtered, washed with dichloromethane and dried in vacuo to afford the title compound as a pale yellow solid; yield: 21.5 g $^1$HNMR δppm (CDCl$_3$-DMSO-d$_6$): 2.59 (6H, s, Ar—CH$_3$×2), 2.86 (4H, t, J=7Hz, —CH$_2$CH$_2$CO—×2), 3.02 (4H, t, J=7Hz, Ar—CH$_2$—×2), 7.08 (4H, bs, (Ar5-H, 6-H)×2), 7.77 (2 H, s, Ar6-H ×2).

IR (KBr) υcm$^{-1}$: 2150, 1640.

(3) Synthesis of 1,7-bis(3-chlorosulfonyl-4-methylphenyl)-4-diazo-3,5-heptanedione (compound [IV]; $Y^1=Y^2=-CH_3$, $X^1=X^2=-SO_2Cl$, m=n=2)

To a solution of 4-diazo-1,7-bis(sodium 4-methyl-3-sulfonatophenyl)-3,5-heptanedione (20.6 g, 40 mmol) obtained in above (2) in N,N-dimethylformamide (60 ml), thionyl chloride (14.3 g, 120 mmol) was added dropwise at 10°–15° C., and stirring was continued for 2 h at room temperature. The reaction mixture was poured into cold H$_2$O (1 l), extracted with chloroform, the organic extract was washed thrice with H$_2$O, dried over anhydrous MgSO$_4$ and evaporated under reduced pressure. The resultant residue (7 g) was chromatographed on silica gel (Wako Gel C-200, manufactured by Wako Pure Chemical Industries, Ltd.) with n-hexane/ethyl acetate (1:1) as eluent to give the title compound as a pale yellow viscous oil; yield: 4.8 g.

¹HNMR, IR and UV spectra of this product were identical with those of the product as described in Example 27, (3).

EXAMPLE 39

Synthesis of 13-(4-chlorosulfonylphenyl)-3-diazo-2,4-tridecanedione

Compound [II]; $R^{13}$=—$CH_3$, $X^1$=—$SO_2Cl$, $Y^1$=H, m=9)

(1) Synthesis of 9-carbomethoxynonanoyl chloride

Thionyl chloride (360 g) was added dropwise to methyl hydrogen sebacate (432.6 g, 2 moles) at 60° C. with vigorous stirring and stirring was continued for 2 h under reflux. The reaction mixture was evaporated and the residue was distilled under reduced pressure to give the title compound as a colorless oil; yield: 400 g; bp 145°-150° C./4 mmHg. (Lit. bp 166°-168° C./14 mmHg; T. D. Heyes, J. C. Roberts, J. Chem. Soc., 1952, 4935).

(2) Synthesis of methyl 9-benzoylnonanoate

To a solution of 9-carbomethoxynonanoyl chloride (213.6 g, 0.91 mol) obtained in above (1) in benzene (900 ml), aluminum chloride (153 g) was added in small portions at 5° C. or lower with vigorous stirring. The mixture was allowed to warm to reflux, stirring was continued for 1 h under reflux and poured into cold $H_2O$ (1 l). The organic layer was separated, washed thrice with $H_2O$ (500 ml), dried over anhydrous $MgSO_4$ and evaporated under reduced pressure. The residual dark orange oil (200 g) was chromatographed on silica gel (Wako Gel C-200, mfd. by Wako Pure Chemical Industries, Ltd.) with n-hexane/ethyl acetate (4:1) as eluent to give the title compound as a colorless viscous oil, which solidified in the refrigerator; yield: 73.8 g, mp 37.0°-38.0° C.

¹HNMR δppm ($CDCl_3$): 1.26-1.40 (8H, m, —$CH_2$—×4), 1.59-1.76 (4H, m, —$COCH_2CH_2$— and —$CH_2CH_2COOCH_3$), 2.30 (2H, t, J=7.3Hz, —$CH_2COOCH_3$), 2.96 (2H, t, J=7.3Hz, Ar—$COCH_2$—), 3.67 (3H, s, —$COOCH_3$), 7.42-7.58 (3H, m, Ar3-H, 4-H, 5-H), 7.96 (2H, d, J=7.3Hz, Ar2-H, 6-H).

IR (KBr) νcm⁻¹: 2900, 2850, 1740, 1680.

(3) Synthesis of 10-phenyldecanoic acid

To a solution of methyl 9-benzoylnonanoate (18.3 g, 66 mmol) obtained in above (2) in diethyleneglycol (100 ml), 80% hydrazine hydrate (11.6 g) and potassium hydroxide (14.9 g) were added and stirring was continued for 2 h under reflux. The reaction mixture was concentrated, poured into $H_2O$ (200 ml), acidified with dilute hydrochloric acid and extracted with ethyl acetate. The organic extract was washed with $H_2O$, dried over anhydrous $MgSO_4$ and evaporated under reduced pressure. The residue was recrystallized from ligroin to give the title compound as a white leaflets; yield: 14.5 g; mp 44.5°-46.5° C. (Lit. mp 46.4°-46 6° C.; R. Goto, A. Ishizawa, M. Yamamura, Nippon Kagaku Zasshi, 88(6), 678 (1967).).

¹HNMR δppm ($CDCl_3$): 1.24-1.31 (10H, m, —$CH_2$—×10), 1.58-1.63 (4H, m, Ar$CH_2CH_2$— and —$CH_2CH_2COOH$), 2.34 (2H, t, J=7.3Hz, —$CH_2COOH$), 2.60 (2H, t, J=7.7Hz, Ar—$CH_2$—), 7.14-7.19 (3H, m, Ar2-H, 4-H, 6-H), 7.25-7.34 (2H, m, Ar3-H, 5-H).

IR (KBr) νcm⁻¹: 1670.

(4) Synthesis of methyl 10-phenyldecanoate

To a solution of 10-phenyldecanoic acid (13.7 g, 55 mmol) obtained in above (3) in dichloromethane (100 ml), thionyl chloride (13.1 g) was added dropwise at 40° C., and stirring was continued for 1 h under reflux. The reaction mixture was concentrated, the resultant residue was added dropwise to a solution of triethylamine (11.2 g) and methanol (20 ml) at 20° C. or lower, and stirring was continued for 2 h at 20°±5° C. The mixture was taken up in $H_2O$ (100 ml), extracted with dichloromethane, the organic layer was washed thrice with $H_2O$ (100 ml), dried over anhydrous $MgSO_4$ and evaporated under reduced pressure. The residue (15.4 g) was purified by column chromatography on silica gel (Wako Gel C-200) with dichloromethane as eluent to give the title compound as a pale yellow oil; yield: 10.1 g.

¹HNMR δppm ($CDCl_3$): 1.24-1.32 (10H, m, —$CH_2$×5), 1.56-1.61 (4H, m, Ar$CH_2CH_2$— and —$CH_2CH_2COO$—), 2.29 (2H, t, J=7.3Hz, —$CH_2COO$—), 2.59 (2H, t, J=7.3Hz, Ar—$CH_2$—), 7.16-7.18 (3H, m, Ar2-H, 4-H, 6-H), 7.24-7.30 (2H, m, Ar3-H, 5-H).

IR (Neat) νcm⁻¹: 1720.

(5) Synthesis of 13-phenyl-2,4-tridecanedione

Using methyl 10-phenyldecanoate (9.2 g, 35 mmol) obtained in above (4) and acetone (2.4 g, 42 mmol), the reaction was carried out in the same manner as described in Example 2, (1), and the crude oil (10.8 g) was chromatographed on silica gel (Wako Gel C-200) with n-hexane/ethyl acetate (10:1) as eluent to give the title compound as a yellow oil which was an ca 3:7 mixture of Keto/Enol as seen by the methylene singlet at δ3.56 ppm and the methine singlet at δ5.48 ppm in the ¹HNMR spectrum; yield: 1.2 g.

¹HNMR δppm ($CDCl_3$): 1.29 (10H, bs, —$CH_2$—×5), 1.59 (4H, bs, Ar—$CH_2CH_2$— and —$CH_2CH_2COCH_2$—), 2.05 (3H, s, —$COCH_3$), 2.26 (2H, t, J=6.5Hz, —$CH_2COCH_2COCH_3$), 2.60 (2H, t, J=7.2Hz, Ar—$CH_2$—), 3.56 (2H, s, —$COCH_2CO$—), 5.48

(1H, s, —C=CHCO—),
        |

7.14-7.19 (3H, m, Ar2-H, 4-H, 6-H), 7.25-7.30 (2H, m, Ar3-H, 5-H), 15.51 (1H, s, OH).

IR (Neat) νcm⁻¹: 1600.

(6) Synthesis of 3-diazo-13-phenyl-2,4-tridecanedione

Using 13-phenyl-2,4-tridecanedione (1.1 g, 4 mmol) obtained in above (5), the reaction was carried out in the same manner as described in Example 2, (2) and the crude oil (1.4 g) was purified by column chromatography on silica gel (Wako Gel C-200) with dichloromethane as eluent to give the title compound as a yellow viscous oil which solidified when kept overnight in the refrigerator; yield: 1.0 g; mp 29.0°-31.0° C.

¹HNMR δppm ($CDCl_3$): 1.29 (10H, bs, —$CH_2$—×5), 1.59-1.64 (4H, m, Ar—$CH_2CH_2$— and —$CH_2CH_2CO$—), 2.44 (3H, s, —$COCH_3$), 2.59 (2H, t, J=7.7Hz, —$CH_2CO$—), 2.69 (2H, t, J=7.5Hz, Ar—$CH_2$—), 7.16–7.18 (3H, m, Ar2-H, 4-H, 6-H), 7.24–7.30 (2H, m, Ar3-H, 5-H).

IR (Neat) $\nu cm^{-1}$: 2090, 1640.

(7) Synthesis of 13-(4-chlorosulfonylphenyl)-3-diazo-2,4-tridecanedione (Compound [II]; $R^{13}=-CH_3$, $X^1=-SO_2Cl$, $Y^1=H$, $m=9$)

Using 3-diazo-13-phenyl-2,4-tridecanedione (0.88 g, 2.8 mmol) obtained in above (6), the reaction was carried out in the same manner as described in Example 2, (3) and the crude product (300 mg) was purified by column chromatography on silica gel (Wako Gel C-200, manufactured by Wako Pure Chemical Industries, Ltd.) with dichloromethane as eluent to afford the title compound as a pale yellow viscous oil which solidified when kept overnight in the refrigerator; yield: 150 mg; mp 48.5°–50.0° C.

$^1$HNMR $\delta$ppm (CDCl$_3$): 1.30 (10H, bs, —CH$_2$—×5), 1.59–1.64 (4H, m, Ar—CH$_2$CH$_2$— and —CH$_2$CH$_2$CO—), 2.45 (3H, s, —COCH$_3$), 2.68–2.75 (4H, m, ArCH$_2$— and —CH$_2$CO—), 7.41 (2H, d, J=6.6Hz, Ar2-H, 6-H), 7.94 (2H, d, J=6.6Hz, Ar3-H, 5-H).

IR (Neat) $\nu cm^{-1}$: 2090, 1630.

UV (CH$_3$CN) $\lambda_{max}$ nm (log $\epsilon$): 241.3 (4.41).

Anal. calcd. for C$_{19}$H$_{25}$ClN$_2$O$_4$S: C%, 55.26; H%, 6.10; N%, 6.78. Found: C%, 55.38; H%, 6.17; N%, 6.69.

EXAMPLE 40

Synthesis of 16-(4-chlorosulfonylphenyl)-3-diazo-2,4-hexadecanedione (Compound [II]; $R^{13}=-CH_3$, $X^1=-SO_2Cl$, $Y^1=H$, $m=12$)

(1) Synthesis of methyl 10-oxo-13-phenyltridecanoate

To a suspension of magnesium (turnings, 17.1 g) in ethyl ether (300 ml), a solution of β-phenethyl bromide (140 g, 0.7 mol) in ethyl ether was added dropwise under mild reflux with vigorous stirring under nitrogen, and stirring was continued for 1 h under reflux. After cooling, the mixture (Grignard reagent) was added dropwise to a solution of 9-carbomethoxynonanoyl chloride (150.1 g, 0.64 mol) in ethyl ether (500 ml) at −50° ∼ −30° C. The mixture was allowed to warm to room temperature, stirred for 2 h at the same temperature and poured into H$_2$O (500 ml). The organic layer was separated, washed with H$_2$O, dried over anhydrous MgSO$_4$ and evaporated in vacuo. The residue (203 g) was chromatographed on silica gel (Wako Gel C-200, manufactured by Wako Pure Chemical Industries, Ltd.) with n-hexane/ethyl acetate (4:1) as eluent to afford the title compound as a colorless oil; yield: 99.7 g.

$^1$HNMR $\delta$ppm (CDCl$_3$): 1.23–1.30 (8H, m, —CH$_2$—×4), 1.51–1.70 (4H, m, —CH$_2$COCH$_2$CH$_2$— and —CH$_2$CH$_2$COO—), 181–2.01 (2H, m, Ar—CH$_2$CH$_2$—), 2.30 (2H, t, J=7.3Hz, —CH$_2$COOCH$_3$), 2.36–2.43 (4H, m, —CH$_2$COCH$_2$—), 2.53–2.72 (2H, m, Ar—CH$_2$—), 3.66 (3H, s, —COOCH$_3$), 7.13–7.31 (5H, m, ArH).

IR (Neat) $\nu cm^{-1}$: 2950, 2800, 1730, 1710.

(2) Synthesis of 13-phenyltridecanoic acid

To a solution of methyl 10-oxo-13-phenyltridecanoate (56.8 g, 0.178 mol) obtained in above (1) in diethylene glycol (600 ml), 80% hydrazine hydrate (50 ml) and potassium hydroxide (70 g) were added and stirring was continued for 2 h under reflux. The reaction mixture was concentrated, poured into H$_2$O (740 ml), acidified with dilute hydrochloric acid and extracted with chloroform. The organic extract was washed with H$_2$O, dried over anhydrous MgSO$_4$ and evaporated in vacuo. The residue was recrystallized from ligroin to afford the title compound as a white leaflets; yield: 44.4 g; mp 51.5°–52.5° C. (Lit. mp 52.2°–52.5° C.; A. Ishizawa, M. Yamamura, R. Goto, Nippon Kagaku Zasshi, 89(8), 815 (1968).).

$^1$HNMR $\delta$ppm (DMSO-d$_6$): 1.24–1.33 (16H, m, —CH$_2$—×8), 1.47–1.58 (4H, m, ArCH$_2$CH$_2$— and —CH$_2$CH$_2$COOH), 2.18 (2H, t, J=7.3Hz, —CH$_2$COOH), 2.48–2.58 (2H, m, ArCH$_2$—), 7.11–7.28 (5H, m, ArH), 11.89 (1H, bs, —COOH).

IR (KBr) $\nu cm^{-1}$: 2900, 2850, 1680.

(3) Synthesis of methyl 13-phenyltridecanoate

13-Phenyltridecanoic acid (22.4 g, 77 mmol) was reacted for 1 h in methanol (60 ml) and sulfuric acid (2.2 g) under reflux. The reaction mixture was concentrated, poured into H$_2$O (100 ml) and extracted with dichloromethane. The organic layer was washed with H$_2$O, dried over anhydrous MgSO$_4$ and evaporated under reduced pressure. The residue (33 g) was chromatographed on silica gel (Wako Gel C-200) with dichloromethane as eluent to give the title compound as a white solid; yield: 17.6 g; mp 30.5°–31.5° C.

$^1$HNMR $\delta$ppm (CDCl$_3$): 1.25–1.29 (16H, m, —CH$_2$—×8), 1.56–1.63 (4H, m, —CH$_2$CH$_2$COOH$_3$ and Ar—CH$_2$CH$_2$—), 2.30 (2H, t, J=7.5 Hz, —CH$_2$COOCH$_3$), 2.60 (2H, t, J=7.8Hz, Ar—CH$_2$—), 3.66 (3H, s, —COOCH$_3$), 7.16–7.18 (3H, m, Ar3-H, 4-H, 5-H), 7.24–7.29 (2H, m, Ar2-H, 6-H).

IR (KBr) $\nu cm^{-1}$: 2900, 2850, 1730.

(4) Synthesis of 16-phenyl-2,4-hexadecanedione

Using methyl 13-phenyltridecanoate (15.9 g, 55 mmol) obtained in above (3) and acetone (3.8 g, 66 mmol), the reaction was carried out in the same procedure as described in Example 2, (1) and the crude oil was purified by column chromatography on silica gel (Wako Gel C-200) with n-hexane/ethyl acetate (10:1) as eluent to give the title compound as a yellow oil which was an ca 3:7 mixture of Keto/Enol as seen by the methylene singlet at δ3.55 ppm and the methine singlet at δ5.47 ppm in the $^1$HNMR spectrum; yield: 1.8 g.

$^1$HNMR $\delta$ppm (CDCl$_3$): 1.29 (16H, bs, —CH$_2$—×8), 1.56–1.63 (4H, m, —CH$_2$CH$_2$CO— and Ar—CH$_2$CH$_2$—), 2.05 (3H, s, —COCH$_3$), 2.26 (2H, t, J=6.5Hz, —CH$_2$COCH$_2$COCH$_3$), 2.60 (2H, t, J=7.2Hz, Ar—CH$_2$—), 3.55 (2H, s, —COCH$_2$CO—), 5.47

(1H, s, —C=CHCO—),
        |

7.14–7.19 (3H, m, Ar2-H, 4-H, 6-H), 7.25–7.30 (2H, m, Ar3-H, 5-H), 15.51 (1H, s, OH).

IR (Neat) $\nu cm^{-1}$: 1605 cm$^{-1}$ (C=O).

(5) Synthesis of 3-diazo-16-phenyl-2,4-hexadecanedione

Using 16-phenyl-2,4-hexadecanedione (1.5 g, 4.5 mmol) obtained in above (4), the reaction was carried out in the same procedure as described in Example 2, (2) and the crude oil was chromatographed on silica gel (Wako Gel C-200) with dichloromethane as eluent to give the title compound as a yellow viscous oil; yield: 1.3 g.

$^1$HNMR δppm (CDCl$_3$): 1.29 (16H, bs, —CH$_2$—×8), 1.59-1 63 (4H, m, ArCH$_2$CH$_2$— and —CH$_2$CH$_2$CO—), 2.44 (3H, s, —COCH$_3$), 2.59 (2H, t, J=7.5Hz, —CH$_2$CO—), 2.70 (2H, t, J=7.5Hz, ArCH$_2$—), 7.16-7.18 (3H, m, Ar2-H, 4-H, 6-H), 7.24-7.30 (2H, m, Ar3-H, 5-H).

IR (Neat) νcm$^{-1}$: 2090, 1640.

(6) Synthesis of 16-(4-chlorosulfonylphenyl)-3-diazo-2,4-hexadecadione (Compound [II]; R$^{13}$=—CH$_3$, X$^1$=—SO$_2$Cl, Y$^1$=H, m=12)

Using 3-diazo-16-phenyl-2,4-hexadecanedione (1.1 g, 3 mmol) obtained in above (5), the reaction was carried out in the same procedure as described in Example 2,(3) and the crude oil (300 mg) was chromatographed on silica gel (Wako Gel C-200, manufactured by Wako Pure Chemical Industries, Ltd.) with dichloromethane as eluent to afford the title compound as a pale yellow viscous oil; yield: 140 mg.

$^1$HNMR δppm (CDCl$_3$): 1.30 (16H bs, —CH$_2$—×8), 1.59-1.63 (4H, m, Ar—CH$_2$CH$_2$— and —CH$_2$CH$_2$CO—), 2.45 (3H, s, —COCH$_3$), 2.68-2.75 (4H, m, Ar—CH$_2$— and —CH$_2$CO—), 7.41 (2H, d, J=6.6Hz, Ar2-H, 6-H), 7.95 (2H, d, J=6.6Hz, Ar3-H, 5-H).

IR (Neat) νcm$^{-1}$: 2090, 1635.

EXAMPLE 41

Synthesis of 5-(4-chlorosulfonylphenyl)-1-cyclohexyl-2-diazo-1,3-pentanedione (Compound [II]; R$^{13}$=Cyclohexyl, X$^1$=—SO$_2$Cl, Y$^1$=H, m=2)

(1) Synthesis of ethyl cyclohexanecarboxylate

To a solution of ethanol (45 ml) and triethylamine (78 g) in toluene (120 ml), cyclohexane carbonyl chloride (75 g, 0.51 mol) was added dropwise at 15° C. or lower, and stirring was continued for 3 h at room temperature. The reaction mixture was poured into cold H$_2$O (350 ml), acidified with dilute hydrochloric acid and extracted with ethyl acetate. The organic extract was washed thrice with H$_2$O (150 ml), dried over anhydrous Na$_2$SO$_4$ and the solvent was removed in vacuo. The residue (93 g) was distilled under reduced pressure to give the title compound as a colorless oil; yield: 64 g; bp 101°-102° C./35 mmHg (Lit: bp 194° C./~760 torr: G. A. Olah, T. Keumi, D. Meider, Synthesis, 1978, 929.).

$^1$HNMR δppm (CDCl$_3$): 1.13-1.92 (13H, m, cyclohexyl 2-H, 2'-H, 3-H, 3'-H, 4-H, 4'-H, 5-H, 5'-H, 6-H, 6'-H and —COOCH$_2$CH$_3$), 2.22-2.35 (1H, m, cyclohexyl 1-H), 4.11 (2H, q, J=7Hz, —COOCH$_2$CH$_3$).

IR (Neat) νcm$^{-1}$: 1725.

(2) Synthesis of 1-cyclohexyl-5-phenyl-1,3-pentanedione

Using ethyl cyclohexane carboxylate (63 g, 0.4 mol) and 4-phenyl-2-butanone (20 g, 0.13 mol), the reaction was carried out in the same manner as described in Example 2, (1) and crude dark orange oil (23 g) was chromatographed on silica gel (Wako Gel C-200) eluting with n-hexane/ethyl acetate (100:1→100:2→100:3) to afford the title compound as a yellow oil which was an ca 3:17 mixture of Keto/Enol by the methylene singlet at δ3.55 ppm and the methine singlet at δ5.45 ppm in the $^1$HNMR spectrum; yield: 2.5 g.

$^1$HNMR δppm (CDCl$_3$): 1.05-1.89 (10H, m, cyclohexyl 2-H, 2'-H, 3-H, 3'-H, 4-H, 4'-H, 5-H, 5'-H, 6-H, 6'-H), 2.20-2.37 (1H, m, cyclohexyl 1-H), 2.65 (2H, t, J=7Hz, —CH$_2$CH$_2$CO—), 2.90 (2H, t, J=7Hz, Ar—CH$_2$—), 3.55 (2H, s, —COCH$_2$CO—), 5.45

(1H, s, —C=CHCH—), 7.15-7.27 (5H, m, ArH), 15.58 (1H, bs, OH).

IR (Neat) νcm$^{-1}$: 1710.

(3) Synthesis of 1-cyclohexyl-2-diazo-5-phenyl-1,3-pentanedione

Using 1-cyclohexyl-5-phenyl-1,3-pentanedione (2.4 g, 9.3 mmol) obtained in above (2), the reaction was carried out in the same manner as described in Example 2, (2) and the crude yellow oil (4 g) was purified by column chromatography on silica gel (Wako Gel C-200) with n-hexane/ethyl acetate (from 100:1 to 100:2) as eluent to give the title compound as a pale yellow viscous oil; yield: 1.9 g).

$^1$HNMR δppm (CDCl$_3$): 1.18-1.53 (6H, m, cyclohexyl 3-H, 3'-H, 4-H, 4'-H, 5-H, 5'-H), 1.68-1.82 (4H, m, cyclohexyl 2-H, 2'-H, 6-H, 6'-H), 2.83-3.00 (3H, m, cyclohexyl 1-H and —CH$_2$CH$_2$CO—), 3.05-3.11 (2H, m, Ar—CH$_2$—), 7.17-7 31 (5H, m, ArH).

IR (Neat) νcm$^{-1}$: 2080, 1630.

(4) Synthesis of 5-(4-chlorosulfonylphenyl)-1-cyclohexyl-2-diazo-1,3-pentanedione (Compound [II]; R$^{13}$=cyclohexyl, X$^1$=—SO$_2$Cl, Y$^1$=H, m=2)

Using 1-cyclohexyl-2-diazo-5-phenyl-1,3-pentanedione (1.7 g, 6 mmol) obtained in above (3), the reaction was carried out in the same manner as described in Example 2, (3) and the crude oil (400 mg) was chromatographed on silica gel (Wako Gel C-200, manufactured by Wako Pure Chemical Industries, Ltd.) eluting with n-hexane/ethyl acetate (3:1) to afford the title compound as a pale yellow viscous oil; yield: 200 mg.

$^1$HMMR δppm (CDCl$_3$): 1.18-1.64 (6H, m, cyclohexyl 3-H, 3'-H, 4-H, 4'-H, 5-H, 5'-H), 1.67-1.90 (4H, m, cyclohexyl 2-H, 2'-H, 6-H, 6'-H), 2.65-2 78 (1H, m, cyclohexyl 1-H), 3.09 (2H, t, J=7Hz, —CH$_2$CH$_2$CO—), 3.20 (2H, t, J=7Hz, ArCH$_2$—), 7.49 (2H, d, J=8Hz, Ar2-H, 6-H), 7.95 (2H, d, J=8Hz, Ar3-H, 5-H).

IR (Neat) νcm$^{-1}$: 2100, 1640.

EXAMPLE 42

Synthesis of 2-[2-(4-chlorosulfonylphenyl)ethyl]-5-diazo-2-methyl-1,3-dioxane-4,6-dione (Compound [VII]; R$^9$=—CH$_3$, X$^3$=—SO$_2$Cl, Y$^3$=H, p=2)

(1) Synthesis of 2-methyl-2-(2-phenylethyl)-1,3-dioxane-4,6-dione

To a solution of malonic acid (56.7 g, 0.55 mol) and acetic anhydride (73 ml), sulfuric acid (2 ml) was added dropwise at 5°-10° C. and stirring was continued for 20 min at the same temperature. To this mixture, 4-phenyl-2-butanone (105 g, 0.7 mol) was added dropwise at 15°-20° C. and stirring was continued for 15 h at the same temperature. The reaction mixture was taken up into H$_2$O, extracted with chloroform, then the organic extract was washed with H$_2$O, dried over anhydrous MgSO$_4$ and evaporated. The resultant solid was recrystallized from aqueous acetone to give the title compound as a white amorphous solid; yield: 68.0 g; mp. 63.0°-65.0° C.

$^1$HNMR δppm (CDCl$_3$): 1.74 (3H, s, CH$_3$), 2.03-2.44 (2H, m, Ar—CH$_2$CH$_2$—), 2.60-3.02 (2H, m, Ar—CH$_2$CH$_2$—), 3.58 (2H, s, —COCH$_2$CO—), 7.16 (5H, s, Ar—H).

IR (KBr) νcm$^{-1}$: 1750.

(2) Synthesis of 5-diazo-2-methyl-2-(2-phenylethyl)-1,3-dioxane-4,6-dione

To a solution of 2-methyl-2-(2-phenylethyl)-1,3-dioxane-4,6-dione (67 g, 0.29 mol) obtained in above (1) and triethylamine (32 g) in ethanol (150 ml), p-toluenesulfonylazide (61 g, 0.3 mol) obtained in Example 1 was added dropwise at −15° ~ −10° C., and stirring was continued for 45 min at the same temperature. The reaction mixture was extracted with dichloromethane, the organic layer was washed with H$_2$O, dried over anhydrous MgSO$_4$ and evaporated under reduced pressure. The resultant residue was chromatographed on silica gel (Wako Gel C-200) with n-hexane/ethyl acetate (10:1→5:1→3:1) as eluent to give the title compound as a yellow crystals; yield: 44.0 g; mp. 50.5°-51.0° C.

$^1$HNMR δppm (CDCl$_3$): 1.74 (3H, s, CH$_3$), 2.04-2.47 (2H, m, Ar—CH$_2$CH$_2$—), 2.60-3.02 (2H, m, Ar—CH$_2$CH$_2$—), 7.16 (5H, s, Ar—H).

IR (KBr) νcm$^{-1}$: 2180, 1695.

(3) Synthesis of 2-[2-(4-chlorosulfonylphenyl)ethyl]-5-diazo-2-methyl-1,3-dioxane-4,6-dione (Compound [VII]; R$^9$=—CH$_3$, X$^3$=—SO$_2$Cl, Y$^3$=H, p=2)

To a solution of 5-diazo-2-methyl-2-(2-phenylethyl)-1,3-dioxane-4,6-dione (8.0 g, 31 mmol) obtained in above (2) in chloroform (35 ml), chlorosulfonic acid (21.5 g) was added dropwise at −20° ~ −10° C. The mixture was stirred for 45 min at the same temperature, poured into cold H$_2$O and extracted with chloroform. The organic extract was washed with H$_2$O, dried over anhydrous MgSO$_4$ and evaporated. The residue was chromatographed on silica gel (Wako Gel C-200, manufactured by Wako Pure Chemical Industries, Ltd.) with n-hexane/ethyl acetate (10:1→4:1→1:1) as eluent to give the title compound as a white amorphous solid; yield: 1.6 g; mp 153.5°-156.5° C.

$^1$HNMR δppm (CDCl$_3$): 1.82 (3H, s, CH$_3$), 2.13-2.56 (2H, m, Ar—CH$_2$CH$_2$—), 2.73-3.19 (2H, m, ArCH$_2$CH$_2$—), 7.44 (2H, d, J=9Hz, Ar2-H, 6-H), 7.97 (2H, d, J=9Hz, Ar3-H, 5-H).

IR (KBr) νcm$^{-1}$: 2170, 1710.

Anal. calcd. for C$_{13}$H$_{11}$ClN$_2$O$_6$S: C%, 43.52; H%, 3.09; N%, 7.81. Found: C%, 43.66; H%, 3.01; N%, 7.69.

EXAMPLE 43

Synthesis of 1,7-bis(4-chloro-3-chlorosulfonylphenyl)-4-diazo-3,5-heptanedione (Compound [IV], Y$^1$=Y$^2$=—Cl, X$^1$=X$^2$=—SO$_2$Cl, m=2, n=2)

(1) Synthesis of 1,7-bis(4-chlorophenyl)-3,5-heptanedione

Using 2,4-pentanedione (20.0 g, 0.2 mol) and 4-chlorobenzyl chloride (74.7 g), the reaction was carried out in the same manner as described in Example 17, (1), and the residual orange red semisolid (69 g) was recrystallized from methanol to give the title compound as s white prisms which was an ca 3:17 mixture of Keto/Enol as seen by the methylene singlet at δ3.51 ppm and the methine singlet at δ5.37 ppm in the $^1$HNMR spectrum; yield: 24.7 g; mp 74.6°-76.1° C.

$^1$HNMR δppm (CDCl$_3$): 2.55 (4H, t, J=7.3Hz, Ar—CH$_2$CH$_2$CO—×2), 2.88 (4H, t, J=7.3Hz, Ar—CH$_2$—×2), 3.51 (2H, s, —COCH$_2$CO—), 5.37

(1H, s, —C=CH—CO—), 7.07-7.11 (4H, m, (Ar2-H, 6-H)×2), 7.23-7.26 (4H, m, (Ar3-H, 5-H)×2), 15.35 (1H, s, —OH).

IR (KBr) νcm$^{-1}$: 3300, 1640, 1600.

(2) Synthesis of 1,7-bis(4-chlorophenyl)-4-diazo-3,5-heptanedione

Using 1,7-bis(4-chlorophenyl)-3,5-heptanedione (12.0 g, 34.4 mmol) obtained in above (1), the reaction was carried out in the same manner as described in Example 17, (2), and the residue (15 g) was purified by column chromatography on silica gel (Wako Gel C-200) with dichloromethane as eluent to give the title compound as a pale yellow crystals; yield: 11.2 g; mp 83° C. (dec.).

$^1$HNMR δppm (CDCl$_3$): 2.93-3.01 (8H, m, Ar—CH$_2$CH$_2$CO—×2), 7.12-7.16 (4H, m, (Ar2-H, 6-H)×2), 7.24-7.27 (4H, m, (Ar3-H, 5-H)×2).

IR (KBr) νcm$^{-1}$: 2100, 1650.

UV (CH$_3$CN) λ$_{max}$ nm (log ε): 225.0 (4.50)

(3) Synthesis of 1,7-bis(4-chloro-3-chlorosulfonylphenyl)-4-diazo-3,5-heptanedione (Compound [IV], Y$^1$=Y$^2$=—Cl, X$^1$=X$^2$=—SO$_2$Cl, m=2, n=2)

Using 1,7-bis(4-chlorophenyl)-4-diazo-3,5-heptanedione (3.98 g, 10.6 mmol) obtained in above (2), the reaction was carried out in the same manner as described in Example 17, (3), and the residue (1.3 g) was chromatographed on silica gel (Wako Gel C-200, manufactured by Wako Pure Chemical Industries, Ltd.) with dichloromethane as eluent to give the title compound as a pale yellow viscous oil; yield: 1.1 g.

$^1$HNMR δppm (CDCl$_3$): 3.08 (8H, s, —CH$_2$—×4), 7.55 (4H, s, (Ar5-H, 6-H)×2), 7.99 (2H, s, Ar2-H×2).

IR (Neat) νcm$^{-1}$: 2110, 1655.

UV (CH$_3$CN) λ$_{max}$ nm (log ε): 227.0 (4.53), 287.0 (3.75).

Anal. calcd. for C$_{19}$H$_{14}$Cl$_4$N$_2$O$_6$S$_2$: C%, 39.88; H%, 2.47; N%, 4.90. Found: C%, 40.09; H%, 2.31; N%, 4.82.

EXAMPLE 44

Synthesis of 1,7-bis(3-chlorosulfonyl-4-methoxyphenyl)-4-diazo-3,5-heptanedione (Compound [IV], $Y^1=Y^2=$—CH$_3$O, $X^1=X^2=$—SO$_2$Cl, m=2, n=2)

(1) Synthesis of 1,7-bis(4-methoxyphenyl)-3,5-heptanedione

Using 2,4-pentanedione (37.3 g, 0.37 mol) and 4-methoxybenzyl chloride (133 g), the reaction was carried out in the same manner as described in Example 17, (1), and the solid residue was purified by recrystalization from ethanol to give the title compound as pale yellow microneedles which were not shown any methylene singlet at δ3.0–4.0 ppm in the $^1$HNMR spectrum; yield: 95.1 g; mp 73.5°-76.2° C.

$^1$HNMR δppm (CDCl$_3$): 2.54 (4H, t, J=8Hz, Ar—CH$_2$CH$_2$CO—×2), 2.86 (4H, t, J=8Hz, Ar—CH$_2$—×2), 3.78 (6H, s, CH$_3$CO—×2), 5.41

(1H, s, —C=CH—CO—),
        |

6.82 (4H, d, J=9Hz, (Ar2-H, 6-H)×2), 7.09 (4H, d, J=9Hz, (Ar3-H, 5-H)×2), 15.43 (1H, bs, —OH).

IR (KBr) νcm$^{-1}$: 1600.

(2) Synthesis of 1,7-bis(4-methoxyphenyl)-4-diazo-3,5-heptanedione

Using 1,7-bis(4-methoxyphenyl)-3,5-heptanedione (4.5 g, 13.2 mmol) obtained in above (1), the reaction was carried out in the same procedure as described in Example 17, (2), and the dark brown oily residue (5.6 g) was purified by silica gel column chromatograpy (Wako Gel C-200) with dichloromethane as eluent to afford the title compound as a yellow viscous oil; yield: 2.4 g.

$^1$HNMR δppm (CDCl$_3$): 2.87-3.03 (8H, m, —CH$_2$—×4), 3.78 (6H, s, CH$_2$O—×2), 6.82 (4H, d, J=8.6Hz, (Ar3-H, 5-H)×2), 7.13 (4H, d, J=8.6Hz, (Ar2-H, 6-H)×2).

IR (Neat) νcm$^{-1}$: 2900, 2100, 1650.

(3) Synthesis of 1,7-bis(3-chlorosulfonyl-4-methoxyphenyl)-4-diazo-3,5-heptanedione (Compound [IV], $Y^1=Y^2=$—CH$_3$O, $X^1=X^2=$—SO$_2$Cl, m=2, n=2)

Using 1,7-bis(4-methoxyphenyl)-4-diazo-3,5-heptanedione (2.2 g, 6 mmol) obtained in above (2), the reaction was carried out in the same manner as described in Example 17, (3), and the residue (1.8 g) was purified by column chromatography on silica gel (Wako Gel C-200, manufactured by Wako Pure Chemical Industries, Ltd.) with n-hexane/ethyl acetate (1:1) as eluent to give the title compound as a pale yellow amorphous solid; yield: 1.7 g; mp 51.0°-52.0° C.

$^1$HNMR δppm (CDCl$_3$): 2.99-3.05 (8H, m, —CH$_2$—×4), 4.03 (6H, s, CH$_3$O—×2), 7.06 (2H, d, J=8.8Hz, Ar5-H×2), 7.57 (2H, dd. J=8.8Hz and 2.2Hz, Ar6-H×2), 7.79 (2H, d, J=2.2Hz, Ar2-H×2).

IR (KBr) νcm$^{-1}$: 2100, 1650.

UV (CH$_3$CN) λ$_{max}$ nm (log ε): 228.0 (4.54), 306.0 (3.88).

Anal. calcd. for C$_{21}$H$_{20}$Cl$_2$N$_2$O$_8$S$_2$: C%, 44.77; H%, 3.58; N%, 4.97. Found: C%, 44.80; H%, 3.51; N%, 5.07.

EXAMPLE 45

A photosensitive composition having the following composition was prepared:

| | |
|---|---|
| $$CH_3-\overset{O}{\underset{\|}{C}}-\overset{N_2}{\underset{\|}{C}}-\overset{O}{\underset{\|}{C}}-(CH_2)_7-\text{Ph}$$ | 1.5 g |
| Poly(p-vinylphenyl) (m.v. 7000) | 8.5 g |
| Diethylene glycol dimethyl ether | 30 g |

The photosensitive composition was spin coated on a semiconductor substrate (Si substrate) in 1.0 μm thickness and prebaked at 90° C. using a hot plate for 2 minutes. Then, a dissolving rate in an alkali developing solution [a 2.38% aqueous solution of tetramethylammonium hydroxide (TMAH)] was measured. The dissolving rate was 400 nm/min, which value was 1/10 of that of poly(p-vinylphenol)(4000 nm/min.). This means that the photosensitive compound mentioned above has a function of lowering the dissolving rate in the alkali developing solution.

Figure 1B:
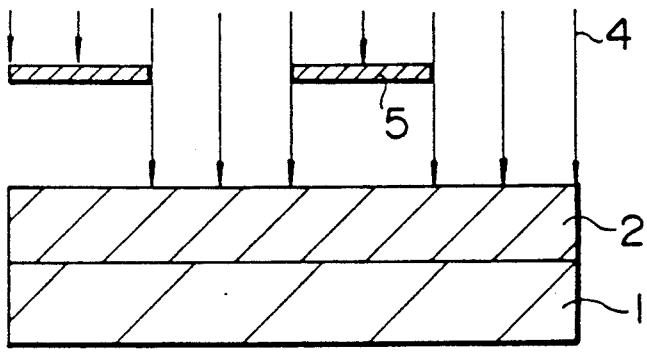
Figure 1C:
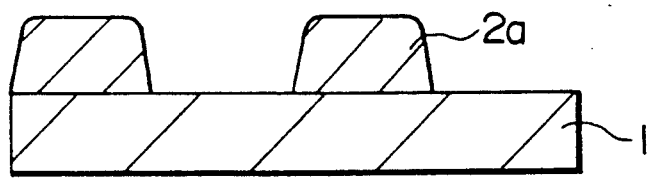
Figure 2:
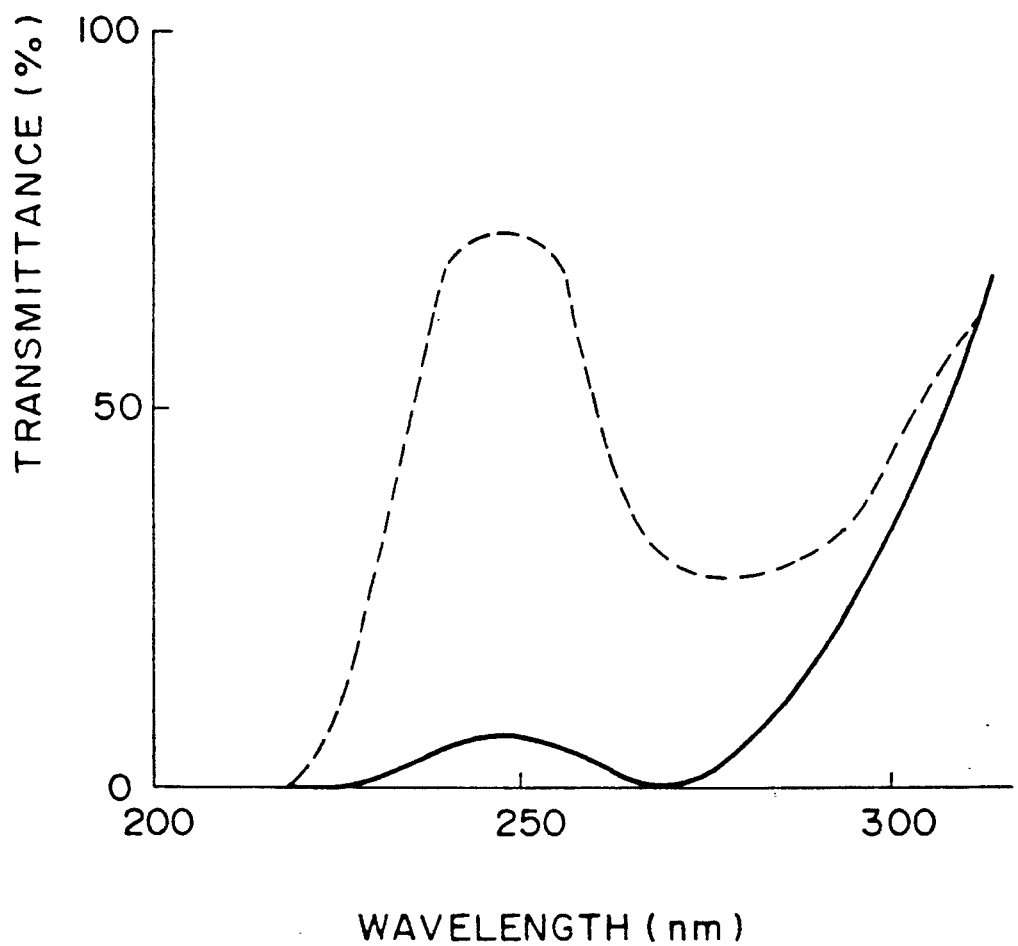
FIG. 2 is a graph showing ultraviolet spectrophotometric characteristics of a photosensitive composition including a photosensitive compound of the present invention at near 248.4 nm.
Figure 3:
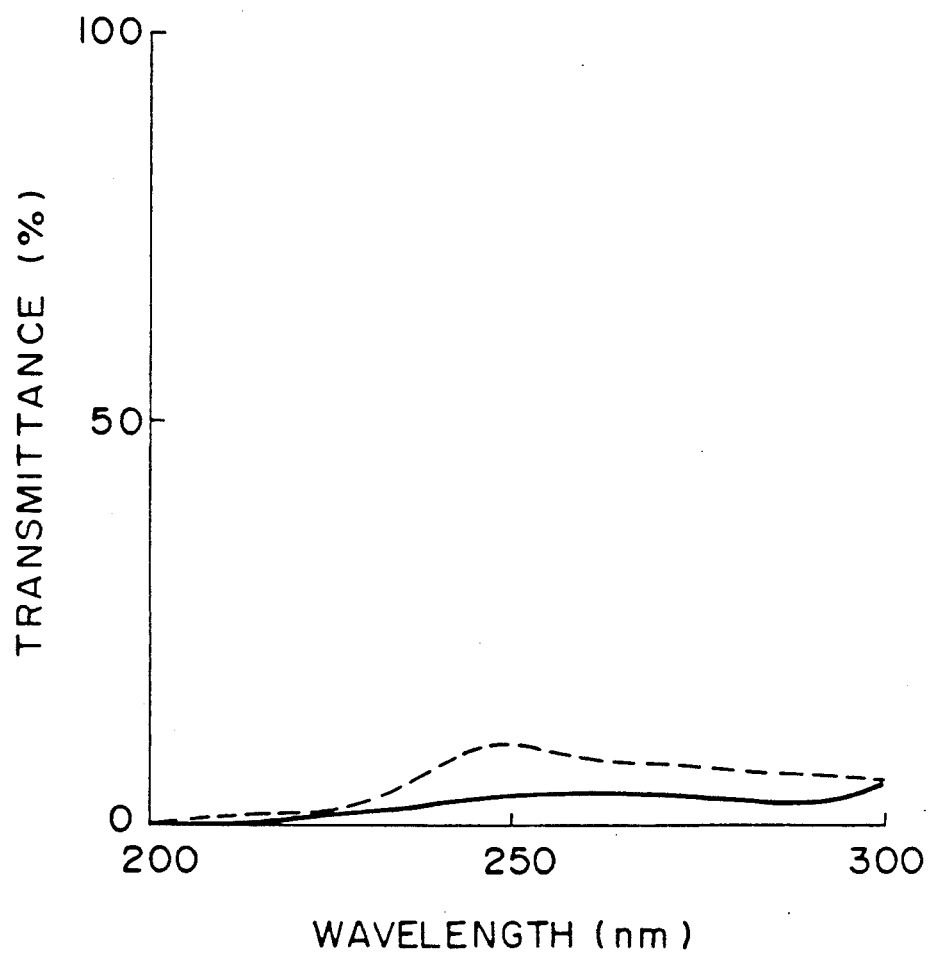
FIG. 3 is a graph showing ultraviolet spectrophotometric characteristics of MP 2400 at near 248.4 nm.

A pattern was formed using the photosensitive composition as shown in FIG. 1. A layer 2 of the photosensitive composition was formed by spin coating on a substrate 1 such as a semiconductor in 1.0 μm thickness [FIG. 1(a)]. The substrate 1 may have thereon an oxidizing film, an insulating film, and an electroconductive film. The layer 2 was selectively exposed to KrF excimer laser 4 via a mask 5 [FIG. 1(b)]. Finally, the layer 2 was dipped in a 2.38% TMAH aqueous solution for 1 minutes to form a pattern 2a by dissolving and removing the exposed portions [FIG. 1(c)]. The resulting pattern 2a had a film erosion of about 40%, an aspect ratio of 70 degree and resolution of 0.4 μm lines and spaces.

EXAMPLE 46

Photosensitive compositions comprising a photosensitive compound of the formula (I) as listed in Table 1, poly(p-vinylphenol) as a polymer and diethylene glycol dimethyl ether as a solvent, in amounts as listed in Table 1 were prepared.

Each photosensitive composition was subjected to the same dissolving test and pattern formation as in Example 45.

The dissolving rate, the film erosion, the aspect ratio and the resolution were measured in the same manner as in Example 45 and listed in Table 1.

TABLE 1

| Run No. | Compound (I) | Mixing ratio (parts) Compound (I) | Mixing ratio (parts) Polymer | Mixing ratio (parts) Solvent | Dissolving rate (nm/min) | Film erosion (%) | Aspect ratio (degree) | Resolution (lines and spaces) (μm) |
|---|---|---|---|---|---|---|---|---|
| 1 | CH$_3$—C(=O)—C(=N$_2$)—C(=O)—(CH$_2$)$_2$—C$_6$H$_5$ | 15 | 85 | 300 | 400 | 40 | 70 | 0.4 |
| 2 | CH$_3$—C(=O)—C(=N$_2$)—C(=O)—(CH$_2$)$_2$—C$_6$H$_4$—SO$_2$Cl | " | " | " | 150 | 15 | 82 | 0.4 |
| 3 | CH$_3$—C(=O)—C(=N$_2$)—C(=O)—(CH$_2$)$_2$—C$_6$H$_4$—SO$_3$H | " | " | " | 200 | 30 | 80 | 0.4 |
| 4 | CH$_3$—C(=O)—C(=N$_2$)—C(=O)—(CH$_2$)$_2$—C$_6$H$_4$—SO$_3^{\ominus}$NH$_4^{\oplus}$ | " | " | " | 200 | 30 | 80 | 0.4 |
| 5 | CH$_3$—C(=O)—C(=N$_2$)—C(=O)—(CH$_2$)$_2$—C$_6$H$_4$—SO$_3^{\ominus}$NH(C$_2$H$_5$)$_3^{\oplus}$ | " | " | " | 200 | 30 | 80 | 0.4 |
| 6 | CH$_3$—C(=O)—C(=N$_2$)—C(=O)—(CH$_2$)$_2$—C$_6$H$_4$—SO$_3$CH$_3$ | " | " | " | 200 | 30 | 80 | 0.4 |
| 7 | CH$_3$—C(=O)—C(=N$_2$)—C(=O)—(CH$_2$)$_2$—C$_6$H$_4$—SO$_3$C$_2$H$_5$ | " | " | " | 170 | 25 | 81 | 0.4 |
| 8 | CH$_3$—C(=O)—C(=N$_2$)—C(=O)—(CH$_2$)$_2$—C$_6$H$_4$—SO$_2$NH$_2$ | " | " | " | 200 | 25 | 80 | 0.4 |
| 9 | CH$_3$—C(=O)—C(=N$_2$)—C(=O)—(CH$_2$)$_2$—C$_6$H$_4$—SO$_2$N(C$_2$H$_5$)$_2$ | " | " | " | 180 | 20 | 81 | 0.4 |
| 10 | CH$_3$—C(=O)—C(=N$_2$)—C(=O)—(CH$_2$)$_2$—C$_6$H$_4$—SO$_2$N(morpholino) | " | " | " | 200 | 25 | 80 | 0.4 |
| 11 | CH$_3$—C(=O)—C(=N$_2$)—C(=O)—(CH$_2$)$_2$—C$_6$H$_4$—SO$_2$N(piperidino) | " | " | " | 200 | 25 | 80 | 0.4 |
| 12 | CH$_3$—C(=O)—C(=N$_2$)—C(=O)—(CH$_2$)$_5$—C$_6$H$_5$ | " | " | " | 120 | 12 | 83 | 0.4 |

TABLE 1-continued
| Run No. | Compound (I) | Mixing ratio (parts) Compound (I) | Mixing ratio (parts) Polymer | Mixing ratio (parts) Solvent | Dissolving rate (nm/min) | Film erosion (%) | Aspect ratio (degree) | Resolution (lines and spaces) (μm) |
|---|---|---|---|---|---|---|---|---|
| 13 | 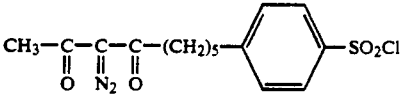 | " | " | " | 80 | 10 | 85 | 0.4 |
| 14 | 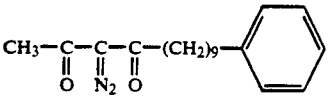 | 12 | 88 | 300 | 100 | 10 | 82 | 0.4 |
| 15 | 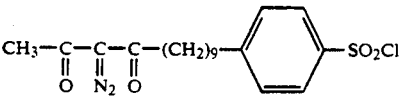 | " | " | " | 80 | 8 | 85 | 0.4 |
| 16 | 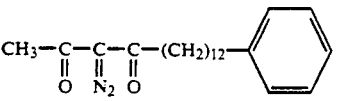 | 10 | 90 | 300 | 80 | 8 | 85 | 0.4 |
| 17 | 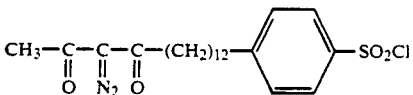 | " | " | " | 50 | 5 | 88 | 0.4 |
| 18 | 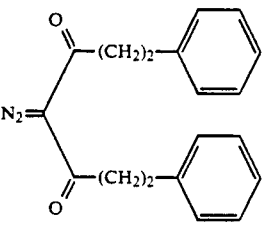 | 15 | 85 | 300 | 300 | 30 | 75 | 0.4 |
| 19 | 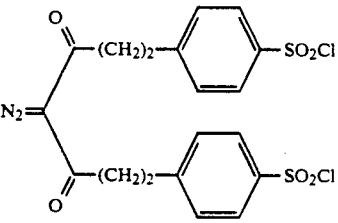 | " | " | " | ≦10 | 0 | 86 | 0.4 |
| 20 | 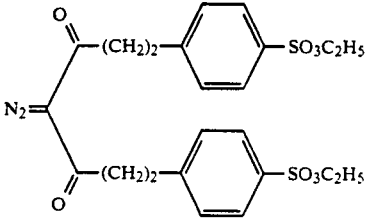 | " | " | " | 150 | 15 | 82 | 0.4 |

TABLE 1-continued

| Run No. | Compound (I) | Mixing ratio (parts) Compound (I) | Polymer | Solvent | Dissolving rate (nm/min) | Film erosion (%) | Aspect ratio (degree) | Resolution (lines and spaces) (μm) |
|---|---|---|---|---|---|---|---|---|
| 21 | N₂=C[C(O)(CH₂)₂-C₆H₄-SO₂N(C₂H₅)₂]₂ | " | " | " | 150 | 15 | 82 | 0.4 |
| 22 | N₂=C[C(O)(CH₂)₂-C₆H₄-SO₃H]₂ | " | " | " | 150 | 15 | 82 | 0.4 |
| 23 | N₂=C[C(O)(CH₂)₃-C₆H₅]₂ | 12 | 88 | 300 | 150 | 15 | 82 | 0.4 |
| 24 | N₂=C[C(O)(CH₂)₃-C₆H₄-SO₂Cl]₂ | " | " | " | ≦10 | 0 | 88 | 0.4 |
| 25 | N₂=C[C(O)(CH₂)₃-C₆H₄-SO₃CH₃]₂ | " | " | " | 90 | 10 | 84 | 0.4 |
| 26 | N₂=C[C(O)(CH₂)₃-C₆H₄-SO₃H]₂ | " | " | " | 90 | 10 | 84 | 0.4 |

TABLE 1-continued

| Run No. | Compound (I) | Mixing ratio (parts) Compound (I) | Polymer | Solvent | Dissolving rate (nm/min) | Film erosion (%) | Aspect ratio (degree) | Resolution (lines and spaces) (μm) |
|---|---|---|---|---|---|---|---|---|
| 27 | O=C-(CH$_2$)$_5$-C$_6$H$_5$ / N$_2$= / O=C-(CH$_2$)$_5$-C$_6$H$_5$ | 10 | 90 | 300 | 100 | 10 | 80 | 0.4 |
| 28 | O=C-(CH$_2$)$_5$-C$_6$H$_4$-SO$_2$Cl / N$_2$= / O=C-(CH$_2$)$_5$-C$_6$H$_4$-SO$_2$Cl | " | " | " | ≦10 | 0 | 90 | 0.4 |
| 29 | O=C-(CH$_2$)$_{12}$-C$_6$H$_5$ / N$_2$= / O=C-(CH$_2$)$_{12}$-C$_6$H$_5$ | " | " | " | ≦10 | 0 | 90 | 0.4 |
| 30 | O=C-(CH$_2$)$_{12}$-C$_6$H$_4$-SO$_2$Cl / N$_2$= / O=C-(CH$_2$)$_{12}$-C$_6$H$_4$-SO$_2$Cl | 6 | 94 | 300 | ≦10 | 0 | 90 | 0.4 |
| 31 | O=C-(CH$_2$)$_2$-C$_6$H$_3$(SO$_2$Cl)(CH$_3$) / N$_2$= / O=C-(CH$_2$)$_2$-C$_6$H$_3$(CH$_3$)(SO$_2$Cl) | 15 | 85 | 300 | ≦10 | 0 | 90 | 0.4 |

TABLE 1-continued

| Run No. | Compound (I) | Mixing ratio (parts) Compound (I) | Mixing ratio (parts) Polymer | Mixing ratio (parts) Solvent | Dissolving rate (nm/min) | Film erosion (%) | Aspect ratio (degree) | Resolution (lines and spaces) (μm) |
|---|---|---|---|---|---|---|---|---|
| 32 | [structure: diazo compound with two -(CH$_2$)$_2$-C$_6$H$_3$(SO$_2$CH$_3$)(CH$_3$) groups] | " | " | " | 100 | 10 | 85 | 0.4 |
| 33 | [structure: diazo compound with two -(CH$_2$)$_2$-C$_6$H$_3$(SO$_3$H)(CH$_3$) groups] | " | " | " | 100 | 10 | 85 | 0.4 |
| 34 | [structure: diazo compound with two -(CH$_2$)$_2$-naphthyl groups] | 10 | 90 | 300 | 80 | 10 | 83 | 0.4 |
| 35 | [structure: diazo compound with two -(CH$_2$)$_2$-(SO$_2$Cl-naphthyl) groups] | " | " | " | ≦10 | 0 | 90 | 0.4 |

TABLE 1-continued

| Run No. | Compound (I) | Mixing ratio (parts) | | | Dissolving rate (nm/min) | Film erosion (%) | Aspect ratio (degree) | Resolution (lines and spaces) (μm) |
|---|---|---|---|---|---|---|---|---|
| | | Compound (I) | Polymer | Solvent | | | | |
| 36 | (structure: diazo bis-[(CH₂)₂-naphthyl-SO₃CH₃]) | " | " | " | 50 | 5 | 84 | 0.4 |
| 37 | (structure: diazo bis-[(CH₂)₂-naphthyl-SO₂Cl]) | " | " | " | ≦10 | 0 | 90 | 0.4 |
| 38 | (structure: diazo with (CH₂)₂-naphthyl and (CH₂)₂-tetrahydronaphthyl) | " | " | " | 80 | 10 | 83 | 0.4 |
| 39 | (structure: diazo malonate with C(CH₃)₂-CH₂-phenyl ester) | 15 | 85 | 300 | 400 | 40 | 70 | 0.4 |
| 40 | (structure: diazo malonate with C(CH₃)₂-(CH₂)₂-phenyl-SO₂Cl ester) | " | " | " | 50 | 5 | 82 | 0.4 |

TABLE 1-continued

| Run No. | Compound (I) | Mixing ratio (parts) Compound (I) | Mixing ratio (parts) Polymer | Mixing ratio (parts) Solvent | Dissolving rate (nm/min) | Film erosion (%) | Aspect ratio (degree) | Resolution (lines and spaces) (μm) |
|---|---|---|---|---|---|---|---|---|
| 41 | Cl—C6H4—(CH2)2—C(=O)—C(=N2)—C(=O)—(CH2)2—C6H4—Cl | " | " | " | ≦10 | 0 | 86 | 0.4 |
| 42 | ClSO2, Cl-substituted di-aryl bis-diazoketone | " | " | " | <10 | 0 | 90 | 0.4 |
| 43 | CH3O—C6H4—(CH2)2—C(=O)—C(=N2)—C(=O)—(CH2)2—C6H4—OCH3 | " | " | " | 150 | 15 | 82 | 0.4 |
| 44 | ClSO2, CH3O-substituted di-aryl bis-diazoketone | " | " | " | <10 | 0 | 90 | 0.4 |

As is clear from Table 1, influences of the methylene chain length are shown in Run Nos. 2, 13, 15 and 17, Run Nos. 1, 12, 14 and 16, Run Nos. 18, 23, 27 and 29, and Run Nos. 19, 24, 28 and 30, wherein longer methylene chains provide good results with smaller using amounts, that is, the sensitivity as the photosensitive compound is increased.

Further, influences of substituents are shown in Run Nos. 1 and 2 to 11, wherein Run No. 2 is the best; in Run Nos. 18 and 19 to 22, wherein Run No. 19 is the best; and in Run Nos. 23 and 24 to 26, wherein Run No. 24 is the best.

What is claimed is:

1. A compound represented by the formula:

$$R^1-\underset{\underset{O}{\|}}{C}-\underset{\underset{N_2}{\|}}{C}-\underset{\underset{O}{\|}}{C}-R^2 \quad (I)$$

wherein $R^1$ is

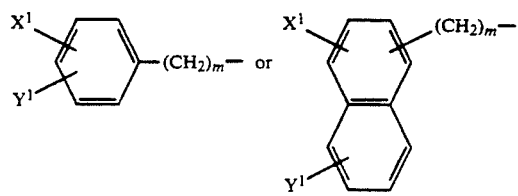

$X^1$ and $Y^1$ are independently a hydrogen atom, a halogen atom, a lower alkyl group having 1 to 5 carbon atoms, a lower alkoxy group having 1 to 5 carbon atoms, —SO$_2$Cl, —SO$_2$Br,

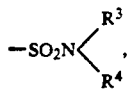

—SO$_3$H or —SO$_3$R$^5$; R$^3$ and R$^4$ are independently a hydrogen atom or a lower alkyl group having 1 to 5 carbon atoms which may have one or more substituents, or R$^3$, R$^4$ and N taken together may form a heterocyclic ring; R$^5$ is a lower alkyl group having 1 to 5 carbon atoms; the —SO$_2$Cl or —SO$_2$Br group may include a quaternary salt thereof; the —SO$_3$H group may include an ammonium salt thereof, an organic base salt thereof and a quaternary salt thereof; m is an integer of 1 to 20; R$^2$ is an alkyl group, a cycloalkyl group, a hydroxyalkyl group, an alkoxyalkyl group,

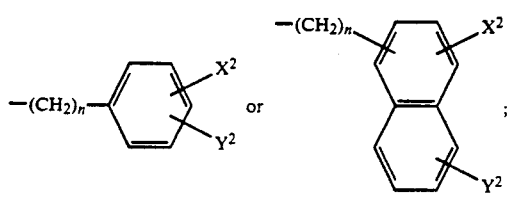

X$^2$ and Y$^2$ are independently a hydrogen atom, a halogen atom, a lower alkyl group having 1 to 5 carbon atoms, a lower alkoxy group having 1 to 5 carbon atoms, —SO$_2$Cl, —SO$_2$Br,

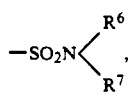

—SO$_3$H or —SO$_3$R$^8$; R$^6$ and R$^7$ are independently a hydrogen atom or a lower alkyl group having 1 to 5 carbon atoms which may have one or more substituents, or R$^6$, R$^7$ and N taken together may form a heterocyclic ring; R$^8$ is a lower alkyl group having 1 to 5 carbon atoms; the —SO$_2$Cl or —SO$_2$Br group may include a quaternary salt thereof; the —SO$_3$H group may include an ammonium salt thereof, an organic base salt thereof and a quaternary salt thereof; n is an integer of 1 to 20.

2. A compound according to claim 1, which is a compound of the formula:

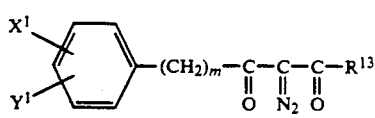

wherein X$^1$, Y$^1$ and m are as defined in claim 1; and R$^{13}$ is an alkyl group, a cycloalkyl group, a hydroxyalkyl group or an alkoxyalkyl group,

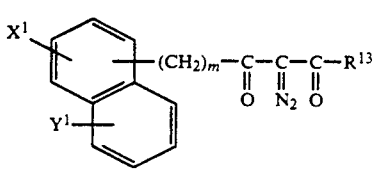

wherein X$^1$, Y$^1$, R$^{13}$ and m are as defined above,

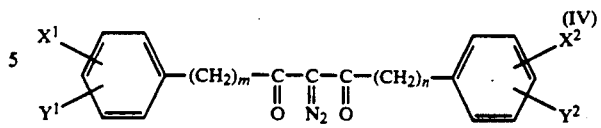

wherein X$^1$, Y$^1$, X$^2$, Y$^2$, m and n are as defined in claim 1,

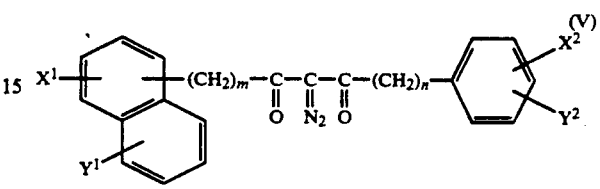

wherein X$^1$, Y$^1$, X$^2$, Y$^2$, m and n are as defined above,

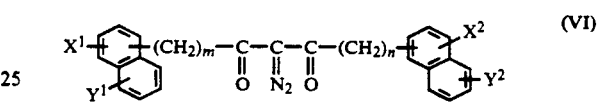

wherein X$^1$, Y$^1$, X$^2$, Y$^2$, m and n are as defined above.

3. A compound according to claim 2, wherein the compound of the formula:

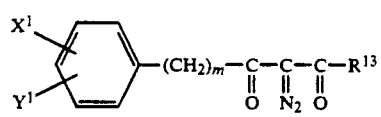

wherein X$^1$, Y$^1$, R$^{13}$ and m are as defined in claim 2, is a compound of the formula:

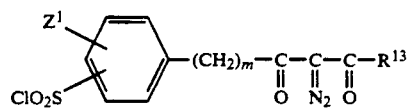

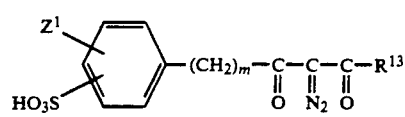

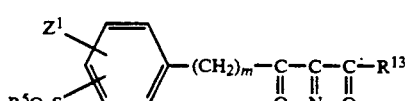

or

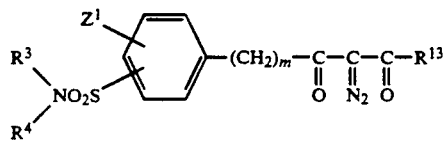

wherein Z$^1$ is hydrogen, halogen, alkyl or alkoxy; R$^3$ and R$^4$ are independently a hydrogen atom, or a lower alkyl group having 1 to 5 carbon atoms which may have one or more substituents, or R$^3$, R$^4$ and N taken together may form a heterocyclic ring; R$^5$ is a lower alkyl group having 1 to 5 carbon atoms; and $R^{13}$ and m are as defined in claim 2.

4. A compound according to claim 2, wherein the compound of the formula:

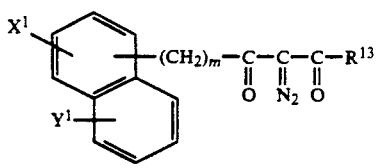
(III)

wherein $X^1$, $Y^1$, $R^{13}$ and m are as defined in claim 2, is a compound of the formula:

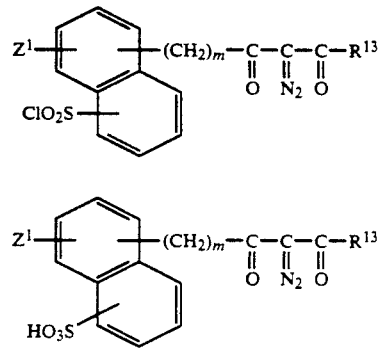

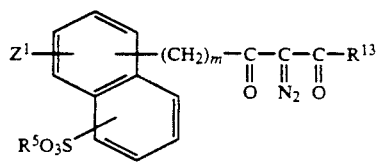

or

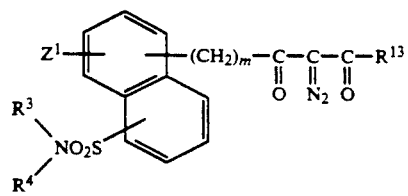

wherein $Z^1$ is hydrogen, halogen, alkyl or alkoxy; $R^3$ and $R^4$ are independently a hydrogen atom, or a lower alkyl group having 1 to 5 carbon atoms which may have one or more substituents, or $R^3$, $R^4$ and N taken together may form a heterocyclic ring; $R^5$ is a lower alkyl group having 1 to 5 carbon atoms; and $R^{13}$ and m are as defined in claim 2.

5. A compound according to claim 2, wherein the compound of the formula:

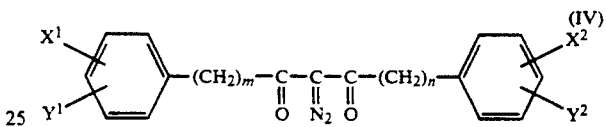
(IV)

wherein $X^1$, $Y^1$, $X^2$, $Y^2$, m and n are as defined in claim 2, is a compound of the formula:

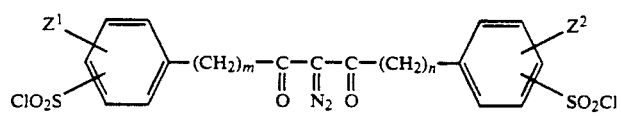

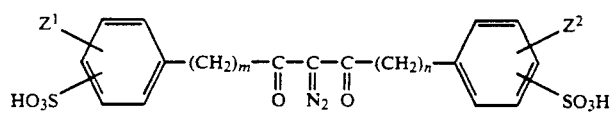

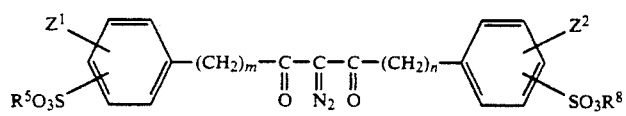

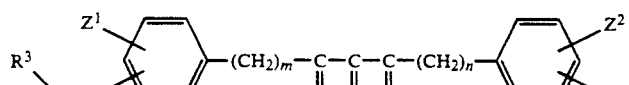
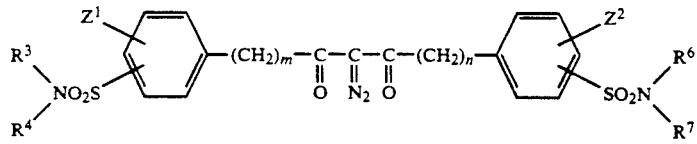

wherein $Z^1$ and $Z^2$ are independently hydrogen, halogen, alkyl or alkoxy; $R^3$, $R^4$, $R^6$ and $R^7$ are independently a hydrogen atom, or a lower alkyl group having 1 to 5 carbon atoms which may have one or more substituents, or $R^3$, $R^4$ or $R^6$, $R^7$ and N taken together may form a heterocyclic ring; $R^5$ and $R^8$ are independently a lower alkyl group having 1 to 5 carbon atoms; and m and n are as defined in claim 2.

6. A compound according to claim 2, wherein the compound of the formula:

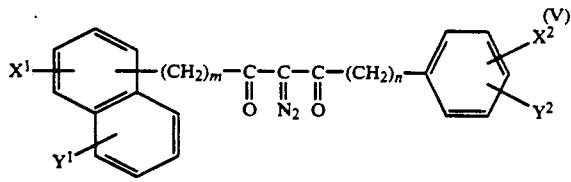

wherein $X^1$, $Y^1$, $X^2$, $Y^2$, m and n are as defined in claim 2, is a compound of the formula:

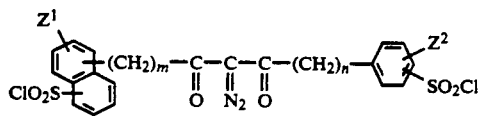

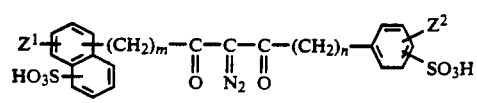

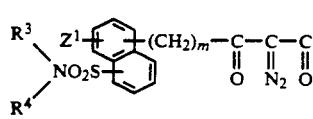

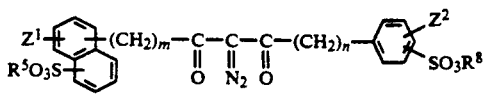

wherein $Z^1$ and $Z^2$ are independently hydrogen, halogen, alkyl or alkoxy; $R^3$, $R^4$, $R^6$ and $R^7$ are independently a hydrogen atom, or a lower alkyl group having 1 to 5 carbon atoms which may have one or more substituents, or $R^3$, $R^4$ or $R^6$, $R^7$ and N taken together may form a heterocyclic ring; $R^5$ and $R^8$ are independently a lower alkyl group having 1 to 5 carbon atoms; and m and n are as defined in claim 2.

7. A compound according to claim 2, wherein the compound of the formula:

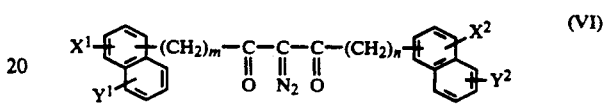

wherein $X^1$, $Y^1$, $X^2$, $Y^2$, m and n are as defined in claim 2, is a compound of the formula:

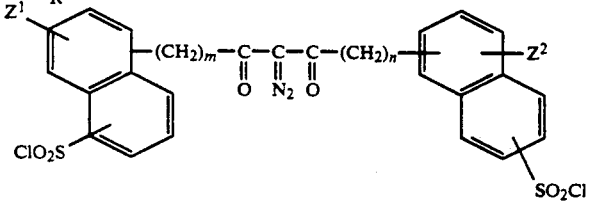

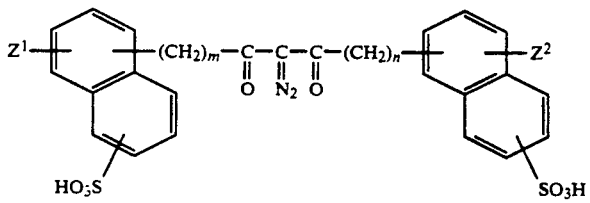

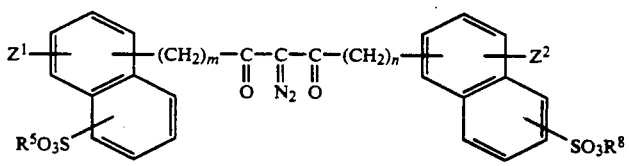

or

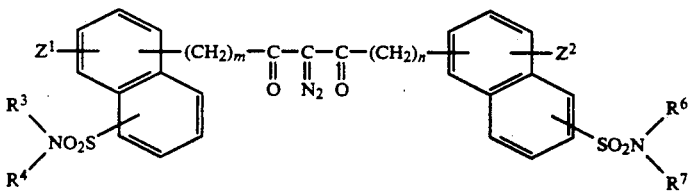

wherein $Z^1$ and $Z^2$ are independently hydrogen, halogen, alkyl or alkoxy; $R^3$, $R^4$, $R^6$ and $R^7$ are independently are independently a hydrogen atom, or a lower alkyl group having 1 to 5 carbon atoms which may have one or more substituents, or $R^3$, $R^4$ or $R^6$, $R^7$ and N taken together may form a heterocyclic ring; $R^5$ and $R^8$ are independently a lower alkyl group having 1 to 5 carbon atoms; and m and n are as defined in claim 2.

8. A compound according to claim 5, which is represented by the formula:

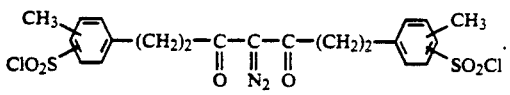

9. A compound according to claim 5, which is represented by the formula:

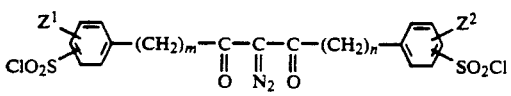

wherein $Z^1$ and $Z^2$ are independently hydrogen or alkyl; m is an integer of 1 to 20 and n is an integer of 1 to 20.

10. A compound according to claim 5, which is represented by the formula:

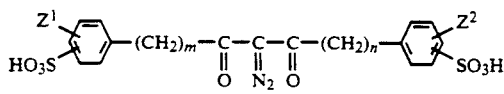

wherein $Z^1$ and $Z^2$ are independently hydrogen or alkyl; m is an integer of 1 to 20 and n is an integer of 1 to 20.

11. A compound according to claim 5, which is represented by the formula:

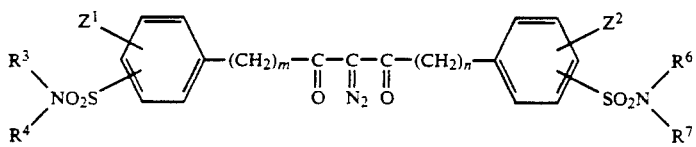

wherein $Z^1$ and $Z^2$ are independently hydrogen, or alkyl; $R^3$, $R^4$, $R^6$ and $R^7$ are independently a hydrogen atom, or a lower alkyl group having 1 to 5 carbon atoms, or $R^3$, $R^4$ or $R^6$, $R^7$ and N taken together may form a heterocyclic ring; m is an integer of 1 to 20; and n is an integer of 1 to 20.

12. A photosensitive compound according to claim 1, which is a compound of the formula:

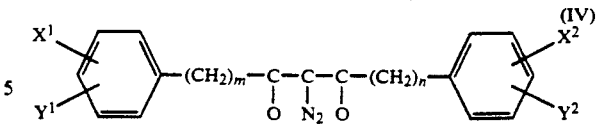

wherein $X^1$ and $Y^1$ are independently a hydrogen atom, a halogen atom, a lower alkyl group having 1 to 5 carbon atoms, a lower alkoxy group having 1 to 5 carbon atoms, $-SO_2Cl$, $-SO_2Br$,

$-SO_3H$ or $-SO_3R^5$; $R^3$ and $R^4$ are independently a hydrogen atom or a lower alkyl group having 1 to 5 carbon atoms which may have one or more substituents, or $R^3$, $R^4$ and N taken together may form a heterocyclic ring; $R^5$ is a lower alkyl group having 1 to 5 carbon atoms; the $-SO_2Cl$ or $-SO_2Br$ group may include a quaternary salt thereof; the $-SO_3H$ group may include an ammonium salt thereof, an organic base salt thereof and a quaternary salt thereof; m is an integer of 1 to 20; $X^2$ and $Y^2$ are independently a hydrogen atom, a halogen atom, a lower alkyl group having 1 to 5 carbon atoms, a lower alkoxy group having 1 to 5 carbon atoms, $-SO_2Cl$, $-SO_2Br$,

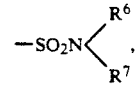

$-SO_3H$ or $-SO_3R^8$; $R^6$ and $R^7$ are independently a hydrogen atom or a lower alkyl group having 1 to 5 carbon atoms which may have one or more substituents or $R^6$, $R^7$ and N taken together may form a heterocyclic ring; $R^8$ is a lower alkyl group having 1 to 5 carbon atoms; the $-SO_2Cl$ or $-SO_2Br$ group may include a quaternary salt thereof; the $-SO_3H$ group may includes an ammonium salt thereof, an organic base salt thereof and a quaternary salt thereof; and n is an integer of 1 to 20.

* * * * *